United States Patent
Yang et al.

(10) Patent No.: US 8,609,622 B2
(45) Date of Patent: Dec. 17, 2013

(54) C-ARYL GLUCOSIDE DERIVATIVES, PREPARATION PROCESS AND PHARMACEUTICAL USE THEREOF

(75) Inventors: Fanglong Yang, Jiangsu (CN); Peng Cho Tang, Jiangsu (CN); Qing Dong, Jiangsu (CN); Wangyang Tu, Jiangsu (CN); Jiang Fan, Jiangsu (CN); Dongliang Guan, Jiangsu (CN); Guangyuan Shen, Jiangsu (CN); Yang Wang, Jiangsu (CN); Jijun Yuan, Jiangsu (CN); Limin Zhang, Jiangsu (CN)

(73) Assignees: Shanghai Hengrui Pharmaceutical Co., Ltd., Shanghai (CN); Jiangsu Hengrui Medicine Co., Ltd., Lianyungang, Jiangsu (CN)

( * ) Notice: Subject to any disclaimer, the term of this patent is extended or adjusted under 35 U.S.C. 154(b) by 0 days.

(21) Appl. No.: 13/813,045

(22) PCT Filed: Jun. 30, 2011

(86) PCT No.: PCT/CN2011/076680
§ 371 (c)(1),
(2), (4) Date: Jan. 29, 2013

(87) PCT Pub. No.: WO2012/019496
PCT Pub. Date: Feb. 16, 2012

(65) Prior Publication Data
US 2013/0130997 A1 May 23, 2013

(30) Foreign Application Priority Data

Aug. 10, 2010 (CN) .......................... 2010 1 0249618
Dec. 6, 2010 (CN) .......................... 2010 1 0589606

(51) Int. Cl.
*A61K 31/70* (2006.01)
*C07H 15/04* (2006.01)

(52) U.S. Cl.
USPC ............................................ 514/23; 536/120

(58) Field of Classification Search
None
See application file for complete search history.

(56) References Cited

U.S. PATENT DOCUMENTS

| 7,169,761 | B2 | 1/2007 | Tomiyama et al. |
| 7,943,748 | B2 | 5/2011 | Matsuoka et al. |
| 8,222,219 | B2 | 7/2012 | Nomura et al. |
| 2012/0184486 | A1* | 7/2012 | Mascitti ................. 514/5.2 |

FOREIGN PATENT DOCUMENTS

| CN | 1671682 A | 9/2005 |
| CN | 1829729 A | 9/2006 |
| CN | 1989132 A | 6/2007 |
| WO | 2010023594 A1 | 3/2010 |
| WO | 2011051864 A1 | 5/2011 |

OTHER PUBLICATIONS

Int'l Search Report issued Oct. 20, 2011 in Int'l Application No. PCT/CN2011/076680.
Mascitti et al, "Stereoselective Synthesis of a Dioxa-bicyclo[3.2.1]octane SGLT2 Inhibitor," Organic Letters, vol. 12, No. 13, pp. 2940-2943 (2010).

* cited by examiner

*Primary Examiner* — Traviss C McIntosh, III
(74) *Attorney, Agent, or Firm* — Panitch Schwarze Belisario & Nadel LLP

(57) ABSTRACT

C-aryl glucoside derivatives, preparation processes and pharmaceutical uses thereof are disclosed. In particular, C-aryl glucoside derivatives represented by formula (I), with each substituent defined in the application, pharmaceutically acceptable salts or stereoisomers thereof, their preparation methods, and pharmaceutical compositions containing the derivatives as well as their uses as therapeutic agents, particularly as sodium-dependent glucose cotransporter (SGLT)-1 inhibitors, are disclosed.

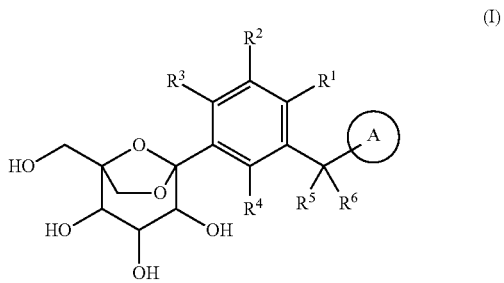

26 Claims, No Drawings

C-ARYL GLUCOSIDE DERIVATIVES, PREPARATION PROCESS AND PHARMACEUTICAL USE THEREOF

CROSS-REFERENCE TO RELATED APPLICATIONS

This application is a Section 371 of International Application No. PCT/CN2011/076680, filed Jun. 30, 2011, which was published in the Chinese language on Feb. 16, 2012, under International Publication No. WO 2012/019496 A1 and the disclosure of which is incorporated herein by reference.

FIELD OF THE INVENTION

The present invention relates to novel C-aryl glucoside derivatives of formula (I) or pharmaceutical salts or stereoisomers thereof, their preparation methods, pharmaceutical compositions containing them and therapeutic uses thereof, particularly their pharmaceutical use as a sodium-dependent glucose cotransporter SGLT inhibitor.

BACKGROUND OF THE INVENTION

In the initial stages of diabetes treatment, diet control and exercise therapy contribute to the preferred glycemic control. When these methods lose control of glycemic regulation, insulin or oral hypoglycemic drugs for treatment are urgently needed. There are various hypoglycemic drugs for clinical treatment comprising biguanides, sulfonylurea compounds, insulin resistance improving agents and α-glucosidase inhibitors etc. Due to different adverse effects of the above drugs, said drugs could not meet the needs of long-term therapy. For example, biguanides could increase the risk of lactic acidosis; sulfonylurea compounds could result in symptoms of hypoglycemia; insulin resistance improving agents could be liable to induce edema and heart failure; and α-glucosidase inhibitors could cause abdominal pain, bloating, diarrhea etc. Consequently, development of novel, safer, and much more effective hypoglycemic agents are highly expected to meet the requirement of diabetes treatment.

Research indicates that glucose transportion by cells is conducted by both facilitative ("passive") glucose transporters (GLUTs) and sodium-coupled ("active") glucose transporters (SGLTs). Members of SGLTs acting as glucose transporters are mainly distributed in the intestine and the proximal tubules of the kidneys, indicating that SGLTs are responsible for the majority of glucose reuptake in the intestine and the kidneys. SGLTs are considered as potential and ideal antidiabetic targets.

More specifically, SGLT-1 is predominantly expressed in the small intestinal mucosal cells and a few are expressed in the myocardium and kidneys. SGLT-1 modulates intestinal glucose absorption cooperatively with GLUTs. A second $Na^+$-glucose transporter, SGLT-2, is responsible for renal glucose reuptake since its highly expressed in the kidneys. Glucose in the urine is actively attached to epithelial cells of renal tubules from the glomerular filtrate and is reused in cells through SGLT-2 transporters. In such stage, SGLT-2 takes charge of 90% reabsorption while SGLT-1 transports the rest of 10%. The conclusion that SGLT-2 is the major glucose transporter has been further confirmed in animal studies. Renal glycemic reuptake of rats will be significantly suppressed when SGLT-2 mRNA expression of renal cortical cells is inhibited by using specific SGLT-2 antisense oligonucleotides. It indicated that novel SGLT (SGLT-1/SGLT-2) inhibitors, which could realize controlling intestinal glucose absorption as well as inhibiting renal glucose reuptake via regulating glucose transport function, could be ideal potential antidiabetic drugs with improvement of glucose excreted from the urine and systematic effect in reducing blood sugar.

In addition, the application of SGLT inhibitors was also found in the treatment of complications of diabetes, including retinopathy, neuropathy, nephropathy and related diseases such as glucose metabolism (impaired glucose homeostasis), hyperinsulinemia, hyperglycemia and obesity etc. Meanwhile, SGLT inhibitors avoided or alleviated adverse response and improved the patient compliance in combination with existing therapeutic drugs involving sulfonamide, thiazolidinedione, metformin and insulin, etc without influencing the efficacy and lowering the amounts of the drugs.

In conclusion, SGLT inhibitors, especially SGLT-2 inhibitors, proved to be promising candidates for use as antidiabetic drugs and new antidiabetic agents. Although patents CN1989132A, CN1671682A, CN1829729A and WO2010023594A1 have disclosed a series of C-aryl glucoside and derivatives for use as SGLT-2 inhibitors, novel compounds having improved efficacy, pharmacokinetics and safety are still urgently required for diabetes and related metabolic disorders. The present invention discloses compounds of formula (I) and it is found that such compounds have excellent SGLT-2 inhibitory and hypoglycemic effects.

BRIEF SUMMARY OF THE INVENTION

The present invention is directed to a compound of formula (I), a tautomer, enantiomer, diastereomer, racemate and pharmaceutically acceptable salt thereof, and a metabolite, precursor or prodrug thereof,

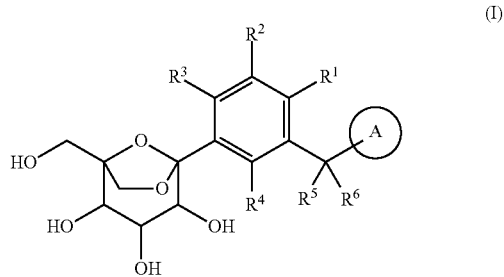

wherein ring A is selected from the group consisting of aryl and heteroaryl, wherein the aryl and heteroaryl are each independently and optionally substituted by one or more groups selected from the group consisting of halogen, alkyl, alkenyl, alkynyl, cycloalkyl, heterocyclyl, aryl, heteroaryl, —OR7, —S(O)mR7, —C(O)R7, —C(O)OR7, —NR8R9 and —C(O)NR8R9, wherein the alkyl, cycloalkyl, heterocyclyl, aryl and heteroaryl are each independently and optionally substituted by one or more groups selected from the group consisting of deuterium, halogen, alkenyl, alkynyl, nitro, cyano, alkoxyl, cycloalkyl, —OR7, —S(O)mR7, —C(O)R7, —C(O)OR7, —NR8R9 and —C(O)NR8R9; R1, R2, R3 and R4 are each independently selected from the group consisting of hydrogen, halogen, cyano, hydroxyl, amino, alkyl, alkoxyl, cycloalkyl, aryl and heteroaryl, wherein the alkyl, alkoxyl, cycloalkyl, aryl and heteroaryl are independently and optionally substituted by one or more groups selected from the group consisting of deuterium, halogen, hydroxyl, amino group, alkyl, alkoxyl, carboxyl and carboxylic ester; alternatively R2 and R3 together with phenyl fuse into a ring which is optionally selected from the group consisting of cycloalkyl, heterocyclyl, aryl and heteroaryl, wherein said cycloalkyl, heterocyclyl, aryl or heteroaryl is each independently optionally substituted by one or more groups selected from the group consisting of halogen, hydroxyl, amino, alkyl, alkoxyl, alkenyl, alkynyl, cycloalkyl, heterocyclyl, aryl, heteroaryl, carboxyl and carboxylic ester; provided that when ring A is phenyl, R2, R3, R4 are each hydrogen, and R1 is selected from the group consisting of hydrogen, C1-4 alkyl, F, Cl, cyano and —OR10, then ring A is not substituted by a group selected from C1-4 alkyl, F, Cl, cyano, hydroxyl, —OR11, C1-2 alkyl substituted by F, —S(O)2R11, C3-6 cycloalkyl and C5-6 saturated heterocyclyl substituted by 1-2 N, O or S; R5 and R6 are each independently selected from the group consisting of hydrogen and deuterium; R7 is selected from the group consisting of hydrogen, deuterium, alkyl, cycloalkyl, heterocyclyl, aryl and heteroaryl, wherein the alkyl, cycloalkyl, heterocyclyl, aryl and heteroaryl are each independently and optionally substituted by one or more groups selected from the group consisting of deuterium, alkyl, halogen, hydroxyl, amino, alkoxyl, cycloalkyl, heterocyclyl, aryl, heteroaryl, carboxyl acid and carboxylic ester; R8 and R9 are each independently selected from the group consisting of hydrogen, alkyl, cycloalkyl, heterocyclyl, aryl and heteroaryl, wherein the alkyl, cycloalkyl, heterocyclyl, aryl and heteroaryl are each independently and optionally substituted by one or more groups selected from the group consisting of alkyl, halogen, hydroxyl, amino group, alkoxyl, cycloalkyl, heterocyclyl, aryl, heteroaryl, carboxyl acid and carboxylic ester; alternatively, R8 and R9 are fused together with the attached nitrogen to form a heterocyclyl, wherein said heterocyclyl contains one or more N, O or S(O)m, heteroatoms, and the heterocyclyl is optionally substituted by one or more groups selected from the group consisting of alkyl, halogen, hydroxyl, alkoxyl, cycloalkyl, heterocyclyl, aryl, heteroaryl, carboxyl acid and carboxylic ester; R10 is C1-4 alkyl; R11 is selected from C1-4 alkyl,

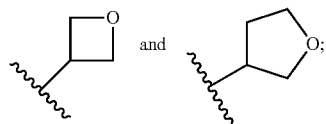 [SMILES: *C1COC1 ; *C1CCOC1]

and m is 0, 1 or 2.

Preferably, the compound of formula (I), a pharmaceutically acceptable salt or stereoisomer thereof, includes a compound having the following formula (II), or a pharmaceutically acceptable salt thereof:

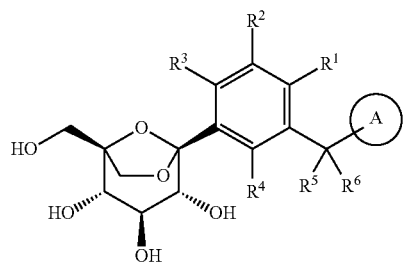

(II)

wherein ring A and R1-R6 are defined as those in formula (I).

Preferably, the present invention relates to the compound of formula (I), a pharmaceutically acceptable salt or stereoisomer thereof, wherein ring A is aryl, wherein the aryl may be optionally substituted by one or more groups selected from the group consisting of halogen, alkyl, alkenyl, alkynyl, cycloalkyl, heterocyclyl, aryl, heteroaryl, —OR7, —S(O)mR7, —C(O)R7, —C(O)OR7, —NR8R9 and —C(O)NR8R9, wherein the alkyl, cycloalkyl, heterocyclyl, aryl and heteroaryl are each independently and optionally substituted by one or more groups selected from the group consisting of deuterium, halogen, alkenyl, alkynyl, nitro, cyano, alkoxyl, cycloalkyl, —OR7, —S(O)mR7, —C(O)R7, —C(O)OR7, —NR8R9 and —C(O)NR8R9.

Preferably, the present invention relates to a compound of formula (I), a pharmaceutically acceptable salt or stereoisomer thereof, wherein ring A is aryl, wherein the aryl is optionally substituted by one or more groups selected from the group consisting of halogen, alkyl, alkenyl, alkynyl, cycloalkyl, heterocyclyl, aryl, heteroaryl, —OR7, —S(O)mR7, —C(O)R7, —C(O)OR7, —NR8R9 and —C(O)NR8R9, wherein the alkyl, cycloalkyl, heterocyclyl, aryl and heteroaryl are each independently and optionally substituted by one or more groups selected from the group consisting of deuterium, halogen, alkenyl, alkynyl, nitro, cyano, alkoxyl, cycloalkyl, —OR7, —S(O)mR7, —C(O)R7, —C(O)OR7, —NR8R9 and —C(O)NR8R9; R2, R3 and R4 are each independently hydrogen; and R1 is halogen.

Preferably, the present invention relates to a compound of formula (I), a pharmaceutically acceptable salt or stereoisomer thereof, wherein ring A is phenyl, wherein the phenyl is optionally substituted by 1 to 5 groups independently selected from the group consisting of halogen and —OR7; R7 is alkyl, wherein the alkyl is optionally substituted by 1 to 3 groups independently selected from the group consisting of deuterium, halogen, alkoxyl and cycloalkoxyl.

Preferably, the present invention relates to a compound of formula (II), a pharmaceutically acceptable salt or stereoisomer thereof, wherein ring A is heteroaryl, wherein the heteroaryl may be optionally substituted by one or more groups selected from the group consisting of halogen, alkyl, alkenyl, alkynyl, cycloalkyl, heterocyclyl, aryl, heteroaryl, —OR7, —S(O)mR7, —C(O)R7, —C(O)OR7, —NR8R9 and —C(O)NR8R9, wherein the alkyl, cycloalkyl, heterocyclyl, aryl and heteroaryl are each independently and optionally substituted by one or more groups selected from the group consisting of deuterium, halogen, alkenyl, alkynyl, nitro, cyano, alkoxyl, cycloalkyl, —OR7, —S(O)mR7, —C(O)R7, —C(O)OR7, —NR8R9 and —C(O)NR8R9.

Preferably, the present invention relates to a compound of formula (II), a pharmaceutically acceptable salt or stereoisomer thereof, wherein ring A is heteroaryl, wherein the heteroaryl is optionally substituted by one or more groups selected from the group consisting of halogen, alkyl, alkenyl, alkynyl, cycloalkyl, heterocyclyl, aryl, heteroaryl, —OR7, —S(O)mR7, —C(O)R7, —C(O)OR7, —NR8R9 and —C(O)NR8R9, wherein the alkyl, cycloalkyl, heterocyclyl, aryl or heteroaryl is each independently and optionally substituted by one or more groups selected from the group consisting of deuterium, halogen, alkenyl, alkynyl, nitro, cyano, alkoxyl, cycloalkyl, —OR7, —S(O)mR7, —C(O)R7, —C(O)OR7, —NR8R9 and —C(O)NR8R9; R2, R3 and R4 are each independently hydrogen; and R1 is a halogen.

Preferably, the present invention relates to a compound of formula (I), a pharmaceutically acceptable salt or stereoisomer thereof, wherein ring A is

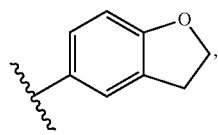 [SMILES: *c1ccc2c(c1)CCO2]

or thienyl.

Preferably, the present invention relates to a compound of formula (I), a pharmaceutically acceptable salt or stereoisomer thereof, wherein ring A is optionally substituted by one or more groups selected from the group consisting of aryl, halogen and —OR7, wherein the aryl is optionally substituted by one or more halogen atoms; provided that that when ring A is substituted by —OR7, wherein R7 is C1-4 alkyl, then ring A is also substituted by one or more halogen atoms.

Preferably, the present invention relates to a compound of formula (I), a pharmaceutically acceptable salt or stereoisomer thereof, wherein R5 or R6 is deuterium.

Preferably, the present invention relates to a compound of formula (I), a pharmaceutically acceptable salt or stereoisomer thereof, wherein R7 is alkyl, and the alkyl is optionally substituted by one or more deuterium atoms.

A compound of formula (I) may contain asymmetric carbon atoms, therefore it can exist in the form of an optically pure diastereomer, a diastereomeric mixture, diastereomeric racemate, a mixture of diastereomeric racemates or as a meso-compound. The present invention includes all these forms. The diastereomeric mixture, diastereomeric racemate or the mixture of diastereomeric racemates can be isolated by conventional methods, such as column chromatography, thin layer chromatography and high performance liquid chromatography.

The preferred compounds of the present invention include, but are not limited to the following:

| Example No | Structure and Name |
|---|---|
| 1 | 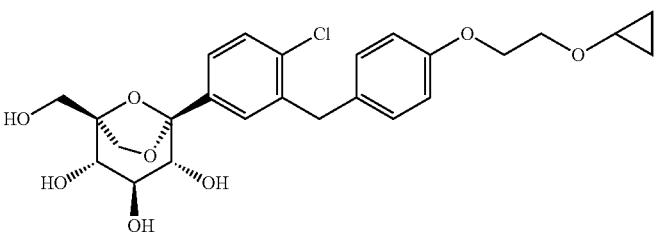<br>(1S,2S,3S,4R,5S)-5-[4-chloro-3-[[4-[2-(cyclopropoxy)ethoxy]phenyl]methyl]phenyl]-1-(hydroxymethyl)-6,8-dioxabicyclo[3.2.1]octane-2,3,4-triol |
| 2 | 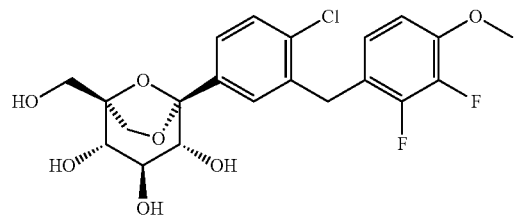<br>(1S,2S,3S,4R,5S)-5-[4-chloro-3-[(2,3-difluoro-4-methoxy-phenyl)methyl]phenyl]-1-(hydroxymethyl)-6,8-dioxabicyclo[3.2.1]octane-2,3,4-triol |
| 3 | 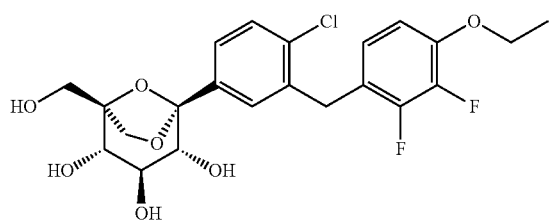<br>(1S,2S,3S,4R,5S)-5-[4-chloro-3-[(4-ethoxy-2,3-difluoro-phenyl)methyl]phenyl]-1-(hydroxymethyl)-6,8-dioxabicyclo[3.2.1]octane-2,3,4-triol |
| 4 | 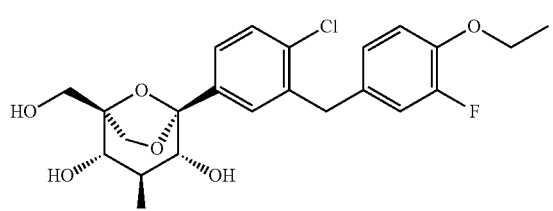<br>(1S,2S,3S,4R,5S)-5-[4-chloro-3-[(4-ethoxy-3-fluoro-phenyl)methyl]phenyl]-1-(hydroxymethyl)-6,8-dioxabicyclo[3.2.1]octane-2,3,4-triol |

| Example No | Structure and Name |
|---|---|
| 5 | 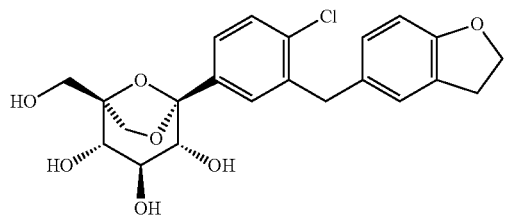<br>(1S,2S,3S,4R,5S)-5-[4-chloro-3-(2,3-dihydrobenzofuran-5-ylmethyl)phenyl]-1-(hydroxymethyl)-6,8-dioxabicyclo[3.2.1]octane-2,3,4-triol |
| 6 | 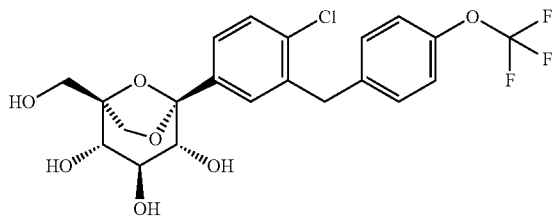<br>(1S,2S,3S,4R,5S)-5-[4-chloro-3-[[4-(trifluoromethoxy)phenyl]methyl]phenyl]-1-(hydroxymethyl)-6,8-dioxabicyclo[3.2.1]octane-2,3,4-triol |
| 7 | 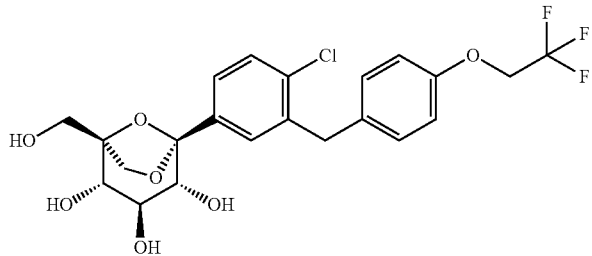<br>(1S,2S,3S,4R,5S)-5-[4-chloro-3-[[4-(2,2,2-trifluoroethoxy)phenyl]methyl]phenyl]-1-(hydroxymethyl)-6,8-dioxabicyclo[3.2.1]octane-2,3,4-triol |
| 8 | 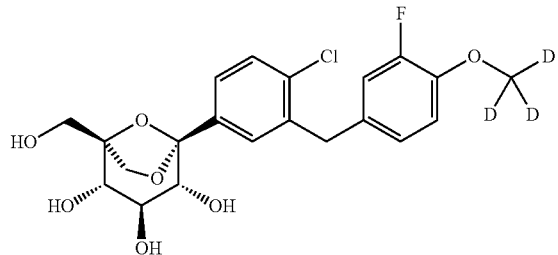<br>(1S,2S,3S,4R,5S)-5-[4-chloro-3-[[3-fluoro-4-(trideuteriomethoxy)phenyl]methyl]phenyl]-1-(hydroxymethyl)-6,8-dioxabicyclo[3.2.1]octane-2,3,4-triol |

| Example No | Structure and Name |
|---|---|
| 9 | 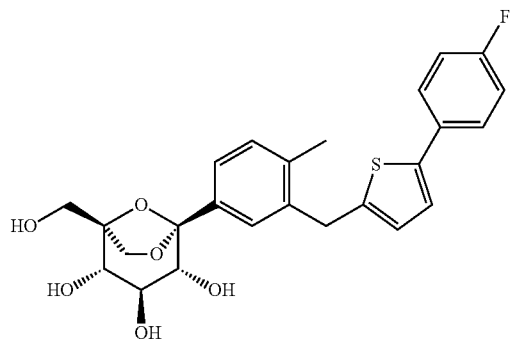<br>(1S,2S,3S,4R,5S)-5-[3-[[5-(4-fluorophenyl)-2-thienyl]methyl]-4-methyl-phenyl]-1-(hydroxymethyl)-6,8-dioxabicyclo[3.2.1]octane-2,3,4-triol |
| 10 | 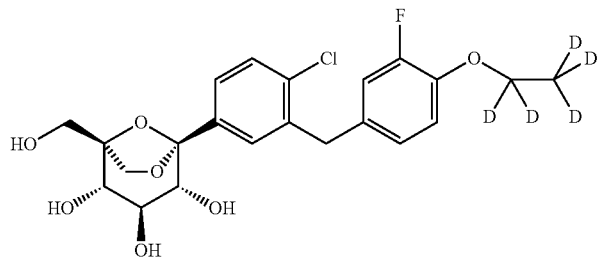<br>(1S,2S,3S,4R,5S)-5-[4-chloro-3-[[3-fluoro-4-(1,1,2,2,2-pentadeuterioethoxy)phenyl]methyl]phenyl]-1-(hydroxymethyl)-6,8-dioxabicyclo[3.2.1]octane-2,3,4-triol |
| 11 | 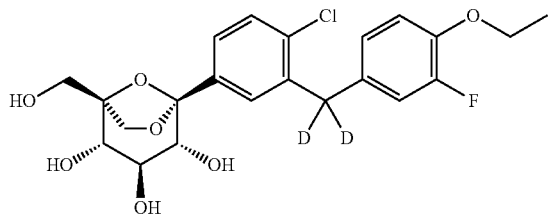<br>(1S,2S,3S,4R,5S)-5-[4-chloro-3-[dideuterio-(4-ethoxy-3-fluoro-phenyl)methyl]phenyl]-1-(hydroxymethyl)-6,8-dioxabicyclo[3.2.1]octane-2,3,4-triol |
| 12 | 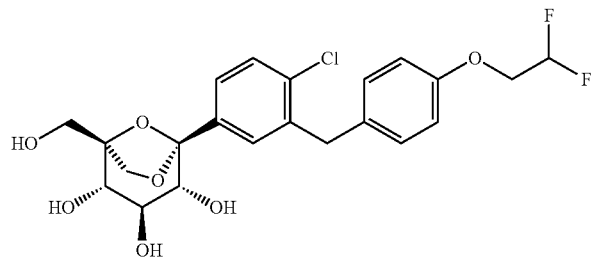<br>(1S,2S,3S,4R,5S)-5-[4-chloro-3-[[4-(2,2-difluoroethoxy)phenyl]methyl]phenyl]-1-(hydroxymethyl)-6,8-dioxabicyclo[3.2.1]octane-2,3,4-triol | or pharmaceutically acceptable salts thereof, or any stereochemically isomers thereof.

This invention also relates to a process for preparing a compound of formula (I), comprising the following steps of:

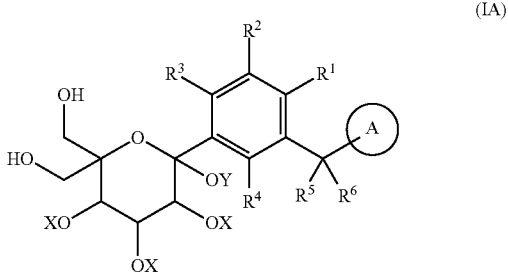
(IA)

converting a compound of formula (IA) into a compound of formula (IB); and

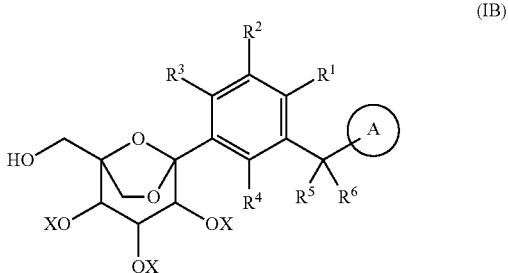
(IB)

deprotecting the compound of formula (IB) into the compound of formula (I),
wherein R1-R6 and ring A are as defined in formula (I), and X and Y are hydroxyl protecting groups, preferably alkyl or benzyl.

The present invention relates to use of the compounds of the formula (I), pharmaceutically acceptable salts thereof and stereoisomers thereof, in the preparation of a sodium-dependent glucose transporter inhibitor.

In addition, the present invention relates to use of the compounds of the formula (I), pharmaceutically acceptable salts thereof and stereoisomers thereof, in the preparation of a medicament for treating or slowing development or onset of a disease, wherein the disease is selected from the group consisting of diabetes, retinopathy, neuropathy, nephropathy, insulin resistance, hyperglycemia, hyperinsulinemia, elevated levels of fatty acids or glycerol, hyperlipidemia, obesity, hypertriglyceridemia, syndrome X, diabetic complications, atherosclerosis and hypertension.

The present invention also relates to a method for treating a disease selected from the group consisting of diabetes, retinopathy, neuropathy, nephropathy, insulin resistance, hyperglycemia, hyperinsulinemia, elevated levels of fatty acids or glycerol, hyperlipidemia, obesity, hypertriglyceridemia, syndrome X, diabetic complications, atherosclerosis and hypertension, comprising administering to a subject in need thereof a therapeutically effective amount of the compound of formula (I) or pharmaceutically acceptable salts thereof or stereoisomers thereof.

The present invention also relates to the compound of formula (I) or pharmaceutically acceptable salts thereof or stereoisomers thereof, for use as a medicament for treating or slowing development or onset of a disease, wherein the disease is selected from the group consisting of diabetes, retinopathy, neuropathy, nephropathy, insulin resistance, hyperglycemia, hyperinsulinemia, elevated levels of fatty acids or glycerol, hyperlipidemia, obesity, hypertriglyceridemia, syndrome X, diabetic complications, atherosclerosis and hypertension.

Furthermore, the present invention relates to a pharmaceutical composition comprising a therapeutically effective amount of a compound of formula (I), a pharmaceutically acceptable salt or stereoisomer thereof and a pharmaceutically acceptable carrier. And the present invention relates to use of the pharmaceutical composition in the preparation of a medicament for treating or slowing development or onset of a disease, wherein the disease is selected from the group consisting of diabetes, retinopathy, neuropathy, nephropathy, insulin resistance, hyperglycemia, hyperinsulinemia, elevated levels of fatty acids or glycerol, hyperlipidemia, obesity, hypertriglyceridemia, syndrome X, diabetic complications, atherosclerosis and hypertension.

The present invention also relates to a method for treating a disease selected from the group consisting of diabetes, retinopathy, neuropathy, nephropathy, insulin resistance, hyperglycemia, hyperinsulinemia, elevated levels of fatty acids or glycerol, hyperlipidemia, obesity, hypertriglyceridemia, syndrome X, diabetic complications, atherosclerosis and hypertension, comprising administering to the subject in need thereof a therapeutically effective amount of the pharmaceutical composition.

The present invention also relates to use of the pharmaceutical composition as a medicament for treating or slowing development or onset of a disease, wherein the disease is selected from the group consisting of diabetes, retinopathy, neuropathy, nephropathy, insulin resistance, hyperglycemia, hyperinsulinemia, elevated levels of fatty acids or glycerol, hyperlipidemia, obesity, hypertriglyceridemia, syndrome X, diabetic complications, atherosclerosis and hypertension.

DETAILED DESCRIPTION OF THE INVENTION

Unless otherwise stated, the following terms used in the specification and claims have the meanings described below.

"Alkyl" refers to a saturated aliphatic hydrocarbon group including C1-C20 straight chain and branched chain groups. Preferably an alkyl group is an alkyl having 1 to 12 carbon atoms. Representative examples include, but are not limited to methyl, ethyl, n-propyl, isopropyl, n-butyl, isobutyl, tert-butyl, sec-butyl, n-pentyl, 1,1-dimethyl propyl, 1,2-dimethyl propyl, 2,2-dimethyl propyl, 1-ethyl propyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and the isomers of branched chain thereof. More preferably an alkyl group is a lower alkyl having 1 to 6 carbon atoms. Representative examples include, but are not limited to methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl etc. The alkyl group may be substituted or unsubstituted. When substituted, the substituent group(s) is preferably one or more groups independently selected from the group consisting of alkyl, alkenyl, alkynyl, alkyxoyl, alkylsulfo, alkylamino, halogen, thiol, hydroxyl, nitro, cyanide, cycloalkyl, heterocyclic alkyl, aryl, heteroaryl, cycloalkoxyl, heterocyclic alkoxyl, cycloalkylthio, heterocylic alkylthio, oxo, —OR7, —S(O)mR7, —C(O)R7, —C(O)OR7, —NR8R9 and —C(O)NR8R9.

"Cycloalkyl" refers to a saturated and/or partially unsaturated monocyclic or polycyclic hydrocarbon group and has 3 to 20 carbon atoms. Preferably a cycloalkyl group is a cycloalkyl having 3 to 12 carbon atoms. More preferably a cycloalkyl group is a cycloalkyl having 3 to 10 carbon atoms. Representative examples of monocyclic cycloalkyl groups include, but are not limited to cyclopropyl, cyclobutyl, cyclopentyl, cyclopentenyl, cyclohexyl, cyclohexenyl, cyclohexadienyl, cycloheptyl, cycloheptatrienyl, cyclooctyl etc. Polycyclic cycloalkyl groups include the cycloalkyl having spiro ring, fused ring and bridged ring.

"Spiro Cycloalkyl" refers to a 5 to 20 membered polycyclic hydrocarbon group with rings connected through one common carbon atom (called a spiro atom), wherein one or more rings may contain one or more double bonds, but none of the rings has a completely conjugated pi-electron system. Preferably a spiro cycloalkyl is 6 to 14 membered, and more preferably is 7 to 10 membered. According to the number of the common spiro atoms between spiro rings, spiro cycloalkyl is divided into monocyclic spiro ring, bicyclic spiro ring or multicyclic spiro ring, and preferably refers to monocyclic spiro ring or bicyclic spiro ring. More preferably spiro cycloalkyl is 4-membered/4-membered, 4-membered/5-membered, 4-membered/6-membered, 5-membered/5-membered, or 5-membered/6-membered monocyclic spiro ring. Representative examples of spiro cycloalkyl include, but are not limited to the following groups:

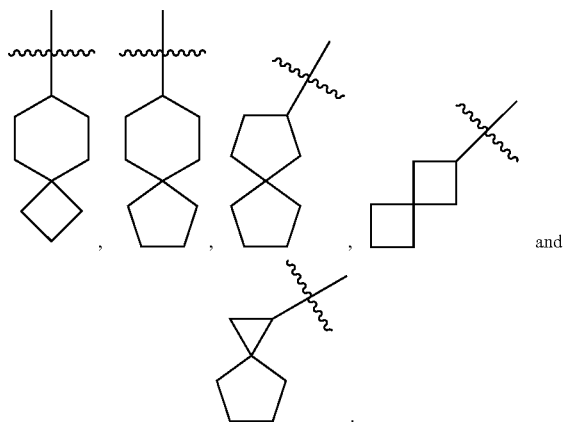

"Fused Cycloalkyl" refers to a 5 to 20 membered polycyclic hydrocarbon group, wherein each ring in the system shares an adjacent pair of carbon atoms with other ring, wherein one or more rings may contain one or more double bonds, but none of the rings has a completely conjugated pi-electron system. Preferably a fused cycloalkyl group is 6 to 14 membered, and more preferably is 7 to 10 membered. According to the number of membered rings, fused cycloalkyl is divided into fused bicyclic ring, tricyclic ring, tetracyclic ring or multicyclic ring, preferably fused bicyclic ring or tricyclic ring. More preferably fused cycloalkyl is 5-membered/5-membered, or 5-membered/6-membered fused bicyclic ring. Representative examples of fused cycloalkyl include, but are not limited to the following groups:

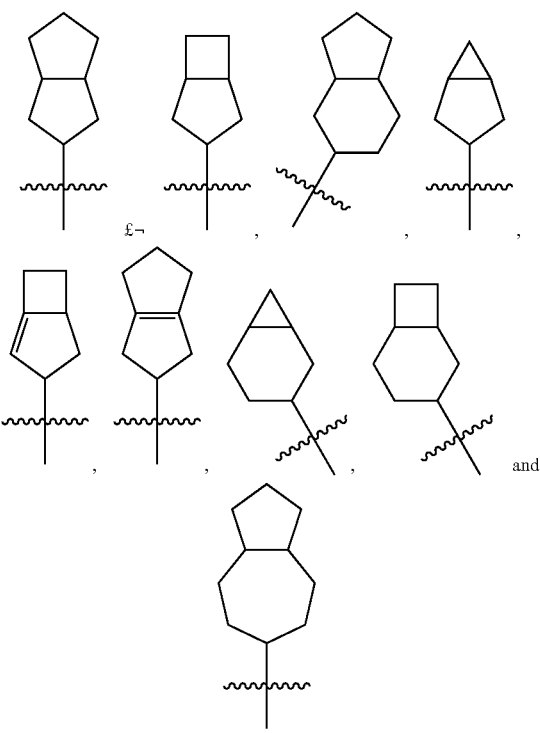

"Bridged Cycloalkyl" refers to a 5 to 20 membered polycyclic hydrocarbon group, wherein every two rings in the system share with two disconnected carbon atoms. The said rings could have one or more double bonds but have no completely conjugated pi-electron system. Preferably a bridged cycloalkyl is 6 to 14 membered, and more preferably is 7 to 10 membered. According to the number of membered rings, bridged cycloalkyl is divided into bridged bicyclic ring, tricyclic ring, tetracyclic ring or multicyclic ring, preferably bicyclic ring, tricyclic ring or tetracyclic ring bridged cycloalkyl, and more preferably bicyclic ring or tricyclic ring bridged cycloalkyl. Representative examples of bridged cycloalkyl include, but are not limited to the following groups:

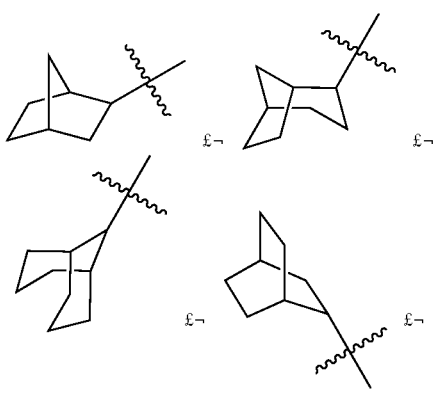

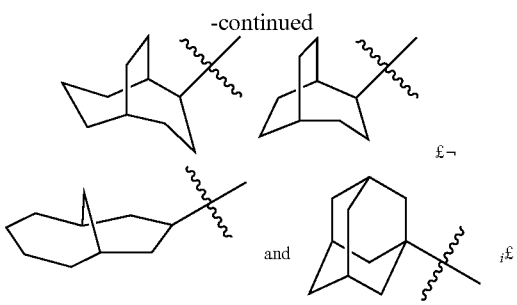

The said cycloalkyl can be fused to aryl, heteroaryl or heterocyclic alkyl, wherein the ring connected with the parent structure is cycloalkyl. Representative examples of bridged cycloalkyl include, but are not limited to indanylacetic, tetrahydronaphthalene, benzocycloheptyl and so on. Said cycloalkyl may be substituted or unsubstituted. When substituted, the substituent group(s) is preferably one or more groups independently selected from the group consisting of alkyl, alkenyl, alkynyl, alkoxyl, thioalkyl, alkylamino, halogen, thiol, hydroxyl, nitro, cyano, cycloalkyl, heterocyclic alkyl, aryl, heteroaryl, cycloalkoxyl, heterocylic alkoxyl, cycloalkylthio, heterocylic alkylthio, oxo, —OR7, —S(O)mR7, —C(O)R7, —C(O)OR7, —NR8R9 and —C(O) NR8R9.

"Alkenyl" refers to an alkyl defined as above that has at least two carbon atoms and at least one carbon-carbon double bond. For example, it refers to vinyl, 1-propenyl, 2-propenyl, 1-, 2- or 3-butenyl etc. The alkenyl group may be substituted or unsubstituted. When substituted, the substituent group(s) is preferably one or more independently selected from the group consisting of alkyl, alkenyl, alkynyl, alkoxyl, thioalkyl, alkylamino, halogen, thiol, hydroxyl, nitro, cyano, cycloalkyl, heterocyclic alkyl, aryl, heteroaryl, cycloalkoxyl, heterocylic alkoxyl, cycloalkylthio, heterocylic alkylthio, oxo, —OR7, —S(O)mR7, —C(O)R7, —C(O)OR7, —NR8R9 and —C(O)NR8R9.

"Alkynyl" refers to an alkyl defined as above that has at least two carbon atoms and at least one carbon-carbon triple bond. For example, it refers to ethynyl, 1-propynyl, 2-propynyl, 1-, 2- or 3-butynyl etc. The alkynyl group may be substituted or unsubstituted. When substituted, the substituent group(s) is preferably one or more independently selected from the group consisting of alkyl, alkenyl, alkynyl, alkoxyl, thioalkyl, alkylamino, halogen, thiol, hydroxyl, nitro, cyano, cycloalkyl, heterocyclic alkyl, aryl, heteroaryl, cycloalkoxyl, heterocylic alkoxyl, cycloalkylthio, heterocylic alkylthio, oxo, —OR7, —S(O)mR7, —C(O)R7, —C(O)OR7, —NR8R9 and —C(O)NR8R9.

"Heterocyclic alkyl" refers to a 3 to 20 membered saturated and/or partially unsaturated monocyclic or polycyclic hydrocarbon group having one or more heteroatoms selected from the group consisting of N, O and $S(O)_m$ (wherein m is 0, 1 or 2) as ring atoms, but excluding —O—O—, —O—S— or —S—S— in the ring, the remaining ring atoms being C. Preferably, heterocyclic alkyl is 3 to 12 membered having 1 to 4 said heteroatoms; more preferably, is 3 to 10 membered. Representative examples of monocyclic heterocyclic alkyl include, but are not limited to pyrrolidyl, piperidyl, piperazinyl, morpholinyl, sulfo-morpholinyl, homopiperazinyl and so on. Polycyclic heterocyclic alkyl includes heterocyclic alkyl having spiro ring, fused ring and bridged ring. "Spiro Heterocyclo alkyl" refers to a 5 to 20 membered polycyclic heterocyclic alkyl group with rings connected through one common carbon atom (called a spiro atom), wherein said rings have one or more heteroatoms selected from the group consisting of N, O and S(O)p (wherein p is 0, 1 or 2) as ring atoms, the remaining ring atoms being C, wherein one or more rings may contain one or more double bonds, but none of the rings has a completely conjugated pi-electron system. Preferably a spiro heterocyclic alkyl is 6 to 14 membered, more preferably is 7 to 10 membered. According to the number of common atoms, spiro heterocyclic alkyl is divided into monocyclic spiro heterocyclic alkyl, bicyclic spiro heterocyclic alkyl or multicyclic spiro heterocyclo alkyl, preferably monocyclic spiro heterocyclic alkyl or bicyclic sipro heterocyclo alkyl. More preferably spiro heterocyclic alkyl is 4-membered/4-membered, 4-membered/5-membered, 4-membered/6-membered, 5-membered/5-membered, or 5-membered/6-membered monocyclic spiro heterocyclo alkyl. Representative examples of spiro heterocyclic alkyl include, but are not limited to the following groups:

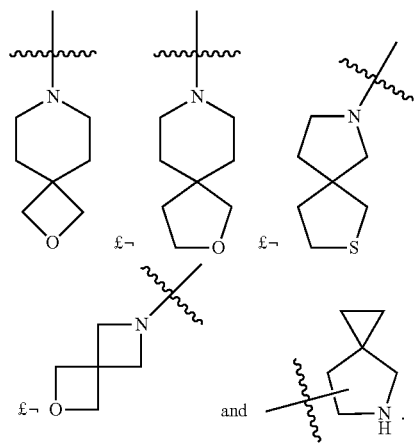

"Fused Heterocyclic alkyl" refers to a 5 to 20 membered polycyclic heterocyclic alkyl group, wherein each ring in the system shares an adjacent pair of carbon atoms with another ring, wherein one or more rings may contain one or more double bonds, but none of the rings has a completely conjugated pi-electron system, and wherein said rings have one or more heteroatoms selected from the group consisting of N, O and S(O)p (wherein p is 0, 1 or 2) as ring atoms, the remaining ring atoms being C. Preferably a fused heterocyclic alkyl is 6 to 14 membered, more preferably is 7 to 10 membered. According to the number of membered rings, fused heterocyclic alkyl is divided into fused bicyclic ring, tricyclic ring, tetracyclic ring or multicyclic ring, preferably fused bicyclic ring or tricyclic ring. More preferably fused heterocyclic alkyl is 5-membered/5-membered, or 5-membered/6-membered fused bicyclic ring. Representative examples of fused heterocyclic alkyl include, but are not limited to the following groups:

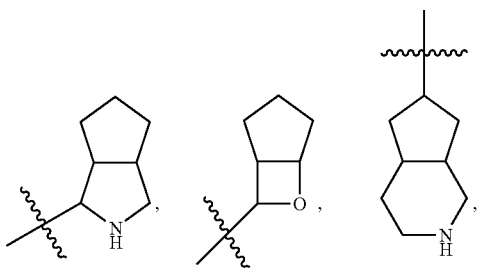

-continued

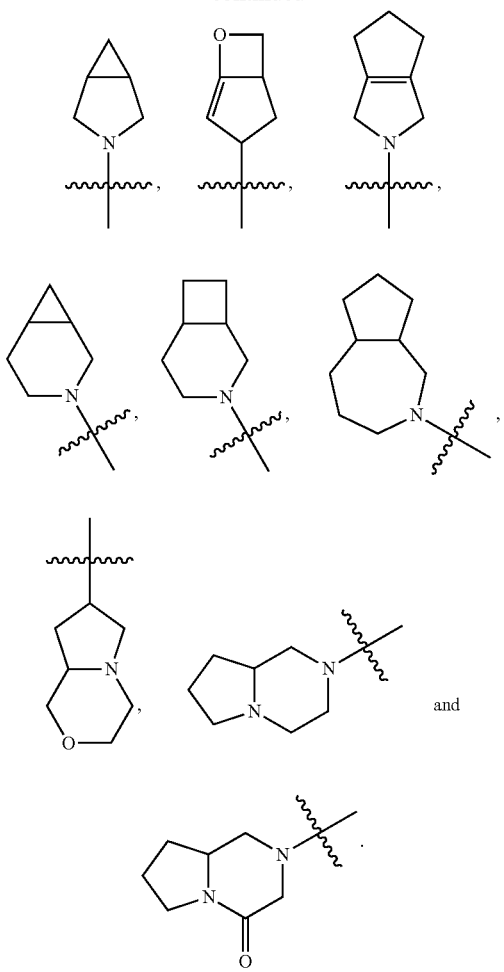

"Bridged Heterocyclic alkyl" refers to a 5 to 14 membered polycyclic heterocyclic alkyl group, wherein every two rings in the system share with two disconnected carbon atoms, said rings could have one or more double bonds but have no completely conjugated pi-electron system, and said rings have one or more heteroatoms selected from the group consisting of N, O and S(O)m (wherein m is 0, 1 or 2) as ring atoms, the remaining ring atoms being C. Preferably a bridged heterocyclic alkyl is 6 to 14 membered, more preferably 7 to 10 membered. According to the number of membered rings, bridged heterocyclic alkyl is divided into bridged bicyclic ring, tricyclic ring, tetracyclic ring or multicyclic ring, preferably bicyclic ring, tricyclic ring or tetracyclic ring bridged heterocyclic alkyl, more preferably bicyclic ring or tricyclic ring bridged heterocyclic alkyl. Representative examples of bridged heterocyclic alkyl include, but are not limited to the following groups:

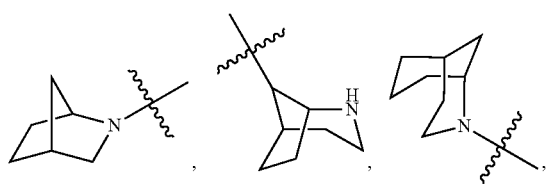

-continued

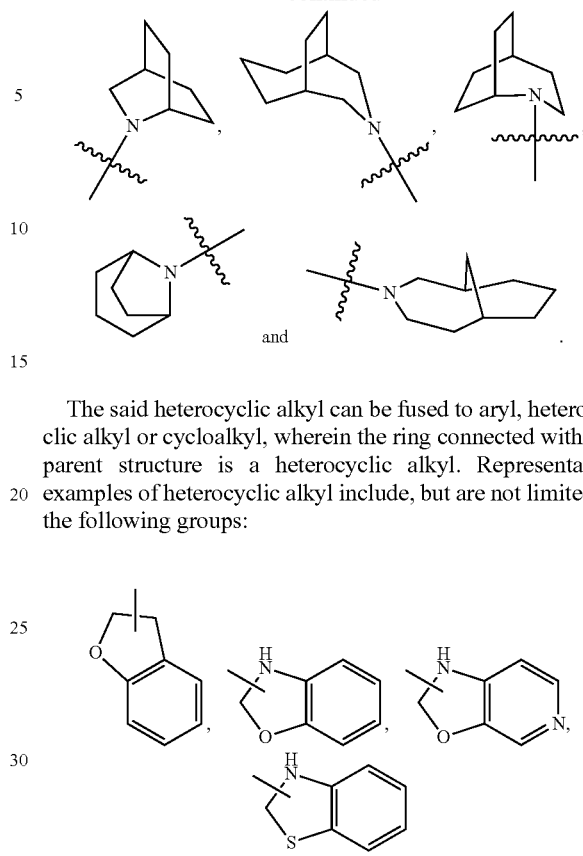

and

The said heterocyclic alkyl can be fused to aryl, heterocyclic alkyl or cycloalkyl, wherein the ring connected with the parent structure is a heterocyclic alkyl. Representative examples of heterocyclic alkyl include, but are not limited to the following groups:

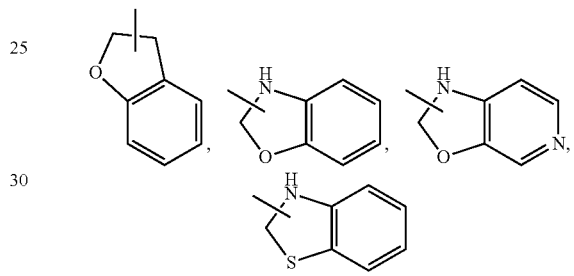

and so on. The heterocyclic alkyl may be substituted or unsubstituted. When substituted, the substituent group(s) is preferably one or more groups independently selected from the group consisting of alkyl, alkenyl, alkynyl, alkoxyl, thioalkyl, alkylamino, halogen, thiol, hydroxyl, nitro, cyano, cycloalkyl, heterocyclic alkyl, aryl, heteroaryl, cycloalkoxyl, heterocyclic alkoxyl, cycloalkylthio, heterocyclic alkylthio, oxo, —OR7, —S(O)mR7, —C(O)R7, —C(O)OR7, —NR8R9 and —C(O)NR8R9.

"Aryl" refers to a 6 to 14 membered all-carbon monocyclic ring or multicyclic fused ring (a "fused" ring system means that each ring in the system shares an adjacent pair of carbon atoms with another ring in the system) group, and has a completely conjugated pi-electron system. Preferably aryl is 6 to 10 membered, such as phenyl and naphthyl. Said aryl can be fused to heteroaryl, heterocyclic alkyl or cycloalkyl, wherein the ring connected with the parent structure is aryl. Representative examples of aryl include, but are not limited to the following groups:

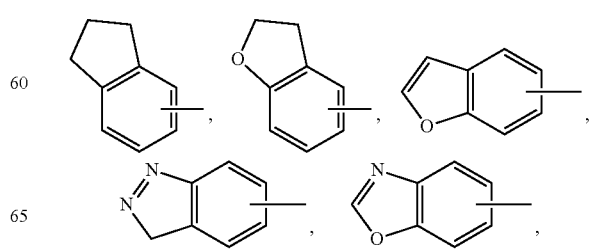

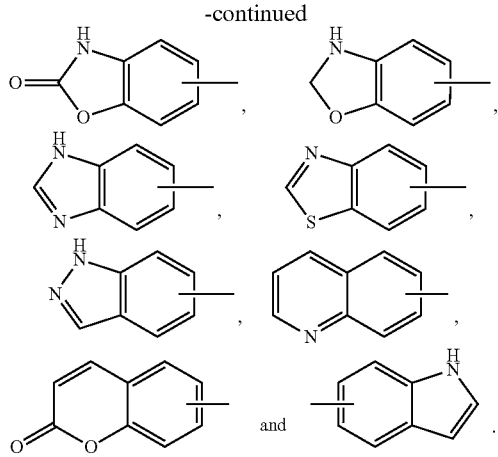

The aryl group may be substituted or unsubstituted. When substituted, the substituent group(s) is preferably one or more groups independently selected from the group consisting of alkyl, alkenyl, alkynyl, alkoxyl, thioalkyl, alkylamino, halogen, thiol, hydroxyl, nitro, cycloalkyl, heterocyclic alkyl, aryl, heteroaryl, cycloalkoxyl, heterocylic alkoxyl, cycloalkylthio, heterocylic alkylthio, oxo, —OR7, —S(O)mR7, —C(O)R7, —C(O)OR7, —NR8R9 and —C(O)NR8R9.

"Heteroaryl" refers to an aryl having 1 to 4 heteroatoms selected from the group consisting of N, O and S as ring atoms and have 5 to 14 annular atoms, preferably 5- to 10-membered ring, more preferably 5- or 6-membered ring. The examples of heteroaryl groups include furyl, thienyl, pyridyl, pyrrolyl, N-alkyl pyrrolyl, pyrimidinyl, pyrazinyl, imidazolyl, and the like. Said heteroaryl can be fused with the ring of aryl, heterocylic group or cycloalkyl, wherein the ring connected with the parent structure is heteroaryl. Representative examples include, but are not limited to the following groups:

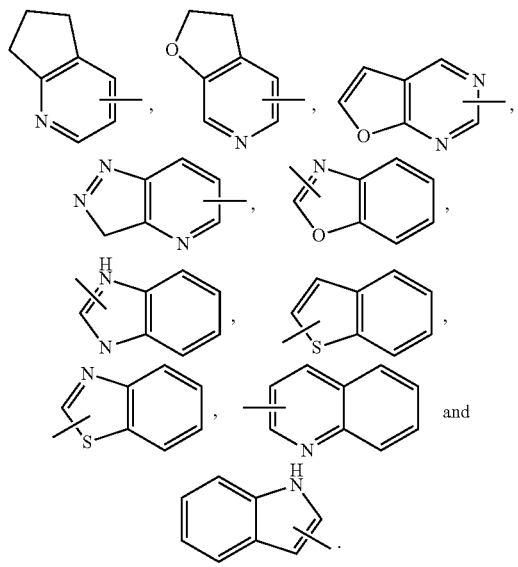

The heteroaryl group may be substituted or unsubstituted. When substituted, the substituent group(s) is preferably one or more groups independently selected from the group consisting of alkyl, alkenyl, alkynyl, alkoxyl, thioalkyl, alkylamino, halogen, thiol, hydroxyl, nitro, cyano, cycloalkyl, heterocyclic alkyl, aryl, heteroaryl, cycloalkoxyl, heterocylic alkoxyl, cycloalkylthio, heterocylic alkylthio, oxo, —OR7, —S(O)mR7, —C(O)R7, —C(O)OR7, —NR8R9 and —C(O)NR8R9.

"Alkoxyl" refers to —O-(alkyl) group, wherein the alkyl is defined as above. Representative examples include, but are not limited to, methoxy, ethoxy, propoxy, butoxy, and the like. The alkoxyl may be substituted or unsubstituted. When substituted, the substituent is preferably one or more groups independently selected from the group consisting of alkyl, alkenyl, alkynyl, alkoxyl, thioalkyl, alkylamino, halogen, thiol, hydroxyl, nitro, cyano, cycloalkyl, heterocyclic alkyl, aryl, heteroaryl, cycloalkoxyl, heterocylic alkoxyl, cycloalkylthio, heterocylic alkylthio, oxo, —OR7, —S(O)mR7, —C(O)R7, —C(O)OR7, —NR8R9 or —C(O)NR8R9.

"Cycloalkoxy" refers to an —O-(cycloalkyl) group, wherein the cycloalkyl is defined as above. Representative examples include, but are not limited to, cyclopropyloxy, cyclobutyloxy, cyclopentyloxy, cyclohexyloxy, and the like. The cycloalkoxy may be substituted or unsubstituted. When substituted, the substituent is preferably one or more groups independently selected from the group consisting of alkyl, alkenyl, alkynyl, alkoxyl, thioalkyl, alkylamino, halogen, thiol, hydroxyl, nitro, cyano, cycloalkyl, heterocyclic alkyl, aryl, heteroaryl, cycloalkoxy, heterocylic alkoxyl, cycloalkylthio, heterocylic alkylthio, oxo, —OR7, —S(O)mR7, —C(O)R7, —C(O)OR7, —NR8R9 or —C(O)NR8R9.

"Hydroxy" refers to an —OH group.
"Halogen" refers to fluoro, chloro, bromo or iodo.
"Amino" refers to a —NH2 group.
"Cyano" refers to —CN group.
"Nitro" refers to —NO2 group.
"Benzyl" refers to —CH2-phenyl group.
"Oxo" refers to =O group.
"Carboxylic acid" refers to —C(O)OH group.
"Carboxylic ester" refers to —C(O)O(alkyl) or (cycloalkyl) group.
"Thienyl" refers to

group.

"Optional" or "optionally" means that the subsequently described event or circumstance may or may not occur, and that the description includes instances where the event or circumstance may or may not occur. For example, "heterocycle group optionally substituted by an alkyl group" means that the alkyl may or may not be present, and the description includes situations where the heterocycle group is substituted by an alkyl group and situations where the heterocycle group is not substituted by the alkyl group.

"Substituted" refers to when one or more hydrogen atoms of the group, preferably 5 for maximum, more preferably 1-3, are independently replaced by the corresponding number of substituents. Absolutely, substituents are in their only possible chemical position. Technicians in the field are able to determine (experimentally or theoretically) possible or impossible substituents without paying excessive efforts. For example, it is unstable when bonding an amino group or hydroxyl group having free hydrogen with carbon atoms having an unsaturated bond (such as olefinic).

A "pharmaceutical composition" refers to a mixture of one or more of the compounds described herein, or physiologically/pharmaceutically acceptable salts or prodrugs thereof, with other chemical components, such as physiologically/ pharmaceutically acceptable carriers and excipients. The purpose of the pharmaceutical composition is to facilitate administration of a compound to an organism, with the benefit of intaking the active ingredient more effectively.

The conditions, diseases and maladies collectively referred to as "Syndrome X" (also known as metabolic syndrome) are detailed in Johannsson, J. Clin. Endocrinol. Metab., 1997; 82, 727-734 incorporated herein by reference.

m and R7-R9 are as defined in formula (I).

Specific Implementation Methods

In order to complete the purpose of the invention, the invention applies the following technical solution:

A process for preparing a compound of formula (I) or a pharmaceutically acceptable salt or stereoisomer thereof according to the present invention comprises the following steps of:

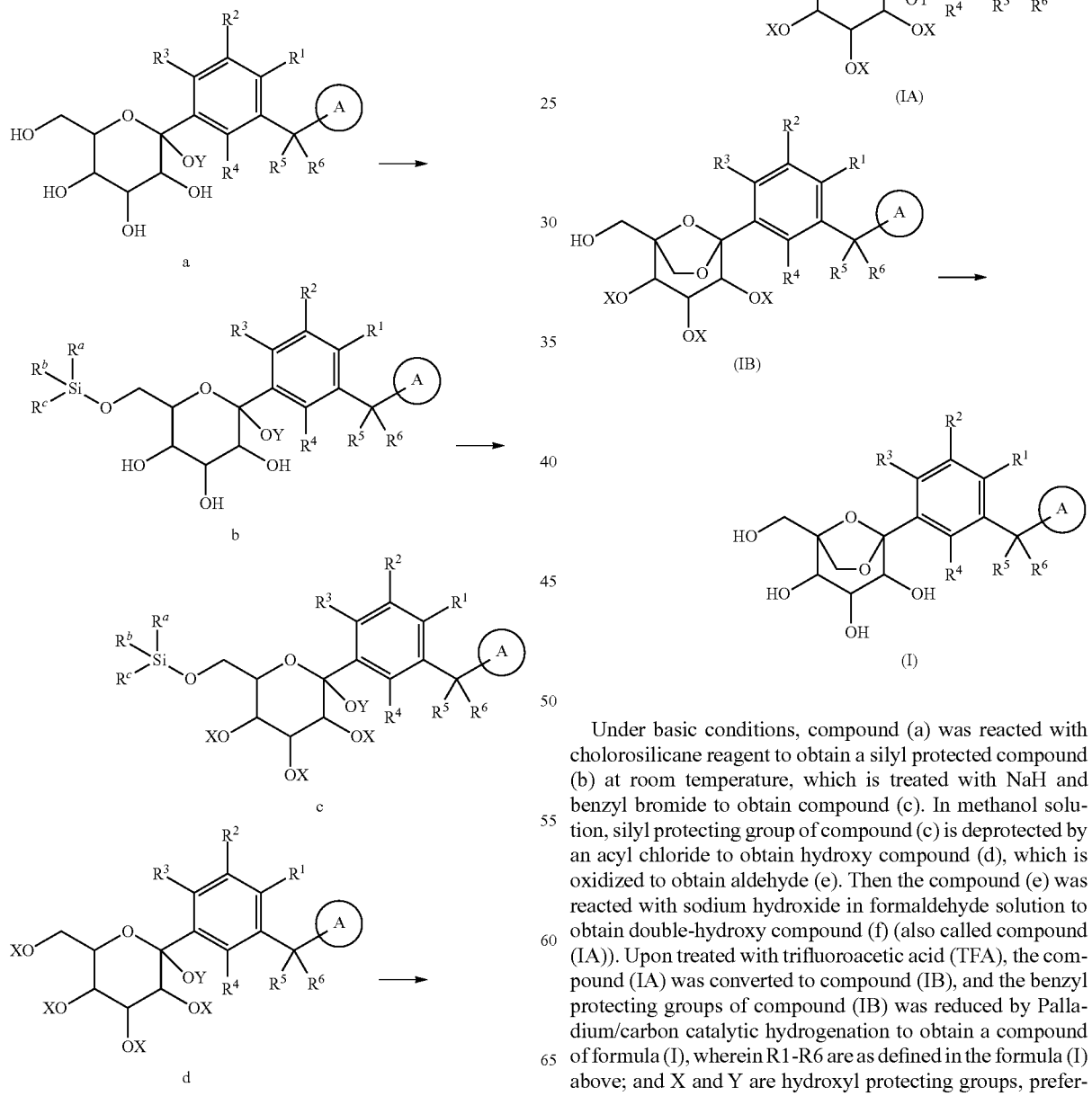

Under basic conditions, compound (a) was reacted with cholorosilicane reagent to obtain a silyl protected compound (b) at room temperature, which is treated with NaH and benzyl bromide to obtain compound (c). In methanol solution, silyl protecting group of compound (c) is deprotected by an acyl chloride to obtain hydroxy compound (d), which is oxidized to obtain aldehyde (e). Then the compound (e) was reacted with sodium hydroxide in formaldehyde solution to obtain double-hydroxy compound (f) (also called compound (IA)). Upon treated with trifluoroacetic acid (TFA), the compound (IA) was converted to compound (IB), and the benzyl protecting groups of compound (IB) was reduced by Palladium/carbon catalytic hydrogenation to obtain a compound of formula (I), wherein R1-R6 are as defined in the formula (I) above; and X and Y are hydroxyl protecting groups, preferably alkyl or benzyl group.

EXAMPLES

The present invention is further described by the following examples which are not intended to limit the scope of the invention.

The structures of all compounds were identified by nuclear magnetic resonance (1H NMR) and/or mass spectrometry (MS). 1H NMR chemical shifts were recorded as ppm (10-6). 1H NMR was performed on a Bruker AVANCE-400 spectrometer. The appropriate solvents included deuterated-methanol (CD3OD), deuterated-chloroform (CDCl3) and deuterated-dimethyl sulfoxide (DMSO-d6) with tetramethylsilane (TMS) as the internal standard.

MS was determined on FINNIGAN LCQ Ad (ESI) mass spectrometer (Thermo, Model: Finnigan LCQ advantage MAX).

HPLC was determined on Agilent 1200DAD high pressure liquid chromatography spectrometer (Sunfire C18 150×4.6 mm chromatographic column) and Waters 2695-2996 high pressure liquid chromatography spectrometer (Gimini C18 150×4.6 mm chromatographic column).

The thin-layer silica gel used was Yantai Huanghai HSGF254 or Qingdao GF254 silica gel plate. The dimension of the plates used in TLC was 0.15 mm to 0.2 mm, and the dimension of the plates used in product purification was 0.4 mm to 0.5 mm.

Column chromatography generally used was Yantai Huangha 200 to 300 mesh silica gel as carrier.

The starting materials of the present invention were known or purchased from ABCR GmbH & Co. KG, Acros Organics, Aldrich Chemical Company, Accela ChemBio Inc, Darui Finechemical Co., Ltd and so on, or they could be prepared by the conventional synthesis methods in the prior art.

The term "argon atmosphere" or "nitrogen atmosphere" refers to such an atmosphere that a reaction flask was equipped with a balloon filled with about 1 L argon or nitrogen.

The term "hydrogen atmosphere" refers to that a reaction flask was equipped with a balloon filled with about 1 L hydrogen.

Pressured hydrogenation reactions were performed with Parr 3916EKX hydrogenation spectrometer and QL-500 hydrogen generator or HC2-SS hydrogenation spectrometer.

In hydrogenation reactions, the reaction system was generally vacuumed and filled with hydrogen; while repeated the above operation three times.

The microwave reaction was carried out in CEM Discover-S-908860-type microwave reactor.

Unless otherwise stated, the reaction was carried out in a nitrogen or argon atmosphere.

Unless otherwise stated, the solution used in examples refers to an aqueous solution.

Unless otherwise stated, the reaction temperature was room temperature.

Room temperature was the most ambient reaction temperature, which was 20° C.-30° C.

The reaction process in the examples was monitored by thin layer chromatography (TLC). The developing solvent system comprises dichloromethane and methanol system, hexane and ethyl acetate system, petroleum ether and ethyl acetate system, and acetone. The ratio of the volume of the solvent was adjusted according to the polarity of the compounds.

The elution system of column chromatography and the developing solvent system of thin layer chromatography comprises: A: dichloromethane and methanol system, B: n-hexane and ethyl acetate system, C: dichloromethane and acetone system. The ratio of the volume of the solvent was adjusted according to the polarity of the compounds, and sometimes it was also adjusted by adding a basic agent such as triethylamine or an acidic agent such as acetic acid.

Example 1

(1S,2S,3S,4R,5S)-5-[4-chloro-3-[[4-[2-(cyclopropoxy)ethoxy]phenyl]methyl]phenyl]-1-(hydroxymethyl)-6,8-dioxabicyclo[3.2.1]octane-2,3,4-triol

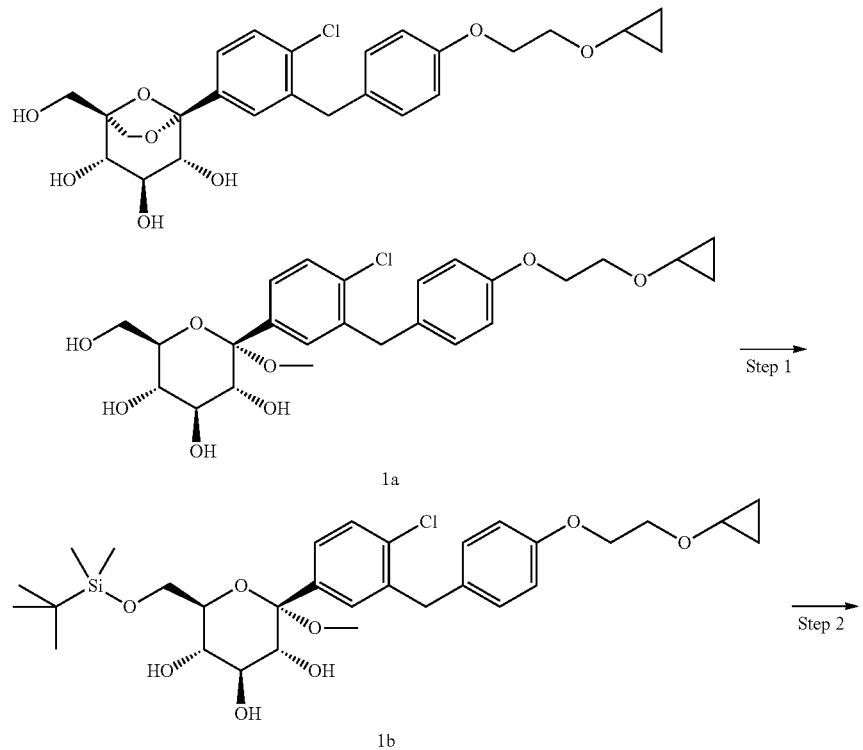

-continued
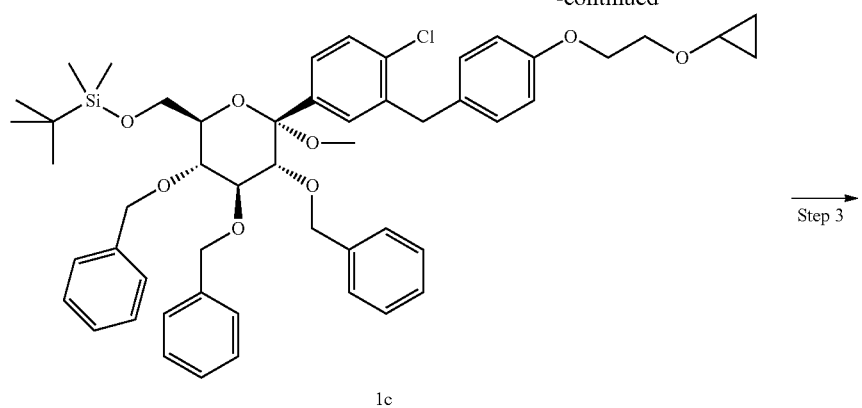
1c
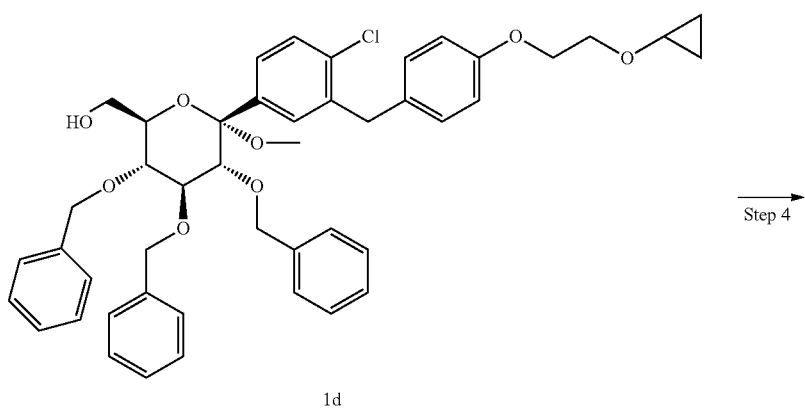
1d
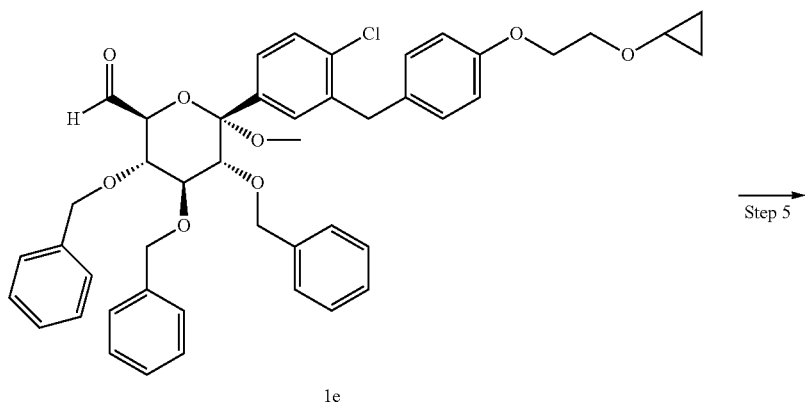
1e
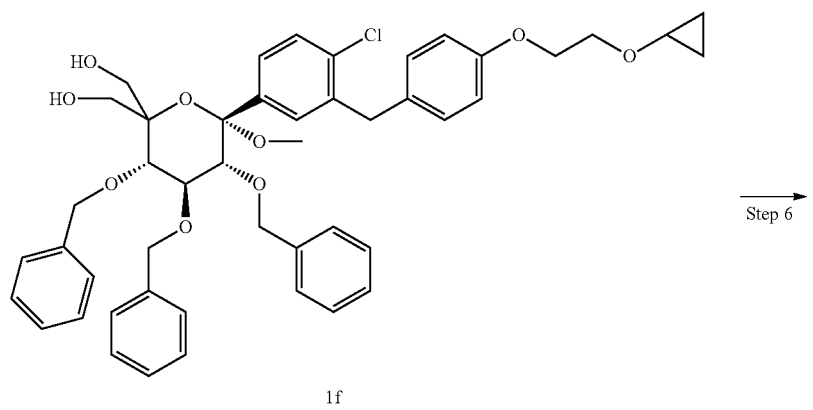
1f

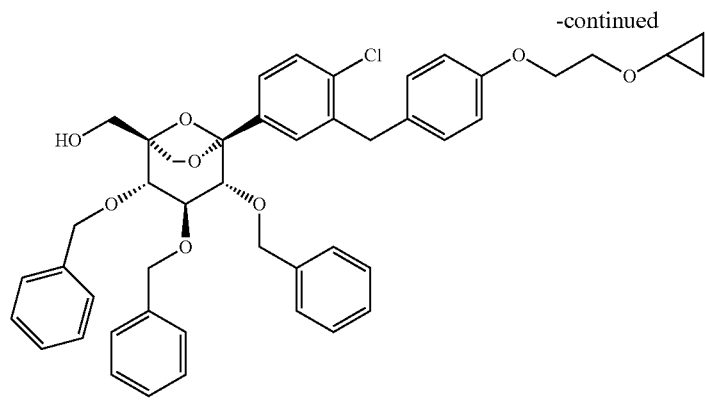

1g

Step 7

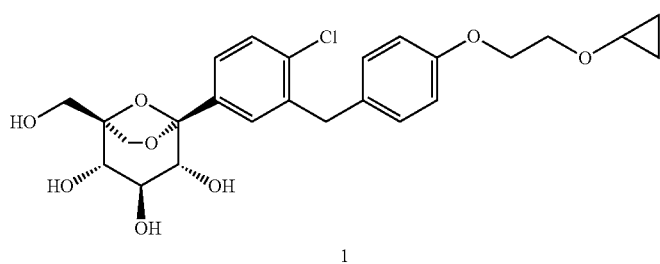

1

Step 1

(2S,3R,4S,5S,6R)-6-[(tert-butyl(dimethyl)silyl)
oxymethyl]-2-[4-chloro-3-[[4-[2-(cyclopropoxy)
ethoxy]phenyl]methyl]phenyl]-2-methoxy-tetrahydropyran-3,4,5-triol (2S,3R,4S,5S,6R)-2-[4-chloro-3-[[4-[2-(cyclopropoxy)ethoxy]phenyl]methyl]phenyl]-6-(hydroxymethyl)-2-methoxy-tetrahydropyran-3,4,5-triol 1a (Prepared according to the method in WO2010022313) (3.0 g, 6.06 mmol) was dissolved in 20 mL pyridine, followed by addition of 4-dimethylamino pyridine (148 mg, 1.21 mmol) and TBSCl (1.1 g, 7.27 mmol) in turn. The reaction mixture was stirred for 16 hours, then concentrated under reduced pressure. The residue was dissolved in 100 mL ethyl acetate and 100 mL water and partitioned. The aqueous phase was extracted with ethyl acetate (100 mL), and the organic layer was washed with water (50 mL), combined, dried over anhydrous magnesium sulfate, filtered and concentrated under reduced pressure. The resulting residue was purified by silica gel chromatography with elution system A to obtain the title compound (2S,3R,4S,5S,6R)-6-[(tert-butyl(dimethyl)silyl)oxymethyl]-2-[4-chloro-3-[[4-[2-(cyclopropoxy)ethoxy]phenyl]methyl]phenyl]-2-methoxy-tetrahydropyran-3,4,5-triol 1b (3.0 g, yellow solid), yield: 81.1%. 1H NMR (400 MHz, CD3OD): δ 7.50 (dd, 1H), 7.38 (m, 2H), 7.08 (d, 2H), 6.82 (d, 2H), 4.04 (m, 5H), 3.88 (m, 1H¬), 3.82 (m, 2H), 3.75 (m, 1H), 3.59 (m, 1H), 3.40 (m, 2H), 3.07 (m, 1H), 3.06 (s, 3H), 0.90 (s, 9H), 0.53 (m, 4H), 0.10 (s, 3H), 0.07 (s, 3H).

Step 2

[[(2R,3R,4S,5R,6S)-3,4,5-tribenzyloxy-6-[4-chloro-3-[[4-[2-(cyclopropoxy)ethoxy]phenyl]methyl]phenyl]-6-methoxy-tetrahydropyran-2-yl]methoxy]tert-butyl-dimethyl-silane (2S,3R,4S,5S,6R)-6-[(tert-butyl(dimethyl)silyl)oxymethyl]-2-[4-chloro-3-[[4-[2-(cyclopropoxy)ethoxy]phenyl]methyl]phenyl]-2-methoxy-tetrahydropyran-3,4,5-triol 1b (3.0 g, 4.92 mmol) was dissolved in 50 mL N,N-dimethyl formamide and cooled to 0° C. 60% NaH (984 mg, 24.6 mmol) was added. Then the reaction mixture was warmed to room temperature and stirred for 15 minutes before benzyl bromide (2.95 mL, 24.6 mmol) was added. The mixture was stirred for 16 hours. The reaction mixture was concentrated under reduced pressure after 5 mL methanol were added. The residue was dissolved in 100 mL ethyl acetate and partitioned. The organic extracts were washed with water (50 mL×2) and combined, dried over anhydrous magnesium sulfate, filtered and concentrated under reduced pressure obtain the crude title compound [[(2R,3R,4S,5R,6S)-3,4,5-tribenzyloxy-6-[4-chloro-3-[[4-[2-(cyclopropoxy)ethoxy]phenyl]methyl]phenyl]-6-methoxy-tetrahydropyran-2-yl]methoxy]-tert-butyl-dim-ethyl-silane 1c (4.26 g, yellow grease), which was used directly without purification in the next step.

Step 3

[(2R,3R,4S,5R,6S)-3,4,5-tribenzyloxy-6-[4-chloro-3-[[4-[2-(cyclopropoxy)ethoxy]phenyl]methyl]phenyl]-6-methoxy-tetrahydropyran-2-yl]methanol Crude [[(2R,3R,4S,5R,6S)-3,4,5-tribenzyloxy-6-[4-chloro-3-[[4-[2-(cyclopropoxy)ethoxy]phenyl]methyl]phenyl]-6-methoxy-tetrahydropyran-2-yl]methoxy]tert-butyl-dimethyl-silane 1c (4.26 g, 4.92 mmol) was dissolved in 30 mL methanol, followed by addition of acetyl chloride (52 μL, 0.74 mmol). The reaction mixture was stirred for 1 hour. The reaction mixture was concentrated under reduced pressure and purified by silica gel chromatography with elution system B to obtain the title compound [(2R,3R,4S,5R,6S)-3,4,5-tribenzyloxy-6-[4-chloro-3-[[4-[2-(cyclopropoxy)ethoxy]phenyl]methyl]phenyl]-6-methoxy-tetrahydropyran-2-yl] methanol 1d (2.3 g, yellow grease), yield: 62.2%. 1H NMR (400 MHz, CDCl$_3$): δ 7.35 (m, 13H), 7.20 (m, 3H), 7.03 (m, 4H), 6.80 (d, 2H), 4.92 (m, 3H), 4.70 (m, 1H), 4.50 (m, 1H), 4.17 (m, 1H), 4.05 (m, 3H), 3.85 (m, 6H), 3.70 (m, 2H), 3.40 (m, 1H), 3.30 (m, 1H), 3.07 (s, 3H), 0.63 (m, 2H), 0.48 (m, 2H).

Step 4

(2S,3S,4S,5R,6S)-3,4,5-tribenzyloxy-6-[4-chloro-3-[[4-[2-(cyclopropoxy)ethoxy]phenyl]methyl]phenyl]-6-methoxy-tetrahydropyran-2-carbaldehyde Oxalyl chloride (0.19 mL, 2.2 mmol) was dissolved in 10 mL methylene chloride, cooled to −78° C., followed by dropwise addition of 5 mL of a solution of dimethylsulfoxide in methylene chloride and 10 mL [(2R,3R,4S,5R,6S)-3,4,5-tribenzyloxy-6-[4-chloro-3-[[4-[2-(cyclopropoxy)ethoxy]phenyl]methyl]phenyl]-6-methoxy-tetrahydropyran-2-yl] methanol 1d (1.3 g, 1.7 mmol) in methylene chloride. The mixture was stirred for 30 minutes at −78° C. Thereafter, the mixture was warmed to room temperature and stirred for 1-2 hours after triethylamine (1.18 mL, 8.5 mmol) was added. The reaction mixture was partitioned after 10 mL, 1 M hydrochloric acid were added. The organic phase was washed with saturated sodium chloride solution (10 mL×2), combined, dried over anhydrous magnesium sulfate, and filtered. The filtrate was concentrated under reduced pressure to obtain the crude title compound (2S,3S,4S,5R,6S)-3,4,5-tribenzyloxy-6-[4-chloro-3-[[4-[2-(cyclopropoxy)ethoxy]phenyl]methyl]phenyl]-6-methoxy-tetrahydropyran-2-carbaldehyde 1e (1.3 g, colorless oil), which was used directly without purification in the next step. MS m/z (ESI): 780.3 [M+18].

Step 5

[(3S,4S,5R,6S)-3,4,5-tribenzyloxy-6-[4-chloro-3-[[4-[2-(cyclopropoxy)ethoxy]phenyl]methyl]phenyl]-2-(hydroxymethyl)-6-methoxy-tetrahydropyran-2-yl]methanol Crude (2S,3S,4S,5R,6S)-3,4,5-tribenzyloxy-6-[4-chloro-3-[[4-[2-(cyclopropoxy)ethoxy]phenyl]methyl]phenyl]-6-methoxy-tetrahydropyran-2-carbaldehyde 1e (1.3 g, 1.7 mmol) was dissolved in 15 mL 1,4-dioxane, followed by addition of 37% formaldehyde solution (2.6 mL, 34 mmol) and a solution of sodium hydroxide (204 mg, 5.1 mmol) in 5.1 mL water into the reaction mixture. The reaction mixture was stirred for 4 hours at 70° C., then cooled to 50° C. and stirred for 16 hours. The reaction mixture was extracted with ethyl acetate (20 mL×3) after 20 mL saturated sodium chloride solution were added. The organic extract was washed with saturated sodium bicarbonate solution (20 mL), saturated sodium chloride solution (20 mL), combined, dried over anhydrous magnesium sulfate, and filtered. The filtrate was concentrated under reduced pressure. Then 20 mL of mixed solution (THF and MeOH, v:v=1:1) were added into the residue, before sodium borohydride (130 mg, 3.4 mmol) was added. The reaction mixture was stirred for 30 minutes and concentrated under reduced pressure. The residue was dissolved in ethyl acetate (50 mL) and partitioned. The organic extract was washed with saturated sodium chloride solution (10 mL×2), combined, dried over anhydrous magnesium sulfate, and filtered. The filtrate was concentrated under reduced pressure, then the resulting residue was purified by silica gel chromatography with elution system B to obtain the title compound [(3S,4S,5R,6S)-3,4,5-tribenzyloxy-6-[4-chloro-3-[[4-[2-(cyclopropoxy)ethoxy]phenyl]methyl]phenyl]-2-(hydroxymethyl)-6-methoxy-tetrahydropyran-2-yl]methanol 1f (320 mg, colorless oil), yield: 23.7%.

Step 6

[(1S,2S,3S,4R,5S)-2,3,4-tribenzyloxy-5-[4-chloro-3-[[4-[2-(cyclopropoxy)ethoxy]phenyl]methyl]phenyl]-6,8-dioxabicyclo[3.2.1]octan-1-yl]methanol

[(3S,4S,5R,6S)-3,4,5-tribenzyloxy-6-[4-chloro-3-[[4-[2-(cyclopropoxy)ethoxy]phenyl]methyl]phenyl]-2-(hydroxymethyl)-6-methoxy-tetrahydropyran-2-yl]methanol 1f (320 mg, 0.4 mmol) was dissolved in 10 mL methylene chloride and cooled to −10° C., followed by addition of trifluoroacetic acid (62 mL, 0.8 mmol). The mixture was stirred for 1 hour. Thereafter, the reaction mixture was partitioned after 10 mL saturated sodium bicarbonate solution were added. The aqueous phase was extracted with dichlormethane (10 mL) and the organic extract was washed with saturated sodium chloride solution (10 mL), combined, dried over anhydrous magnesium sulfate, and filtered. The filtrate was concentrated under reduced pressure and the resulting residue was purified by silica gel chromatography with elution system B to obtain the title compound [(1S,2S,3S,4R,5S)-2,3,4-tribenzyloxy-5-[4-chloro-3-[[4-[2-(cyclopropoxy)ethoxy]phenyl]methyl]phenyl]-6,8-dioxabicyclo[3.2.1]octan-1-yl]methanol 1g (230 mg, colorless oil), yield: 75.3%. MS m/z (ESI): 780.3 [M+18]. $^1$H NMR (400 MHz, CDCl$_3$): δ 7.33 (m, 12H), 7.15 (m, 4H), 7.05 (m, 2H), 6.86 (d, 2H), 6.76 (d, 2H), 4.77 (m, 4H), 4.27 (m, 2H), 4.00 (m, 6H), 3.83 (m, 3H), 3.70 (m, 4H), 3.38 (m, 1H), 0.63 (m, 2H), 0.48 (m, 2H).

Step 7

(1S,2S,3S,4R,5S)-5-[4-chloro-3-[[4-[2-(cyclopropoxy)ethoxy]phenyl]methyl]phenyl]-1-(hydroxymethyl)-6,8-dioxabicyclo[3.2.1]octane-2,3,4-triol

[(1S,2S,3S,4R,5S)-2,3,4-tribenzyloxy-5-[4-chloro-3-[[4-[2-(cyclopropoxy)ethoxy]phenyl]methyl]phenyl]-6,8-dioxabicyclo[3.2.1]octan-1-yl]methanol 1g (220.3 mg, 0.29 mmol) was dissolved in 10 mL mixed solution (THF and MeOH, v:v=1:1), followed by addition of 1,2-dichlorobenzene (0.34 mL, 3 mmol) and Palladium/carbon (90 mg, 10%). The mixture was exchanged with H$_2$ three times and stirred for 3 hours, and filtered. The filtrate was concentrated under reduced pressure and the resulting residue was purified by silica gel chromatography with elution system A to obtain the title compound (1S,2S,3S,4R,5S)-5-[4-chloro-3-[[4-[2-(cyclopropoxy)ethoxy]phenyl]methyl]phenyl]-1-(hydroxymethyl)-6,8-dioxabicyclo[3.2.1]octane-2,3,4-triol 1 (140 mg, white solid), yield: 100%. MS m/z (ESI): 510.2 [M+18]. $^1$H NMR (400 MHz, CD$_3$OD): δ 7.45 (d, 1H), 7.36 (m, 2H), 7.10

(d, 2H), 6.82 (m, 2H), 4.14 (d, 1H), 4.05 (m, 4H), 3.83 (m, 3H), 3.78 (m, 1H), 3.66 (m, 2H), 3.57 (m, 2H), 3.40 (m, 1H), 0.56 (m, 2H), 0.48 (m, 2H).
Example 2
(1S,2S,3S,4R,5S)-5-[4-chloro-3-[(2,3-difluoro-4-methoxy-phenyl)methyl]phenyl]-1-(hydroxymethyl)-6,8-dioxabicyclo[3.2.1]octane-2,3,4-triol
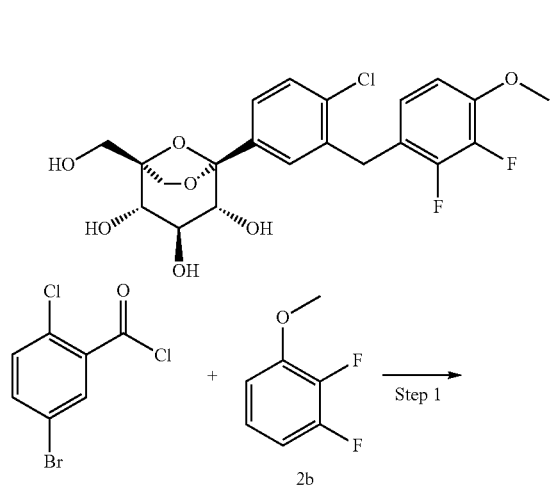
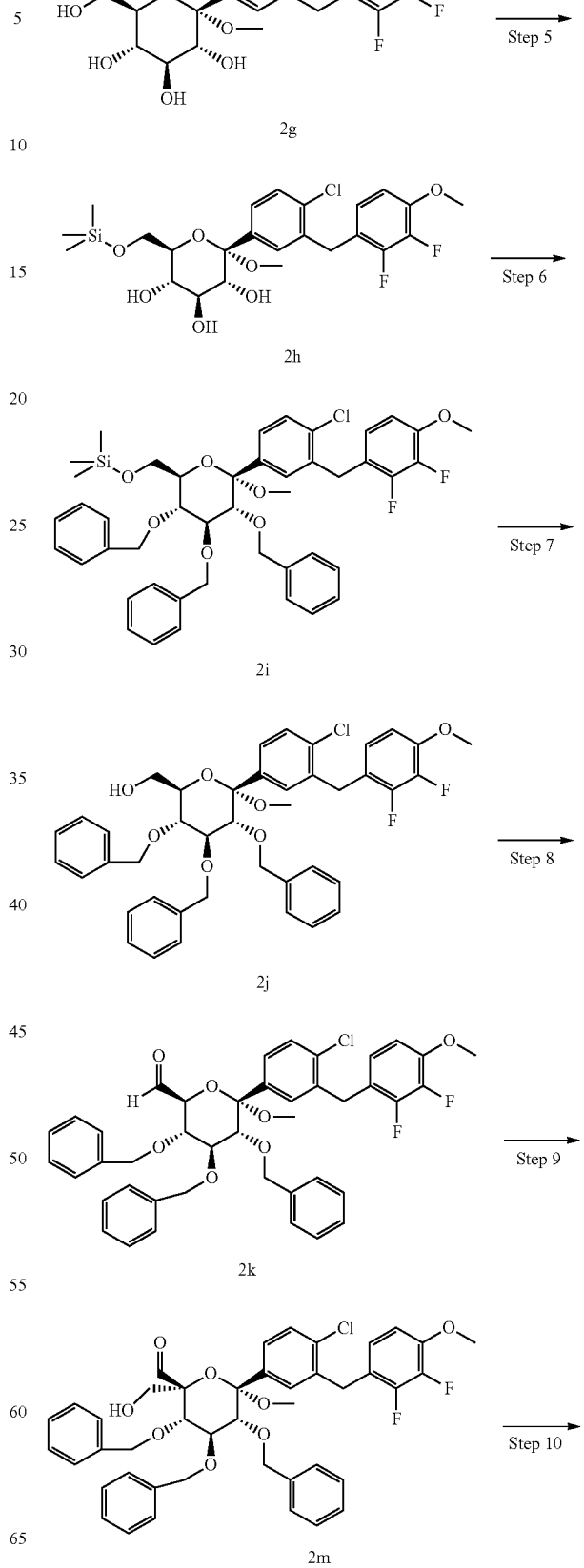

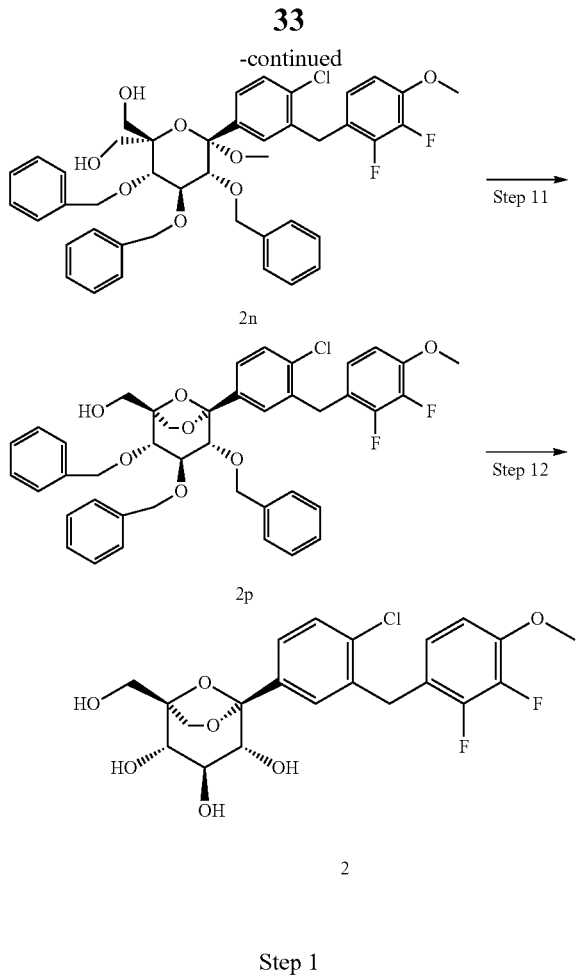

resulting residue was dissolved in ethyl acetate (100 mL) and partitioned. The organic extract was washed with water (20 mL×2), combined, dried over anhydrous magnesium sulfate, and filtered. The filtrate was concentrated under reduced pressure to obtain the title compound (5-bromo-2-chloro-phenyl)-(2,3-difluoro-4-methoxy-phenyl)methanol 2d (5.1 g, yellow grease), yield: 99.6%.

Step 3

1-[(5-bromo-2-chloro-phenyl)methyl]-2,3-difluoro-4-methoxy-benzene (5-bromo-2-chloro-phenyl)-(2,3-difluoro-4-methoxy-phenyl)methanol 2d (5.1 g, 14.1 mmol) was dissolved in 40 mL methylene chloride, followed by addition of triethyl silane (6.75 mL, 42.3 mmol) and dropwise addition of boron trifluoride diethyl ether (3.57 mL, 28.2 mmol). The reaction mixture was stirred for 16 hours. Thereafter, the reaction mixture was partitioned after 20 mL saturated sodium carbonate solution were added. The aqueous phase was extracted with dichlormethane (20 mL×3) and the organic extract was combined, dried over anhydrous magnesium sulfate, and filtered. The filtrate was concentrated under reduced pressure and the resulting residue was purified by silica gel chromatography with elution system B to obtain the title compound 1-[(5-bromo-2-chloro-phenyl)methyl]-2,3-difluoro-4-methoxy-benzene 2e (3.55 g, white solid), yield: 72.4%. 1H NMR (400 MHz, CDCl3): δ 7.36-7.33 (m, 1H), 7.30-7.27 (m, 2H), 6.81-6.79 (m, 1H), 6.73-6.69 (m, 1H), 4.00 (s, 2H), 3.92 (s, 3H).

Step 4

(2S,3R,4S,5S,6R)-2-[4-chloro-3-[(2,3-difluoro-4-methoxy-phenyl)methyl]phenyl]-6-(hydroxymethyl)-2-methoxy-tetrahydropyran-3,4,5-triol 1-[(5-bromo-2-chloro-phenyl)methyl]-2,3-difluoro-4-methoxy-benzene 2e (3.55 g, 10.2 mmol) was dissolved in 30 mL mixed solution (THF and toluene, v:v=1:2) and cooled to −78° C., followed by dropwise addition of a solution of nBuLi in n-hexane (4.9 mL, 12.26 mmol). After stirring for 1 hour at −78° C., a solution of (3R,4S,5R,6R)-3,4,5-tris(trimethylsilyloxy)-6-(trimethylsilyloxymethyl)tetrahydropyran-2-one 2f (5.24 g, 11.22 mmol, prepared according to the method in WO2010048358) in toluene (30 mL) was added. The reaction mixture was stirred for 3 hours at −78° C. Thereafter, the reaction mixture was concentrated under reduced pressure after 30 mL saturated sodium carbonate solution were added. The residue was dissolved in 30 mL saturated sodium chloride solution and extracted with ethyl acetate (50 mL×3) and the organic extract was combined, dried over anhydrous magnesium sulfate, and filtered. The filtrate was concentrated under reduced pressure and the resulting residue was purified by silica gel chromatography with elution system A to obtain the title compound (2S,3R,4S,5S,6R)-2-[4-chloro-3-[(2,3-difluoro-4-methoxy-phenyl)methyl]phenyl]-6-(hydroxymethyl)-2-methoxy-tetrahydropyran-3,4,5-triol 2g (1.31 g, white solid), yield: 27.9%. MS m/z (ESI): 429.1 [M−31]

Step 5

(2S,3R,4S,5S,6R)-2-[4-chloro-3-[(2,3-difluoro-4-methoxy-phenyl)methyl]phenyl]-2-methoxy-6-(trimethylsilyloxymethyl)tetrahydropyran-3,4,5-triol (2S,3R,4S,5S,6R)-2-[4-chloro-3-[(2,3-difluoro-4-methoxy-phenyl)methyl]phenyl]-6-(hydroxymethyl)-2-methoxy-tetrahydropyran-3,4,5-triol 2g (1.31 g, 2.84 mmol) was dis-

Step 1

(5-bromo-2-chloro-phenyl)-(2,3-difluoro-4-methoxy-phenyl)one 5-bromo-2-chloro-benzoyl chloride 2a (7.22 g, 28.45 mmol) and 1,2-difluoro-3-methoxybenzene 2b (4.1 g, 28.45 mmol, prepared according to the method in CN2003468A) were dissolved in 50 mL methylene chloride and cooled to 0° C., followed by addition of aluminum trichloride (3.4 g, 25.6 mmol) in batch. The mixture was stirred for 16 hours. Then, the mixture was partitioned after 20 mL 1 M hydrochloric acid were added and extracted with dichloromethane (50 mL×2). The organic extract was washed with saturated sodium carbonate solution (50 mL) and saturated sodium chloride solution (50 mL), combined, dried over anhydrous magnesium sulfate, and filtered. The filtrate was concentrated under reduced pressure to obtain the title compound (5-bromo-2-chloro-phenyl)-(2,3-difluoro-4-methoxy-phenyl)one 2c (5.1 g, yellow solid), yield: 49.5%. MS m/z (ESI): 362.9 [M+18].

Step 2

(5-bromo-2-chloro-phenyl)-(2,3-difluoro-4-methoxy-phenyl)methanol (5-bromo-2-chloro-phenyl)-(2,3-difluoro-4-methoxy-phenyl)one 2c (5.1 g, 14.1 mmol) was dissolved in 40 mL of mixed solution (THF and MeOH, v:v=1:1) and cooled to 0° C., followed by addition of sodium borohydride in batch (1.07 g, 28.2 mmol). The reaction mixture was stirred for 30 minutes. Thereafter, the reaction mixture was concentrated under reduced pressure after 10 mL acetone were added. The solved in 15 mL pyridine, followed by addition of 4-dimethylamino pyridine (70 mg, 0.57 mmol) and trimethylchloro-silane (514 mg, 3.4 mmol). The reaction mixture was stirred for 16 hours and then concentrated under reduced pressure. The resulting residue was dissolved in 150 mL ethyl acetate and washed with pyridine (50 mL×2), water (30 mL) and saturated sodium chloride solution (30 mL) in turn. The organic extract was combined, dried over anhydrous magnesium sulfate, and filtered. The filtrate was concentrated under reduced pressure to obtain the title compound (2S,3R,4S,5S, 6R)-2-[4-chloro-3-[(2,3-difluoro-4-methoxy-phenyl)methyl]phenyl]-2-methoxy-6-(trimethylsilyloxymethyl)tetrahydropyran-3,4,5-triol 2h (1.63 g, pale yellow solid), yield: 100%.

Step 6

[[(2R,3R,4S,5R,6S)-3,4,5-tribenzyloxy-6-[4-chloro-3-[(2,3-difluoro-4-methoxy-phenyl)methyl]phenyl]-6-methoxy-tetrahydropyran-2-yl]methoxy]trimethyl-silane (2S,3R,4S,5S,6R)-2-[4-chloro-3-[(2,3-difluoro-4-methoxy-phenyl)methyl]phenyl]-2-methoxy-6-(trimethylsilyloxymethyl)tetrahydropyran-3,4,5-triol 2h (1.63 g, 2.84 mmol) was dissolved in 30 mL DMF and cooled to 0° C., followed by addition of 60% NaH (570 mg, 14.2 mmol). Then the reaction mixture was warmed to room temperature and stirred for 45 minutes. Thereafter, benzyl bromide (1.7 mL, 14.2 mmol) was added before the reaction mixture was stirred overnight. The reaction mixture was concentrated under reduced pressure after 5 mL methanol were added. After 150 mL ethyl acetate and 50 mL water were added into the residue, the resulting residue was partitioned and the organic extract was washed with water (50 mL), combined, dried over anhydrous magnesium sulfate, and filtered. The filtrate was concentrated under reduced pressure to obtain the title compound [[(2R,3R,4S,5R,6S)-3,4,5-tribenzyloxy-6-[4-chloro-3-[(2,3-difluoro-4-methoxy-phenyl)methyl]phenyl]-6-methoxy-tetrahydropyran-2-yl]methoxy]trimethyl-silane 21 (2.4 g, yellow grease), with yield: 100%.

Step 7

[(2R,3R,4S,5R,6S)-3,4,5-tribenzyloxy-6-[4-chloro-3-[(2,3-difluoro-4-methoxy-phenyl)methyl]phenyl]-6-methoxy-tetrahydropyran-2-yl]methanol

[[(2R,3R,4S,5R,6S)-3,4,5-tribenzyloxy-6-[4-chloro-3-[(2,3-difluoro-4-methoxy-phenyl)methyl]phenyl]-6-methoxy-tetrahydropyran-2-yl]methoxy]trimethylsilane 21 (2.4 g, 2.84 mmol) was dissolved in 20 mL methanol and stirred for 1 hour after addition of acetyl chloride (30 μL, 0.43 mmol). The reaction mixture was concentrated under reduced pressure and the resulting residue was purified by silica gel chromatography with elution system B to obtain the title compound [(2R,3R,4S,5R,6S)-3,4,5-tribenzyloxy-6-[4-chloro-3-[(2,3-difluoro-4-methoxy-phenyl)methyl]phenyl]-6-meth oxy-tetrahydropyran-2-yl]methanol 2j (1.25 g, yellow solid), with yield: 60.4%.

Step 8

(2S,3S,4S,5R,6S)-3,4,5-tribenzyloxy-6-[4-chloro-3-[(2,3-difluoro-4-methoxy-phenyl)methyl]phenyl]-6-methoxy-tetrahydropyran-2-carbaldehyde Oxalyl chloride was dissolved in 5 mL methylene chloride and cooled to −78° C., followed by dropwise addition of 3 ml solution of dimethyl sulfoxide ((0.26 mL, 3.59 mmol) in methylene chloride. The reaction mixture was stirred for 15 minutes, before 5 mL solution of [(2R,3R,4S,5R,6S)-3,4,5-tribenzyloxy-6-[4-chloro-3-[(2,3-difluoro-4-methoxy-phenyl)methyl]phenyl]-6-methoxy-tetrahydropyran-2-yl]methanol 2j (1.25 g, 1.71 mmol) in methylene chloride was dropwise added. The mixture was stirred for 40 minutes. The triethylamine (1.19 mL, 8.55 mmol) was dropwise added, before the reaction mixture was warmed to room temperature and stirred for 1.5 hours. Thereafter, the reaction mixture was washed with 5 mL 1 M hydrochloric acid and the organic extract was collected, dried over anhydrous magnesium sulfate, and filtered. The filtrate was concentrated under reduced pressure to obtain the title compound (2S,3S,4S,5R,6S)-3,4,5-tribenzyloxy-6-[4-chloro-3-[(2,3-difluoro-4-methoxy-phenyl)methyl]phenyl]-6-methoxy-tetrahydropyran-2-carbaldehyde 2k (1.24 g, yellow solid), which was used in the next step without purification.

Step 9

(2S,3S,4S,5R,6S)-3,4,5-tribenzyloxy-6-[4-chloro-3-[(2,3-difluoro-4-methoxy-phenyl)methyl]phenyl]-2-(hydroxymethyl)-6-methoxy-tetrahydropyran-2-carbaldehyde (2S,3S,4S,5R,6S)-3,4,5-tribenzyloxy-6-[4-chloro-3-[(2,3-difluoro-4-methoxy-phenyl)methyl]phenyl]-6-methoxy-tetrahydropyran-2-carbaldehyde 2k (1.24 g, 1.71 mmol) was dissolved in 15 mL 1,4-dioxane, followed by 37%-40% aqueous solution of formaldehyde (2.8 mL, 34.2 mmol) and 1.5 mL of sodium hydroxide solution (205 mg, 5.13 mmol). The reaction mixture was stirred overnight at 70° C. Thereafter, the reaction mixture was concentrated under reduced pressure and partitioned after 30 mL ethyl acetate and 15 mL saturated sodium chloride solution were added. The aqueous phase was extracted with ethyl acetate (15 mL×2) and the organic extract was combined, dried over anhydrous magnesium sulfate, and filtered. The filtrate was concentrated under reduced pressure to obtain the title compound (2S,3S,4S,5R,6S)-3,4,5-tribenzyloxy-6-[4-chloro-3-[(2,3-difluoro-4-methoxy-phenyl)methyl]phenyl]-2-(hydroxymethyl)-6-methoxy-tetrahydropyran-2-carbaldehyde 2m (1.29 g, yellow grease), which was used directly in the next step without purification.

Step 10

[(3S,4S,5R,6S)-3,4,5-tribenzyloxy-6-[4-chloro-3-[(2,3-difluoro-4-methoxy-phenyl)methyl]phenyl]-2-(hydroxymethyl)-6-methoxy-tetrahydropyran-2-yl]methanol (2S,3S,4S,5R,6S)-3,4,5-tribenzyloxy-6-[4-chloro-3-[(2,3-difluoro-4-methoxy-phenyl)methyl]phenyl]-2-(hydroxymethyl)-6-methoxy-tetrahydropyran-2-carbaldehyde 2m (1.29 g, 1.71 mmol) was dissolved in 15 mL of mixed solution (THF and MeOH, v:v=1:2), followed by addition of sodium borohydride (129 mg, 3.42 mmol). The reaction mixture was stirred for 20 minutes. Thereafter, the reaction mixture was concentrated under reduced pressure and partitioned after 30 mL ethyl acetate and 15 mL saturated sodium chloride solution were added. The aqueous phase was extracted with ethyl acetate (15 mL×2) and the organic extract was combined, dried over anhydrous magnesium sulfate, and filtered. The filtrate was concentrated under reduced pressure and the resulting residue was purified by silica gel chromatography with elution system B to obtain the title compound [(3S,4S,5R,6S)-3,4,5-tri-benzyloxy-6-[4-chloro-3-[(2,3-difluoro-4-methoxy-phenyl)methyl]phenyl]-2-(hydroxymethyl)-6-methoxy-tetrahydropyran-2-yl]methanol 2n (520 mg, white solid), with yield: 40%.

Step 11

[(1S,2S,3S,4R,5S)-2,3,4-tribenzyloxy-5-[4-chloro-3-[(2,3-difluoro-4-methoxy-phenyl)methyl]phenyl]-6,8-dioxabicyclo[3.2.1]octan-1-yl]methanol

[(3S,4S,5R,6S)-3,4,5-tribenzyloxy-6-[4-chloro-3-[(2,3-difluoro-4-methoxy-phenyl)methyl]phenyl]-2-(hydroxymethyl)-6-methoxy-tetrahydropyran-2-yl]methanol 2n (500 mg, 0.66 mmol) was dissolved in 10 mL dichloromethane, followed by dropwise addition of trifluoroacetic acid (0.2 mL, 2.62 mmol). The reaction mixture was stirred for 1.5 hours. Thereafter, the reaction mixture was washed with 10 mL saturated sodium bicarbonate solution and the organic extract was combined, dried over anhydrous magnesium sulfate, and filtered. The filtrate was concentrated under reduced pressure and the resulting residue was purified by silica gel chromatography with elution system B to obtain the title compound [(1S,2S,3S,4R,5S)-2,3,4-tribenzyloxy-5-[4-chloro-3-[(2,3-difluoro-4-methoxy-phenyl)methyl]phenyl]-6,8-dioxabicyclo[3.2.1]octan-1-yl]methanol 2p (360 mg, white solid), with yield: 75.3%. MS m/z (ESI): 746.2 [M+18].

Step 12

(1S,2S,3S,4R,5S)-5-[4-chloro-3-[(2,3-difluoro-4-methoxy-phenyl)methyl]phenyl]-1-(hydroxymethyl)-6,8-dioxabicyclo[3.2.1]octane-2,3,4-triol

[(1S,2S,3S,4R,5S)-2,3,4-tribenzyloxy-5-[4-chloro-3-[(2,3-difluoro-4-methoxy-phenyl)methyl]phenyl]-6,8-dioxabicyclo[3.2.1]octan-1-yl]methanol 2p (350 mg, 0.48 mmol) was dissolved in 10 mL of mixed solution (THF and MeOH, v:v=1:1), followed by addition of o-dichlorobenzene (0.55 mL, 4.8 mmol) and Palladium/carbon (300 mg, 10%) in turn. The mixture was exchanged with $H_2$ three times and stirred for 3 hours, filtered with silica gel and the filtrate was concentrated under reduced pressure and the resulting residue was purified by silica gel chromatography with elution system A to obtain the title compound (1S,2S,3S,4R,5S)-5-[4-chloro-3-[(2,3-difluoro-4-methoxy-phenyl)methyl]phenyl]-1-(hydroxymethyl)-6,8-dioxabicyclo[3.2.1]octane-2,3,4-triol 2 (210 mg, white solid), yield: 95.5%. MS m/z (ESI): 459.1 [M+1];
$^1$H NMR (400 MHz, $CD_3OD$): δ 7.42 (m, 3H), 6.81 (m, 2H), 4.16 (d, 1H), 4.10 (s, 2H), 3.87 (s, 3H), 3.82 (m, 2H), 3.68 (m, 2H), 3.55 (m, 1H), 3.61 (m, 1H).

Example 3

(1S,2S,3S,4R,5S)-5-[4-chloro-3-[(4-ethoxy-2,3-difluoro-phenyl)methyl]phenyl]-1-(hydroxymethyl)-6,8-dioxabicyclo[3.2.1]octane-2,3,4-triol

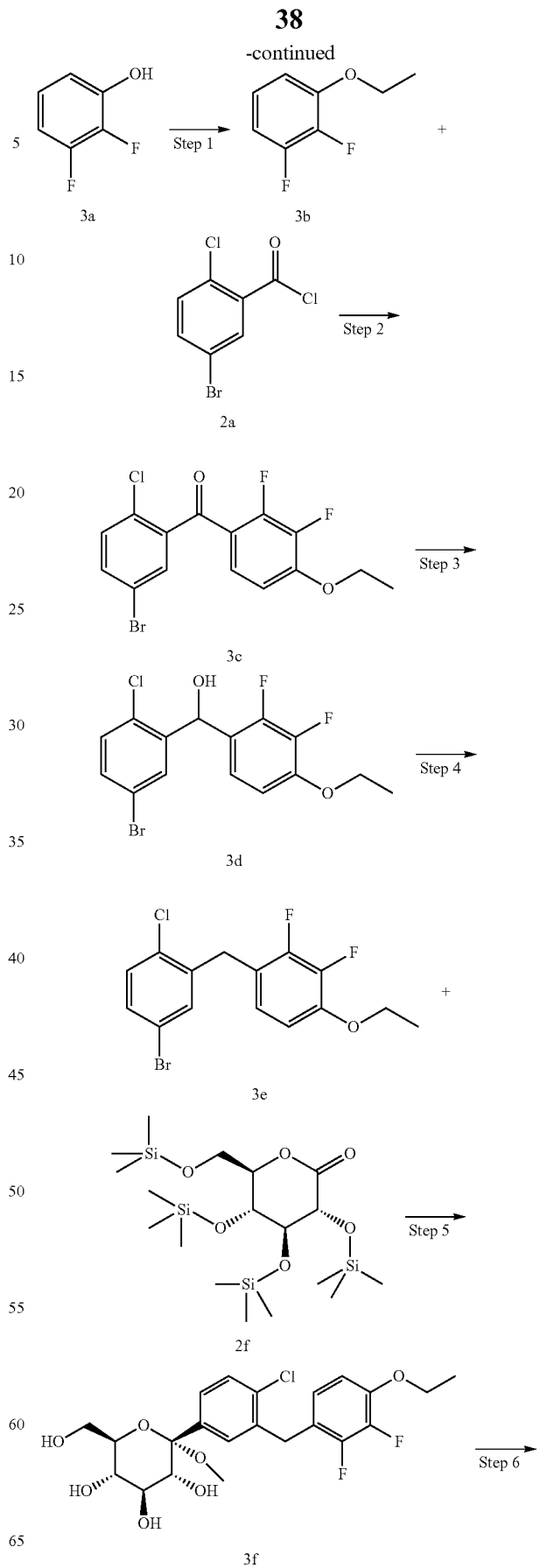

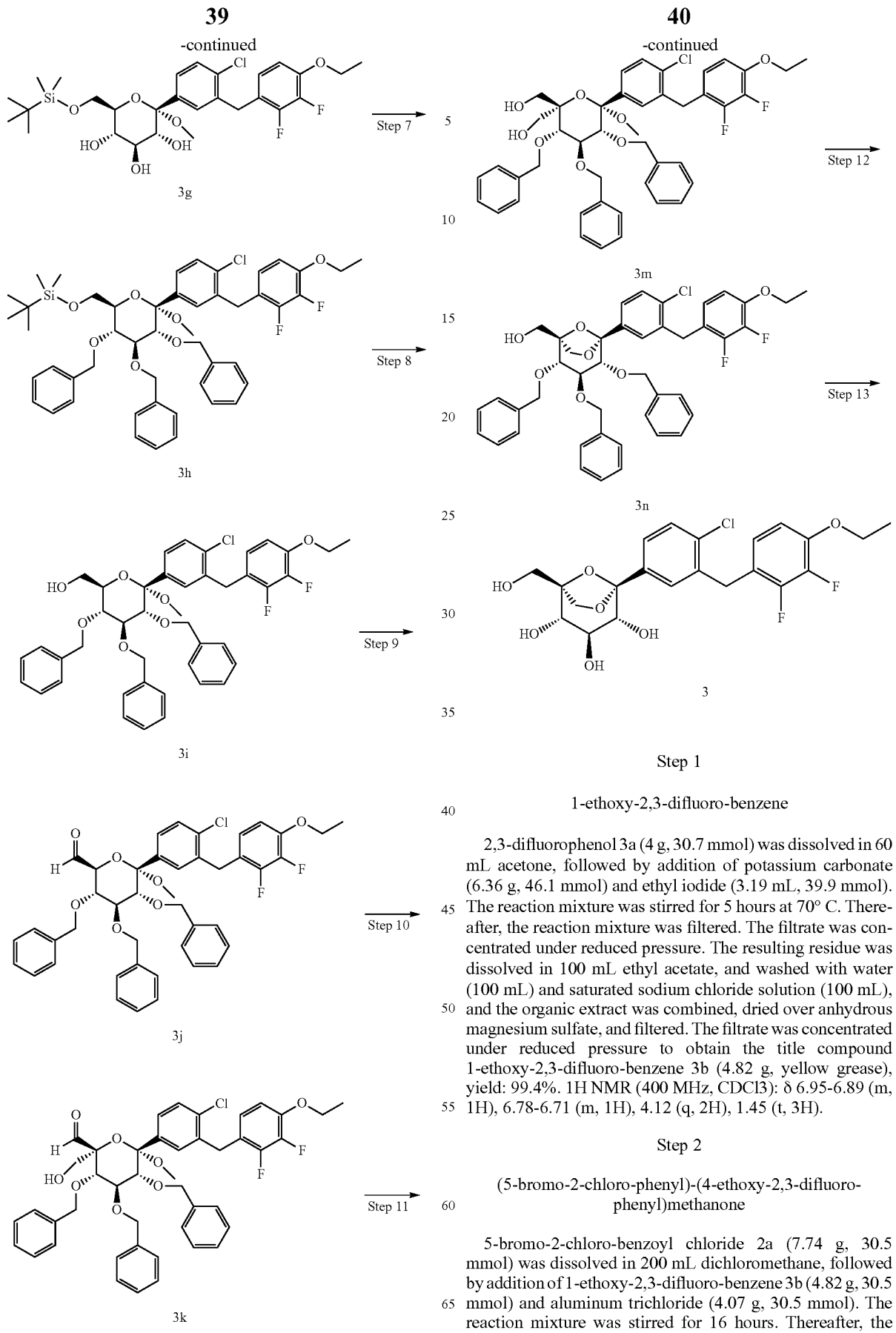

Step 1

1-ethoxy-2,3-difluoro-benzene 2,3-difluorophenol 3a (4 g, 30.7 mmol) was dissolved in 60 mL acetone, followed by addition of potassium carbonate (6.36 g, 46.1 mmol) and ethyl iodide (3.19 mL, 39.9 mmol). The reaction mixture was stirred for 5 hours at 70° C. Thereafter, the reaction mixture was filtered. The filtrate was concentrated under reduced pressure. The resulting residue was dissolved in 100 mL ethyl acetate, and washed with water (100 mL) and saturated sodium chloride solution (100 mL), and the organic extract was combined, dried over anhydrous magnesium sulfate, and filtered. The filtrate was concentrated under reduced pressure to obtain the title compound 1-ethoxy-2,3-difluoro-benzene 3b (4.82 g, yellow grease), yield: 99.4%. 1H NMR (400 MHz, CDCl3): δ 6.95-6.89 (m, 1H), 6.78-6.71 (m, 1H), 4.12 (q, 2H), 1.45 (t, 3H).

Step 2

(5-bromo-2-chloro-phenyl)-(4-ethoxy-2,3-difluoro-phenyl)methanone 5-bromo-2-chloro-benzoyl chloride 2a (7.74 g, 30.5 mmol) was dissolved in 200 mL dichloromethane, followed by addition of 1-ethoxy-2,3-difluoro-benzene 3b (4.82 g, 30.5 mmol) and aluminum trichloride (4.07 g, 30.5 mmol). The reaction mixture was stirred for 16 hours. Thereafter, the mixture was partitioned after 100 mL 2 M hydrochloric acid were added. The organic extract was washed with saturated sodium chloride solution (100 mL) and combined, dried over anhydrous magnesium sulfate, and filtered. The filtrate was concentrated under reduced pressure to obtain the title compound (5-bromo-2-chloro-phenyl)-(4-ethoxy-2,3-difluoro-phenyl)methanone 3c (8.0 g, yellow grease), yield: 70.2%. MS m/z (ESI): 376.9 [M+1].

Step 3

(5-bromo-2-chloro-phenyl)-(4-ethoxy-2,3-difluoro-phenyl)methanol (5-bromo-2-chloro-phenyl)-(4-ethoxy-2,3-difluoro-phenyl)methanone 3c (8.0 g, 21.3 mmol) was dissolved in 240 mL of mixed solution (THF and MeOH, v:v=1:1), followed by addition of potassium borohydride (1.73 g, 32.0 mmol) in an ice bath. The reaction mixture was stirred for 16 hours at room temperature. Thereafter, 50 mL 1 M hydrochloric acid were added. The reaction mixture was concentrated under reduced pressure and extracted with dichloromethane (100 mL×2). The organic extract was combined, dried over anhydrous magnesium sulfate, and filtered. The filtrate was concentrated under reduced pressure to obtain the title compound (5-bromo-2-chloro-phenyl)-(4-ethoxy-2,3-difluoro-phenyl)methanol 3d (8.0 g, yellow grease), which was used directly in the next step without purification.

Step 4

1-[(5-bromo-2-chloro-phenyl)methyl]-4-ethoxy-2,3-difluoro-benzene (5-bromo-2-chloro-phenyl)-(4-ethoxy-2,3-difluoro-phenyl)methanol 3d (8.0 g, 21.2 mmol) was dissolved in 150 mL of mixed solution (acetonitrile and dichloromethane, v:v=2:1), followed by addition of triethylsilane (10.1 mL, 63.6 mmol) and boron trifluoride etherate (5.3 mL, 42.4 mmol). The reaction mixture was stirred for 3 hours, before 100 mL 2 M potassium hydroxide were added. The organic extract was combined, dried over anhydrous magnesium sulfate, and filtered. The filtrate was concentrated under reduced pressure and the resulting residue was purified by silica gel chromatography with elution system C to obtain the title compound 1-[(5-bromo-2-chloro-phenyl)methyl]-4-ethoxy-2,3-difluoro-benzene 3e (5.5 g, white solid), yield: 72.4%. MS m/z (ESI): 360.5 [M+1]. 1H NMR (400 MHz, CDCl3): δ 7.36-7.27 (m, 3H), 6.81-6.76 (dd, 1H), 6.72-6.68 (dd, 1H), 4.17-4.13 (q, 2H), 4.10 (s, 2H), 1.50-1.47 (t, 3H).

Step 5

(2S,3R,4S,5S,6R)-2-[4-chloro-3-[(4-ethoxy-2,3-difluoro-phenyl)methyl]phenyl]-6-(hydroxymethyl)-2-methoxy-tetrahydropyran-3,4,5-triol 1-[(5-bromo-2-chloro-phenyl)methyl]-4-ethoxy-2,3-difluoro-benzene 3e (5.5 g, 15.3 mmol) was dissolved in 20 mL THF and cooled to −78° C., followed by dropwise addition of a solution of n-BuLi in n-hexane (7.3 mL, 18.3 mmol). The reaction mixture was stirred for 1 hour at −78° C. 30 mL solution of (3R,4S,5R,6R)-3,4,5-tris (trimethylsilyloxy)-6-(trimethylsilyloxymethyl)tetrahydropyran-2-one 2f (7.5 g, 16.1 mmol) in THF at −78° C. were added before the reaction mixture was stirred for 2 hours at −78° C. A solution (51 mL) of 0.6 M methanesulfonic acid in methanol was added before the reaction mixture was warmed and stirred for 16 hours at room temperature. Thereafter, the reaction mixture was concentrated under reduced pressure, dissolved in water (50 mL) and extracted with ethyl acetate (100 mL×4). The organic extract was combined, dried over anhydrous magnesium sulfate, and filtered. The filtrate was concentrated under reduced pressure and the resulting residue was purified by silica gel chromatography with elution system A to obtain the title compound (2S,3R,4S,5S,6R)-2-[4-chloro-3-[(4-ethoxy-2,3-difluoro-phenyl)methyl]phenyl]-6-(hydroxymethyl)-2-methoxy-tetrahydropyran-3,4,5-triol 3f (3.05 g, white solid), yield: 45.5%.

Step 6

(2S,3R,4S,5S,6R)-6-[(tert-butyl(dimethyl)silyl) oxymethyl]-2-[4-chloro-3-[(4-ethoxy-2,3-difluoro-phenyl)methyl]phenyl]-2-methoxy-tetrahydropyran-3,4,5-triol (2S,3R,4S,5S,6R)-2-[4-chloro-3-[(4-ethoxy-2,3-difluoro-phenyl)methyl]phenyl]-6-(hydroxymethyl)-2-methoxy-tetrahydropyran-3,4,5-triol 3f (3.0 g, 6.8 mmol) was dissolved in 30 mL pyridine, followed by addition of 4-dimethylamino pyridine (166 mg, 1.36 mmol) and TBSCl (1.23 g, 8.2 mmol) in turn. The reaction mixture was stirred for 16 hours. Thereafter, the reaction mixture was concentrated under reduced pressure before 150 mL ethyl acetate were added. The reaction mixture was washed with saturated copper sulfate solution (100 mL) and saturated sodium chloride solution (100 mL) in turn. The organic extract was combined, dried over anhydrous magnesium sulfate, and filtered. The filtrate was concentrated under reduced pressure to obtain the title compound (2S,3R,4S,5S,6R)-6-[(tert-butyl(dimethyl)silyl) oxymethyl]-2-[4-chloro-3-[(4-ethoxy-2,3-difluoro-phenyl) methyl]phenyl]-2-methoxy-tetrahydro-pyran-3,4,5-triol 3g (3.75 g, white solid), yield: 99.7%.

Step 7

[[(2R,3R,4S,5R,6S)-3,4,5-tribenzyloxy-6-[4-chloro-3-[(4-ethoxy-2,3-difluoro-phenyl)methyl]phenyl]-6-methoxy-tetrahydropyran-2-yl]tert-butyl-dimethyl-methoxy]silane (2S,3R,4S,5S,6R)-6-[(tert-butyl(dimethyl)silyl)oxymethyl]-2-[4-chloro-3-[(4-ethoxy-2,3-difluoro-phenyl)methyl]phenyl]-2-methoxy-tetrahydropyran-3,4,5-triol 3g (3.75 g, 6.8 mmol) was dissolved in 30 mL DMF and cooled to 0° C., followed by addition of 60% NaH (1.36 g, 34 mmol). The reaction mixture was warmed and stirred for 45 minutes at room temperature before tetrabutylammonium iodide (125 mg, 0.34 mmol) and benzyl bromide (4.01 mL, 34 mmol) were added in turn. After stirring for 16 hours at room temperature, the reaction mixture was concentrated under reduced pressure after 10 mL methanol were added. The resulting residue was dissolved in 100 mL ethyl acetate and partitioned. The organic extract was washed with water (50 mL×2) and combined, dried over anhydrous magnesium sulfate, and filtered. The filtrate was concentrated under reduced pressure to obtain the title compound [[(2R,3R,4S,5R,6S)-3, 4,5-tribenzyloxy-6-[4-chloro-3-[(4-ethoxy-2,3-difluoro-phenyl)methyl]phenyl]-6-methoxy-tetrahydropyran-2-yl] tert-butyl-dimethyl-methoxy]silane 3h (4.2 g, colourless grease), yield: 75.0%.

Step 8

[(2R,3R,4S,5R,6S)-3,4,5-tribenzyloxy-6-[4-chloro-3-[(4-ethoxy-2,3-difluoro-phenyl)methyl]phenyl]-6-methoxy-tetrahydropyran-2-yl]methanol

[[(2R,3R,4S,5R,6S)-3,4,5-tribenzyloxy-6-[4-chloro-3-[(4-ethoxy-2,3-difluoro-phenyl)methyl]phenyl]-6-methoxy-tetrahydropyran-2-yl]tert-butyl-dimethyl-methoxy]silane 3h (4.7 g, 5.46 mmol) was dissolved in 50 mL methanol, followed by addition of acetyl chloride (80 mg, 0.82 mmol). The reaction mixture was stirred for 1 hour at room temperature. Thereafter, the reaction mixture was concentrated under reduced pressure and the resulting residue was purified by silica gel chromatography with elution system B to obtain the title compound [(2R,3R,4S,5R,6S)-3,4,5-tribenzyloxy-6-[4-chloro-3-[(4-ethoxy-2,3-difluoro-phenyl)methyl]phenyl]-6-methoxy-tetrahydro-pyran-2-yl]methanol 31 (2.5 g, yellow grease), yield: 61.4%.

Step 9

(2S,3S,4S,5R,6S)-3,4,5-tribenzyloxy-6-[4-chloro-3-[(4-ethoxy-2,3-difluoro-phenyl)methyl]phenyl]-6-methoxy-tetrahydropyran-2-carbaldehyde Oxalyl chloride (0.37 mL, 4.37 mmol) was dissolved in 20 mL dichloromethane and cooled to −78° C., followed by dropwise addition of a solution (10 mL) of dimethyl sulfoxide (0.5 mL, 7.05 mmol) in dichloromethane and a solution (20 mL) of [(2R,3R,4S,5R,6S)-3,4,5-tribenzyloxy-6-[4-chloro-3-[(4-ethoxy-2,3-difluoro-phenyl)methyl]phenyl]-6-methoxy-tetrahydropyran-2-yl]methanol 3i (2.5 g, 3.36 mmol) in dichloromethane in turn. The reaction mixture was stirred for 30 minutes at −78° C. Triethylamine (2.33 mL, 16.8 mmol) was added before the reaction mixture was warmed and stirred for 16 hours at room temperature. Thereafter, the reaction mixture was partitioned after 15 mL 1 M hydrochloric acid were added. The organic extract was washed with saturated sodium chloride solution (20 mL×2) and combined, dried over anhydrous magnesium sulfate, and filtered. The filtrate was concentrated under reduced pressure to obtain the title compound (2S,3S,4S,5R,6S)-3,4,5-tribenzyloxy-6-[4-chloro-3-[(4-ethoxy-2,3-difluoro-phenyl)methyl]phenyl]-6-methoxy-tetrahydropyran-2-carbaldehyde 3j (2.4 g, yellow grease), yield: 96.0%.

Step 10

(2S,3S,4S,5R,6S)-3,4,5-tribenzyloxy-6-[4-chloro-3-[(4-ethoxy-2,3-difluoro-phenyl)methyl]phenyl]-2-(hydroxymethyl)-6-methoxy-tetrahydropyran-2-carbaldehyde (2S,3S,4S,5R,6S)-3,4,5-tribenzyloxy-6-[4-chloro-3-[(4-ethoxy-2,3-difluoro-phenyl)methyl]phenyl]-6-methoxy-tetrahydropyran-2-carbaldehyde 3j (2.4 g, 3.23 mmol) was dissolved in 20 mL 1,4-dioxane, followed by addition of 5 mL 37% formaldehyde solution and 13 mL 1 M sodium hydroxide. The reaction mixture was stirred for 21 hours at 70° C. Thereafter, the reaction mixture was extracted with ethyl acetate (50 mL×3) after 20 mL of saturated sodium chloride solution were added. The organic extract was combined, dried over anhydrous magnesium sulfate, and filtered. The filtrate was concentrated under reduced pressure to obtain the title compound (2S,3S,4S,5R,6S)-3,4,5-tribenzyloxy-6-[4-chloro-3-[(4-ethoxy-2,3-difluoro-phenyl)methyl]phenyl]-2-(hydroxymethyl)-6-methoxy-tetrahydropyran-2-carbaldehyde 3k (1.6 g, yellow grease), yield: 64.0%.

Step 11

[(3S,4S,5R,6S)-3,4,5-tribenzyloxy-6-[4-chloro-3-[(4-ethoxy-2,3-difluoro-phenyl)methyl]phenyl]-2-(hydroxymethyl)-6-methoxy-tetrahydropyran-2-yl]methanol (2S,3S,4S,5R,6S)-3,4,5-tribenzyloxy-6-[4-chloro-3-[(4-ethoxy-2,3-difluoro-phenyl)methyl]phenyl]-2-(hydroxymethyl)-6-methoxy-tetrahydropyran-2-carbaldehyde 3k (1.6 g, 2.1 mmol) was dissolved in 35 mL of mixed solution (THF and MeOH, v:v=2:5), followed by addition of sodium borohydride (78 mg, 4.2 mmol). The reaction mixture was stirred for 2 hours. Thereafter, the reaction mixture was concentrated under reduced pressure and the resulting residue was purified by silica gel chromatography with elution system B to obtain the title compound [(3S,4S,5R,6S)-3,4,5-tribenzyloxy-6-[4-chloro-3-[(4-ethoxy-2,3-difluoro-phenyl)methyl]phenyl]-2-(hydroxymethyl)-6-methoxy-tetrahydropyran-2-yl]methanol 3m (1.0 g, yellow grease), yield: 62.5%.

Step 12

[(1S,2S,3S,4R,5S)-2,3,4-tribenzyloxy-5-[4-chloro-3-[(4-ethoxy-2,3-difluoro-phenyl)-methyl]phenyl]-6,8-dioxabicyclo[3.2.1]octan-1-yl]methanol

[(3S,4S,5R,6S)-3,4,5-tribenzyloxy-6-[4-chloro-3-[(4-ethoxy-2,3-difluoro-phenyl)methyl]phenyl]-2-(hydroxymethyl)-6-methoxy-tetrahydropyran-2-yl]methanol 3m (1.0 g, 1.29 mmol) was dissolved in 10 mL dichloromethane, followed by addition of trifluoroacetic acid (0.19 mL, 2.58 mmol). The reaction mixture was stirred for 4 hours. Thereafter, the reaction mixture was concentrated under reduced pressure and the resulting residue was purified by silica gel chromatography with elution system B to obtain the title compound [(1S,2S,3S,4R,5S)-2,3,4-tribenzyloxy-5-[4-chloro-3-[(4-ethoxy-2,3-difluoro-phenyl)methyl]phenyl]-6,8-dioxabicyclo[3.2.1]octan-1-yl]methanol 3n (500 mg, yellow grease), yield: 52.1%. MS m/z (ESI): 760.3 [M+18]. 1H NMR (400 MHz, CD3OD): δ 7.37-7.30 (m, 13H), 7.23-7.18 (m, 3H), 6.91-6.89 (m, 2H), 6.68 (dd, 1H), 6.55 (dd, 1H), 4.93-4.90 (m, 2H), 4.79-4.56 (m, 4H), 4.30-4.28 (m, 2H), 4.18-4.05 (m, 4H), 3.83-3.49 (m, 5H), 1.33 (t, 3H).

Step 13

(1S,2S,3S,4R,5S)-5-[4-chloro-3-[(4-ethoxy-2,3-difluoro-phenyl)methyl]phenyl]-1-(hydroxymethyl)-6,8-dioxabicyclo[3.2.1]octane-2,3,4-triol

[(1S,2S,3S,4R,5S)-2,3,4-tribenzyloxy-5-[4-chloro-3-[(4-ethoxy-2,3-difluoro-phenyl)methyl]phenyl]-6,8-dioxabicyclo[3.2.1]octan-1-yl]methanol 3n (550 mg, 0.74 mmol) was dissolved in 20 mL of mixed solution (THF and MeOH, v:v=1:1), followed by addition of o-dichlorobenzene (0.84 mL, 7.4 mmol) and Palladium/carbon (300 mg, 10%). The mixture was exchanged with H2 three times and stirred for 3 hours. Thereafter, the reaction mixture was filtered after a small amount of ethyl acetate was added. The filtrate was concentrated under reduced pressure and the resulting residue was purified by silica gel chromatography with elution system A to obtain the title compound (1S,2S,3S,4R,5S)-5-[4-chloro-3-[(4-ethoxy-2,3-difluoro-phenyl)methyl]phenyl]-1-

(hydroxymethyl)-6,8-dioxabicyclo[3.2.1]octane-2,3,4-triol 3 (160 mg, white solid), yield: 45.7%. MS m/z (ESI): 472.2 [M+1]. 1H NMR (400 MHz, CDCl3): δ 7.43-7.37 (m, 3H), 6.80-6.76 (m, 2H), 4.16-4.07 (m, 5H), 3.85-3.70 (m, 2H), 3.70-3.51 (m, 4H), 1.34 (t, 3H).
Example 4
(1S,2S,3S,4R,5S)-5-[4-chloro-3-[(4-ethoxy-3-fluoro-phenyl)methyl]phenyl]-1-(hydroxymethyl)-6,8-dioxabicyclo[3.2.1]octane-2,3,4-triol
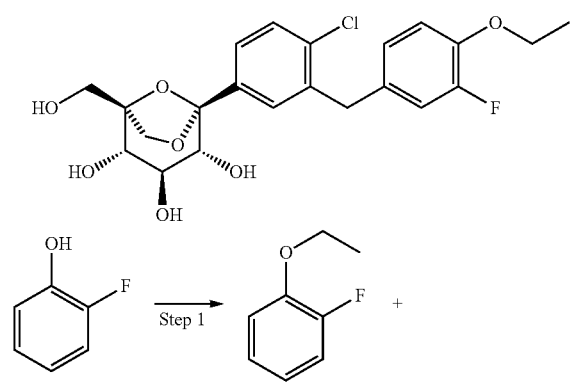
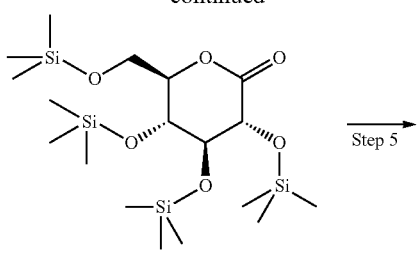
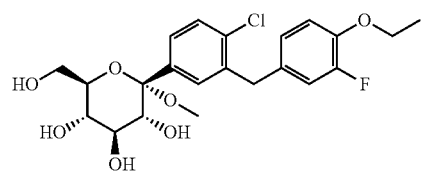
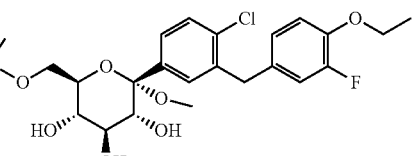
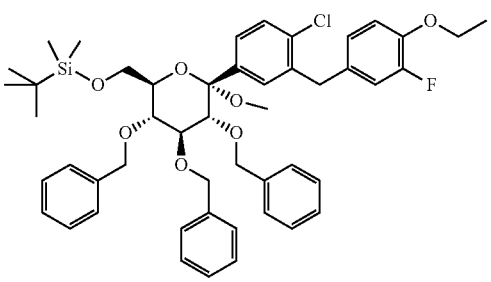
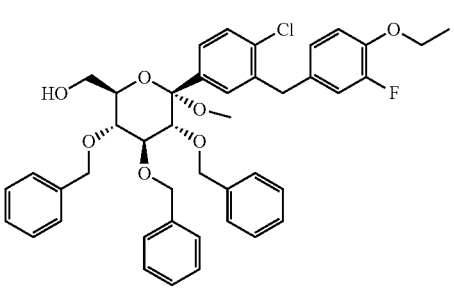
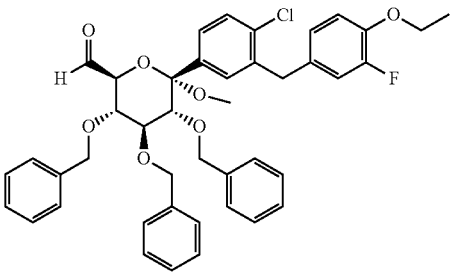

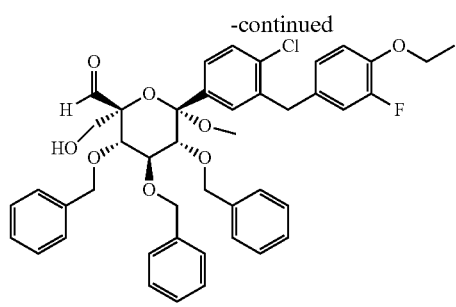

4k

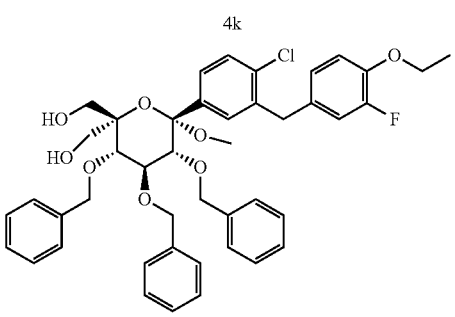

4m

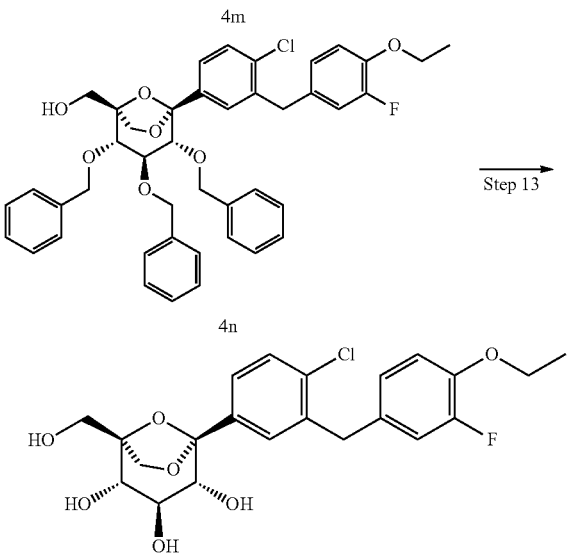

4n

4

Step 1

1-ethoxy-2-fluoro-benzene 2-fluorophenol 4a (6.7 g, 60 mmol) was dissolved in 66 mL acetone, followed by addition of ethyl iodide (6.3 mL, 78 mmol) and potassium carbonate (12.4 g, 90 mmol). The reaction mixture was refluxed in an oil bath for 5 hours. Thereafter, the reaction mixture was concentrated under reduced pressure and partitioned after 100 mL ethyl acetate and 60 mL water were added. The aqueous phase was extracted with ethyl acetate (30 mL×2) and the organic extract was combined, dried over anhydrous magnesium sulfate, and filtered. The filtrate was concentrated under reduced pressure to obtain the title compound 1-ethoxy-2-fluoro-benzene 4b (6.9 g, red grease), yield: 82.1%. MS m/z (ESI): 280.2 [2M+1].

Step 2

(5-bromo-2-chloro-phenyl)-(4-ethoxy-3-fluoro-phenyl)methanone 5-bromo-2-chloro-benzoyl chloride 2a (12.4 g, 48.8 mmol) and 1-ethoxy-2-fluoro-benzene 4b (6.84 g, 48.8 mmol) were dissolved in 100 mL dichloromethane and cooled to 0° C., followed by addition of aluminum trichloride (5.86 g, 44 mmol) in batch. The reaction mixture was stirred for 16 hours. Thereafter, the reaction mixture was partitioned after 20 mL 2 M hydrochloric acid was dropwise added in an ice bath. The aqueous phase was extracted with 30 mL dichloromethane and the organic extract was combined, dried over anhydrous magnesium sulfate, and filtered. The filtrate was concentrated under reduced pressure to obtain the title compound (5-bromo-2-chloro-phenyl)-(4-ethoxy-3-fluoro-phenyl)methanone 4c (12.7 g, yellow solid), yield: 72.6%.

MS m/z (ESI): 358.9 [M+1].

Step 3

(5-bromo-2-chloro-phenyl)-(4-ethoxy-3-fluoro-phenyl)methanol (5-bromo-2-chloro-phenyl)-(4-ethoxy-3-fluoro-phenyl)methanone 4c (12.7 g, 35.5 mmol) was dissolved in 100 mL of mixed solution (THF and MeOH, v:v=1:1), followed by addition of sodium borohydride (2.68 g, 70 mmol) in batch in an ice bath. The reaction mixture was warmed and stirred for 30 minutes at room temperature. Thereafter, the reaction mixture was concentrated under reduced pressure after 15 mL acetone were added. The residue was dissolved in 150 mL ethyl acetate and washed with saturated sodium chloride solution (50 mL×2). The organic extract was combined, dried over anhydrous magnesium sulfate, and filtered. The filtrate was concentrated under reduced pressure to obtain the title compound (5-bromo-2-chloro-phenyl)-(4-ethoxy-3-fluoro-phenyl)methanol 4d (12.7 g, orange grease), which was used directly in the next step without purification.

Step 4

4[(5-bromo-2-chloro-phenyl)methyl]-1-ethoxy-2-fluoro-benzene (5-bromo-2-chloro-phenyl)-(4-ethoxy-3-fluoro-phenyl)methanol 4d (12.7 g, 35.3 mmol) was dissolved in 100 mL dichloromethane, followed by addition of triethyl silicane (16.9 mL, 106 mmol) and dropwise addition of boron trifluoride etherate (8.95 mL, 70.6 mmol). The reaction mixture was stirred for 3 hours. Thereafter, the reaction mixture was partitioned after 50 mL saturated sodium bicarbonate solution were added. The aqueous phase was extracted with ethyl acetate (100 mL×2) and the organic extract was combined, dried over anhydrous magnesium sulfate, and filtered. The filtrate was concentrated under reduced pressure and the resulting residue was purified by silica gel chromatography with elution system B to obtain the title compound 4-[(5-bromo-2-chloro-phenyl)methyl]-1-ethoxy-2-fluoro-benzene 4e (10 g, pale yellow grease), yield: 82.4%. 1H NMR (400 MHz, CDCl$_3$): δ 7.33-7.27 (m, 3H), 6.95-6.90 (m, 3H), 4.14 (q, 2H), 4.01 (s, 2H), 1.49 (t, 3H).

Step 5

(2S,3R,4S,5S,6R)-2-[4-chloro-3-[(4-ethoxy-3-fluoro-phenyl)methyl]phenyl]-6-(hydroxymethyl)-2-methoxy-tetrahydropyran-3,4,5-triol 4-[(5-bromo-2-chloro-phenyl)methyl]-1-ethoxy-2-fluoro-benzene 4e (7.36 g, 21.4 mmol) was dissolved in 30 mL THF and cooled to −78° C., followed by dropwise addition of a solution of nBuLi in n-hexane (10.27 mL, 25.7 mmol). After stirring for 1 hour at −78° C., a solution (20 mL) of (3R,4S,5R,6R)-3,4,5-tris(trimethylsilyloxy)-6-(trimethylsilyloxymethyl)tetrahydropyran-2-one 2f (11 g, 23.6 mmol) in THF was added before the reaction mixture was stirred for 2 hours at −78° C. Then the reaction mixture was warmed and stirred for 16 hours at room temperature after 2.8 mL methylsulfonic acid and 71 mL methanol were added. Thereafter, the reaction mixture was concentrated under reduced pressure after 100 mL saturated sodium carbonate solution were added. The residue was dissolved in 50 mL saturated sodium chloride, extracted with ethyl acetate (100 mL×3). The organic extract was combined, dried over anhydrous magnesium sulfate, filtered. The filtrate was concentrated under reduced pressure and the resulting residue was purified by silica gel chromatography with elution system A to obtain the title compound (2S,3R,4S,5S,6R)-2-[4-chloro-3-[(4-ethoxy-3-fluoro-phenyl)methyl]phenyl]-6-(hydroxymethyl)-2-methoxy-tetrahydropyran-3,4,5-triol 4f (5.7 g, white solid), yield: 58.3%. 1H NMR (400 MHz, CD3OD): δ 7.56 (s, 1H), 7.48 (dd, 1H), 7.37 (dd, 1H), 6.95-6.87 (m, 3H), 4.08-4.07 (m, 4H), 3.91 (m, 1H), 3.93-3.73 (m, 2H), 3.56-3.53 (m, 1H), 3.45-3.43 (m, 1H), 3.30 (s, 2H), 3.08 (s, 3H), 1.35 (t, 3H).

Step 6

(2S,3R,4S,5S,6R)-6-[(tert-butyl(dimethyl)silyl)oxymethyl]-2-[4-chloro-3-[(4-ethoxy-3-fluoro-phenyl)methyl]phenyl]-2-methoxy-tetrahydropyran-3,4,5-triol (2S,3R,4S,5S,6R)-2-[4-chloro-3-[(4-ethoxy-3-fluoro-phenyl)methyl]phenyl]-6-(hydroxymethyl)-2-methoxy-tetrahydropyran-3,4,5-triol 4f (5.7 g, 12.5 mmol) was dissolved in 50 mL pyridine, followed by addition of TBSCl (2.26 g, 15 mmol) and 4-dimethyl-amino pyridine (305 mg, 2.5 mmol) in turn. The reaction mixture was stirred for 16 hours. Thereafter, the reaction mixture was concentrated under reduced pressure. The residue was dissolved in 200 mL ethyl acetate and washed with saturated copper sulfate solution (50 mL×3). The organic extract was combined, dried over anhydrous magnesium sulfate, filtered and concentrated under reduced pressure to obtain the title compound (2S,3R,4S,5S,6R)-6-[(tert-butyl(dimethyl)silyl)oxymethyl]-2-[4-chloro-3-[(4-ethoxy-3-fluoro-phenyl)methyl]phenyl]-2-methoxy-tetrahydropyran-3,4,5-triol 4g (7.14 g, colourless grease), which was used directly without purification in the next step.

Step 7

[[(2R,3R,4S,5R,6S)-3,4,5-tribenzyloxy-6-[4-chloro-3-[(4-ethoxy-3-fluoro-phenyl)methyl]phenyl]-6-methoxy-tetrahydropyran-2-yl]methoxy]tert-butyl-dimethylsilane (2S,3R,4S,5S,6R)-6-[(tert-butyl(dimethyl)silyl)oxymethyl]-2-[4-chloro-3-[(4-ethoxy-3-fluoro-phenyl)methyl]phenyl]-2-methoxy-tetrahydropyran-3,4,5-triol 4g (7.14 g, 12.5 mmol) was dissolved in 100 mL N,N-dimethyl formamide, followed by addition of 60% NaH (2.5 g, 62.5 mmol) in an ice bath. The reaction mixture was warmed and stirred for 40 minutes at room temperature. The mixture was stirred for 16 hours after benzyl bromide (7.5 mL, 62.5 mmol) was added. Thereafter, the reaction mixture was concentrated under reduced pressure after 20 mL methanol were added. The residue was dissolved in 200 mL ethyl acetate and 50 mL water and partitioned. The aqueous phase was extracted with ethyl acetate (50 mL). The organic extracts were washed with water (50 mL), then saturated sodium chloride (50 mL), combined, dried over anhydrous magnesium sulfate, filtered and concentrated under reduced pressure to obtain the title compound [[(2R,3R,4S,5R,6S)-3,4,5-tribenzyloxy-6-[4-chloro-3-[(4-ethoxy-3-fluoro-phenyl)methyl]phenyl]-6-methoxy-tetrahydropyran-2-yl]methoxy]tert-butyl-dimethylsilane 4h (10.5 g, yellow grease), yield: 99.8%.

Step 8

[(2R,3R,4S,5R,6S)-3,4,5-tribenzyloxy-6-[4-chloro-3-[(4-ethoxy-3-fluoro-phenyl)methyl]phenyl]-6-methoxy-tetrahydropyran-2-yl]methanol

[[(2R,3R,4S,5R,6S)-3,4,5-tribenzyloxy-6-[4-chloro-3-[(4-ethoxy-3-fluoro-phenyl)methyl]phenyl]-6-methoxy-tetrahydropyran-2-yl]methoxy]tert-butyl-dimethylsilane 4h (10.52 g, 12.5 mmol) was dissolved in 50 mL methanol, followed by dropwise addition of acetyl chloride (0.13 mL, 1.9 mmol). The reaction mixture was stirred for 1 hour. Thereafter, the reaction mixture was concentrated under reduced pressure and the resulting residue was purified by silica gel chromatography with elution system B to obtain the title compound [(2R,3R,4S,5R,6S)-3,4,5-tribenzyloxy-6-[4-chloro-3-[(4-ethoxy-3-fluoro-phenyl)methyl]phenyl]-6-methoxy-tetrahydropyran-2-yl]methanol 4i (7.6 g, yellow grease), yield: 83.6%.

Step 9

(2S,3S,4S,5R,6S)-3,4,5-tribenzyloxy-6-[4-chloro-3-[(4-ethoxy-3-fluoro-phenyl)methyl]phenyl]-6-methoxy-tetrahydropyran-2-carbaldehyde Oxalyl chloride (1.17 mL, 13.6 mmol) was dissolved in 20 mL dichloromethane and cooled to −78° C., followed by dropwise addition of a solution (20 mL) of dimethyl sulfoxide (1.56 mL, 21.9 mmol) in dichloromethane and a solution (50 mL) of [(2R,3R,4S,5R,6S)-3,4,5-tribenzyloxy-6-[4-chloro-3-[(4-ethoxy-3-fluoro-phenyl)methyl]phenyl]-6-methoxy-tetrahydropyran-2-yl]methanol 4i (7.6 g, 10.45 mmol) in dichloromethane. The reaction mixture was stirred for 30 minutes at −78° C. Triethylamine (7.25 mL, 52.3 mmol) was added before the reaction mixture was warmed and stirred for 2 hours at room temperature. Thereafter, the reaction mixture was partitioned after 50 mL 1 M hydrochloric acid were added. The organic extract was washed with saturated sodium chloride solution (50 mL×2). The aqueous phase was extracted with dichloromethane (50 mL). The organic extract was combined, dried over anhydrous magnesium sulfate, and filtered. The filtrate was concentrated under reduced pressure to obtain the title compound (2S,3S,4S,5R,6S)-3,4,5-tribenzyloxy-6-[4-chloro-3-[(4-ethoxy-3-fluoro-phenyl)methyl]phenyl]-6-methoxy-tetrahydropyran-2-carbaldehyde 4j (7.58 g, colourless grease), which was used directly without purification in the next step.

Step 10

(2S,3S,4S,5R,6S)-3,4,5-tribenzyloxy-6-[4-chloro-3-[(4-ethoxy-3-fluoro-phenyl)methyl]phenyl]-2-(hydroxymethyl)-6-methoxy-tetrahydropyran-2-carbaldehyde (2S,3S,4S,5R,6S)-3,4,5-tribenzyloxy-6-[4-chloro-3-[(4-ethoxy-3-fluoro-phenyl)methyl]phenyl]-6-methoxy-tetrahydropyran-2-carbaldehyde 4j (7.6 g, 10.45 mmol) was dissolved in 80 mL 1,4-dioxane, followed by addition of 15.8 mL 37% formaldehyde solution and sodium hydroxide (31.35 mL, 31.35 mmol) in turn. The reaction mixture was stirred for 16 hours at 70° C. Thereafter, the reaction mixture was extracted with ethyl acetate (50 mL×4) after 50 mL saturated sodium chloride solution were added. The organic extract was washed with saturated sodium bicarbonate solution (50 mL) and saturated sodium chloride solution (50 mL) and combined, dried over anhydrous magnesium sulfate, and filtered. The filtrate was concentrated under reduced pressure to obtain the title compound (2S,3S,4S,5R,6S)-3,4,5-tribenzyloxy-6-[4-chloro-3-[(4-ethoxy-3-fluoro-phenyl)methyl]phenyl]-2-(hydroxymethyl)-6-methoxy-tetrahydropyran-2-carbaldehyde 4k (7.9 g, colourless grease), which was used directly without purification in the next step.

Step 11

[(3S,4S,5R,6S)-3,4,5-tribenzyloxy-6-[4-chloro-3-[(4-ethoxy-3-fluoro-phenyl)methyl]-phenyl]-2-(hydroxymethyl)-6-methoxy-tetrahydropyran-2-yl]methanol (2S,3S,4S,5R,6S)-3,4,5-tribenzyloxy-6-[4-chloro-3-[(4-ethoxy-3-fluoro-phenyl)methyl]phenyl]-2-(hydroxymethyl)-6-methoxy-tetrahydropyran-2-carbaldehyde 4k (7.9 g, 10.45 mmol) was dissolved in 50 mL of mixed solution (THF and MeOH, v:v=2:3), followed by addition of sodium borohydride (794 mg, 20.9 mmol). The reaction mixture was stirred for 30 minutes. Thereafter, the reaction mixture was concentrated under reduced pressure after a small amount of acetone was added and the resulting residue was purified by silica gel chromatography with elution system A to obtain the title compound [(3S,4S,5R,6S)-3,4,5-tribenzyloxy-6-[4-chloro-3-[(4-ethoxy-3-fluoro-phenyl)methyl]phenyl]-2-(hydroxymethyl)-6-methoxy-tetrahydropyran-2-yl]methanol 4m (1.11 g, colourless grease), yield: 14.1%.

Step 12

[(1S,2S,3S,4R,5S)-2,3,4-tribenzyloxy-5-[4-chloro-3-[(4-ethoxy-3-fluoro-phenyl)methyl]phenyl]-6,8-dioxabicyclo[3.2.1]octan-1-yl]methanol

[(3S,4S,5R,6S)-3,4,5-tribenzyloxy-6-[4-chloro-3-[(4-ethoxy-3-fluoro-phenyl)methyl]-phenyl]-2-(hydroxymethyl)-6-methoxy-tetrahydropyran-2-yl]methanol 4m (1.11 g, 1.46 mmol) was dissolved in 20 mL dichloromethane and cooled to −10° C., followed by addition of trifluoroacetic acid (0.23 mL, 3 mmol). The reaction mixture was warmed and stirred for 2 hours and partitioned after 20 mL saturated sodium bicarbonate solution were added. The aqueous phase was extracted with dichloromethane (20 mL×2). The organic extract was combined, dried over anhydrous magnesium sulfate, and filtered. The filtrate was concentrated under reduced pressure to obtain the title compound [(1S,2S,3S,4R,5S)-2,3,4-tribenzyloxy-5-[4-chloro-3-[(4-ethoxy-3-fluoro-phenyl)methyl]phenyl]-6,8-dioxabicyclo[3.2.1]octan-1-yl]methanol 4n (830 mg, colourless grease), yield: 78.3%. MS m/z (ESI): 742.3 [M+18].

Step 13

(1S,2S,3S,4R,5S)-5-[4-chloro-3-[(4-ethoxy-3-fluoro-phenyl)methyl]phenyl]-1-(hydroxymethyl)-6,8-dioxabicyclo[3.2.1]octane-2,3,4-triol

[(1S,2S,3S,4R,5S)-2,3,4-tribenzyloxy-5-[4-chloro-3-[(4-ethoxy-3-fluoro-phenyl)methyl]phenyl]-6,8-dioxabicyclo[3.2.1]octan-1-yl]methanol 4n (830 mg, 1.14 mmol) was dissolved in 20 mL of mixed solution (THF and MeOH, v:v=1:1), followed by addition of o-dichlorobenzene (1.3 mL, 11.4 mmol) and Palladium/carbon (500 mg, 10%). The mixture was exchanged with H2 three times and stirred for 3 hours and filtered. Thereafter, the reaction mixture was eluted with a small amount of ethyl acetate. The filtrate was concentrated under reduced pressure and the resulting residue was purified by silica gel chromatography with elution system A to obtain the title compound (1S,2S,3S,4R,5S)-5-[4-chloro-3-[(4-ethoxy-2,3-difluoro-phenyl)methyl]phenyl]-1-(hydroxymethyl)-6,8-dioxabicyclo[3.2.1]octane-2,3,4-triol 4 (420 mg, white solid), yield: 81.0%. MS m/z (ESI): 472.2 [M+18]; 1H NMR (400 MHz, CD3OD): δ 7.47 (s, 1H), 7.42-7.35 (m, 2H), 6.95-6.87 (m, 3H), 4.16-4.14 (m, 1H), 4.06-4.02 (m, 4H), 3.85-3.70 (m, 2H), 3.67-3.54 (m, 4H), 1.37 (t, 3H).

Example 5

(1S,2S,3S,4R,5S)-5-[4-chloro-3-(2,3-dihydrobenzofuran-5-ylmethyl)phenyl]-1-(hydroxymethyl)-6,8-dioxabicyclo[3.2.1]octane-2,3,4-triol

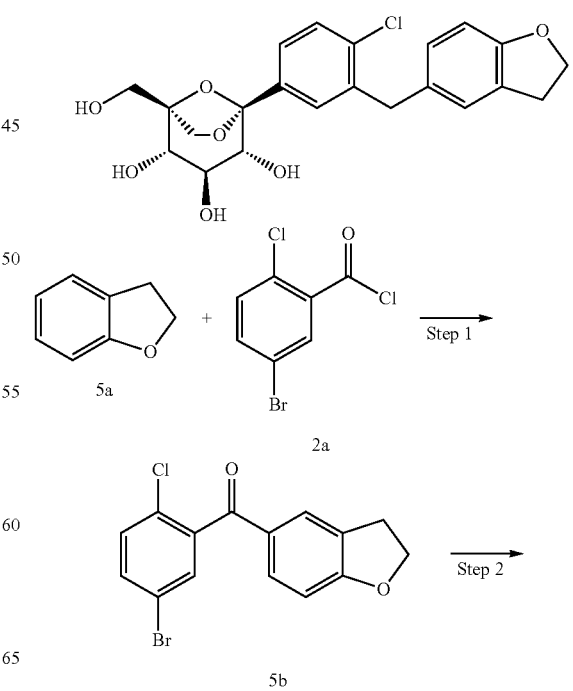

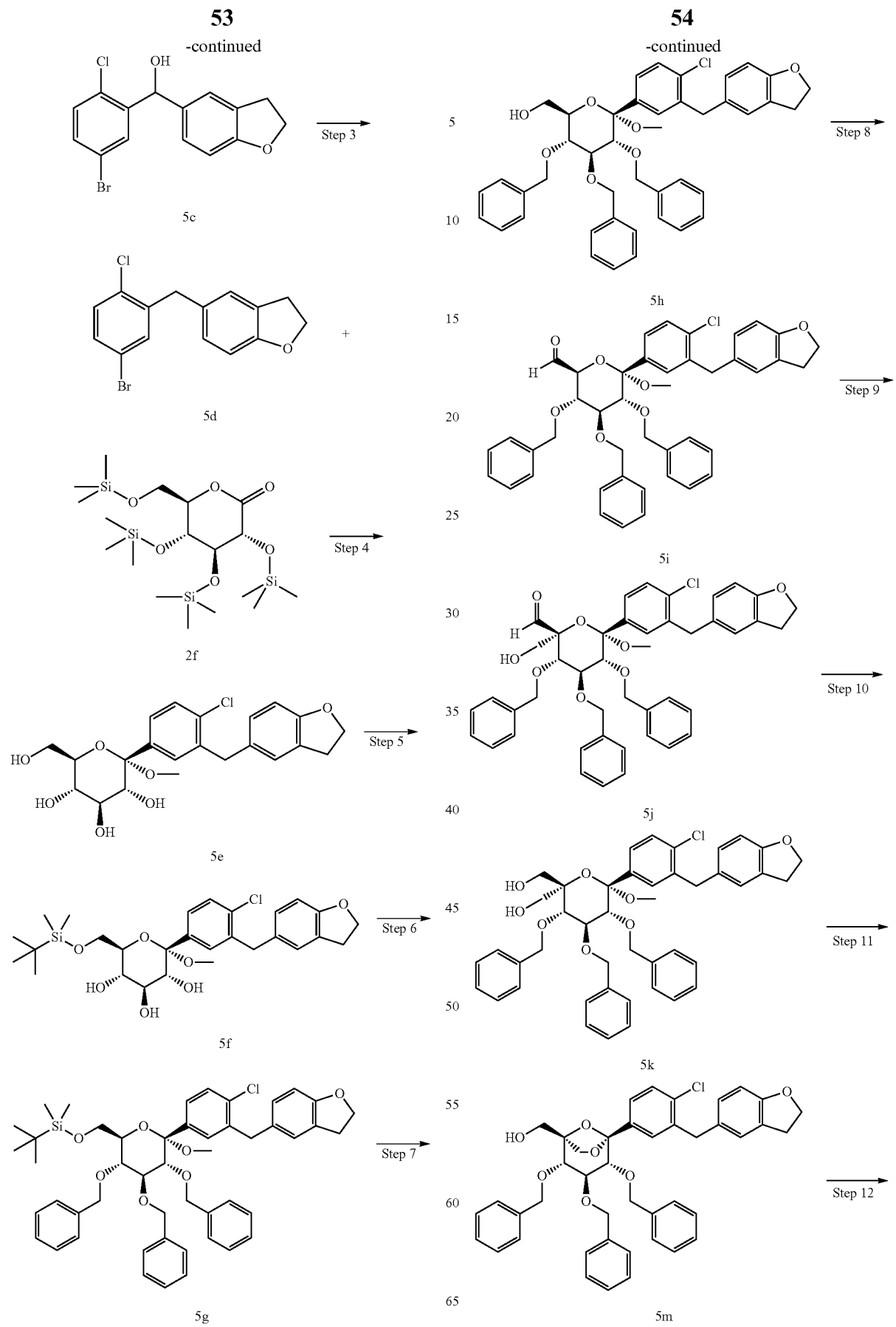

-continued

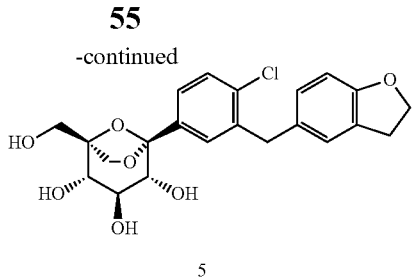

5

Step 1

(5-bromo-2-chloro-phenyl)-(2,3-dihydrobenzofuran-5-yl)methanone 5-bromo-2-chloro-benzoyl chloride 2a (10.8 g, 42.5 mmol) was dissolved in 100 mL dichloromethane, followed by addition of 2,3-dihydrobenzofuran 5a (5.11 g, 42.5 mmol) and addition of aluminum trichloride (6.8 g, 51.0 mmol) in batch. The reaction mixture was stirred for 2 hours. Thereafter, the reaction mixture was concentrated under reduced pressure and the resulting residue was purified by silica gel chromatography with elution system D to obtain the title compound (5-bromo-2-chloro-phenyl)-(2,3-dihydrobenzofuran-5-yl)methanone 5b (10.47 g, white solid), yield: 72.9%. MS m/z (ESI): 339.0 [M+1]; 1H NMR (400 MHz, CDCl$_3$): δ 7.73 (d, 1H), 7.58 (dd, 1H), 7.53 (dd, 1H), 7.47 (d, 1H), 7.32 (d, 1H), 6.81 (d, 1H), 4.68 (t, 2H), 3.26 (t, 2H).

Step 2

(5-bromo-2-chloro-phenyl)-(2,3-dihydrobenzofuran-5-yl)methanol (5-bromo-2-chloro-phenyl)-(2,3-dihydrobenzofuran-5-yl) methanone 5b (10.47 g, 31.0 mmol) was dissolved in 100 mL of mixed solution (THF and MeOH, v:v=1:1) and cooled to 0° C., followed by addition of sodium borohydride (2.35 g, 62.0 mmol) in batch. The reaction mixture was stirred for 30 minutes at 0° C. Thereafter, the reaction mixture was concentrated under reduced pressure after 20 mL acetone were added. The resulting residue was dissolved in 250 mL ethyl acetate and partitioned. The organic extract was washed with water (100 mL×2), combined, dried over anhydrous magnesium sulfate, and filtered. The filtrate was concentrated under reduced pressure to obtain the title compound (5-bromo-2-chloro-phenyl)-(2,3-dihydrobenzofuran-5-yl)methanol 5c (10.5 g, pale yellow grease), yield: 99.7%. 1H NMR (400 MHz, CDCl3): δ 7.88 (d, 1H), 7.34 (dd, 1H), 7.18 (d, 1H), 7.16 (s, 1H), 7.11 (dd, 1H), 6.73 (d, 1H), 6.05 (s, 1H), 4.56 (t, 2H), 3.18 (t, 2H), 2.27 (s, 1H).

Step 3

5-[(5-bromo-2-chloro-phenyl)methyl]-2,3-dihydrobenzofuran (5-bromo-2-chloro-phenyl)-(2,3-dihydrobenzofuran-5-yl) methanol 5c (10.5 g, 30.9 mmol) was dissolved in 100 mL dichloromethane, followed by addition of triethylsilane (14.8 mL, 92.7 mmol) and dropwise addition of boron trifluoride etherate (7.8 mL, 61.8 mmol). The reaction mixture was stirred for 16 hours. Thereafter, the reaction mixture was concentrated under reduced pressure and the resulting residue was purified by silica gel chromatography with elution system D to obtain the title compound 5-[(5-bromo-2-chloro-phenyl)methyl]-2,3-dihydrobenzo-furan 5d (10.0 g, pale yellow grease), yield: 100%. 1H NMR (400 MHz, CDCl3): δ 7.29-7.21 (m, 3H), 7.00 (s, 1H), 6.93 (d, 1H), 6.73 (d, 1H), 4.56 (t, 2H), 3.98 (s, 2H), 3.18 (t, 2H).

Step 4

(2S,3R,4S,5S,6R)-2-[4-chloro-3-(2,3-dihydrobenzo-furan-5-ylmethyl)phenyl]-6-(hydroxymethyl)-2-methoxy-tetrahydropyran-3,4,5-triol 5-[(5-bromo-2-chloro-phenyl)methyl]-2,3-dihydrobenzo-furan 5d (10.0 g, 30.9 mmol) was dissolved in 90 mL of mixed solution (THF and toluene, v:v=1:2) and cooled to −78° C., followed by dropwise addition of a solution of nBuLi in n-hexane (14.83 mL, 37.1 mmol). After stirring for 1 hour at −78° C., a solution of (3R,4S,5R,6R)-3,4,5-tris(trimethylsi-lyloxy)-6-(trimethylsilyloxymethyl)tetrahydropyran-2-one 2f (15.87 g, 33.9 mmol) in toluene (90 mL) was dropwise added before the reaction mixture was stirred for 3 hours at −78° C. A solution of 0.6 M methanesulfonic acid in methanol (103 mL) was added before the reaction mixture was stirred for 16 hours. Thereafter, the reaction was concentrated under reduced pressure after 100 mL saturated sodium carbonate solution were added. The residue was extracted with ethyl acetate (100 mL×3) after 50 mL saturated sodium chloride solution were added and the organic extract was combined, dried over anhydrous magnesium sulfate, and filtered. The filtrate was concentrated under reduced pressure and the resulting residue was purified by silica gel chromatography with elution system E to obtain the title compound (2S,3R, 4S,5S,6R)-2-[4-chloro-3-(2,3-dihydrobenzofuran-5-ylm-ethyl)phenyl]-6-(hydroxymethyl)-2-methoxy-tetrahydropy-ran-3,4,5-triol 5e (6.3 g, white solid), yield: 46.7%. 1H NMR (400 MHz, CD3OD): δ 7.53 (d, 1H), 7.45 (dd, 1H), 7.35 (d, 1H), 7.03 (s, 1H), 6.91 (d, 1H), 6.60 (d, 1H), 4.48 (t, 2H), 4.13-3.91 (m, 3H), 3.84-3.73 (m, 2H), 3.61-3.56 (m, 1H), 3.44-3.39 (m, 1H), 3.11 (dd, 3H), 3.07 (s, 3H).

Step 5

(2S,3R,4S,5S,6R)-6-[(tert-butyl(dimethyl)silyl) oxymethyl]-2-[4-chloro-3-(2,3-dihydrobenzofuran-5-ylmethyl)phenyl]-2-methoxy-tetrahydropyran-3,4, 5-triol (2S,3R,4S,5S,6R)-2-[4-chloro-3-(2,3-dihydrobenzofu-ran-5-ylmethyl)phenyl]-6-(hydroxymethyl)-2-methoxy-tet-rahydropyran-3,4,5-triol 5e (6.3 g, 14.44 mmol) was dissolved in 60 mL pyridine, followed by addition of 4-dimethylamino pyridine (353 mg, 2.89 mmol) and tert-butyl-dimethyl-chloro-silane (2.61 g, 17.32 mmol) in turn. The reaction mixture was stirred for 16 hours and concentrated under reduced pressure. The resulting residue was dissolved in 200 mL ethyl acetate and partitioned. The organic extract was washed with water (50 mL) and saturated sodium chloride solution (50 mL), combined, dried over anhydrous magnesium sulfate, and filtered. The filtrate was concentrated under reduced pressure to obtain the title compound (2S,3R, 4S,5S,6R)-6-[(tert-butyl(dimethyl)silyl)oxymethyl]-2-[4-chloro-3-(2,3-dihydrobenzofuran-5-ylmethyl)phenyl]-2-methoxy-tetrahydropyran-3,4,5-triol 5f (7.96 g, pale yellow solid), which was used directly in the next step without purification.

Step 6

[[(2R,3R,4S,5R,6S)-3,4,5-tribenzyloxy-6-[4-chloro-3-(2,3-dihydrobenzofuran-5-ylmethyl)phenyl]-6-methoxy-tetrahydropyran-2-yl]tert-butyl-dimethyl-methoxy]silane (2S,3R,4S,5S,6R)-6-[(tert-butyl(dimethyl)silyl)oxymethyl]-2-[4-chloro-3-(2,3-dihydrobenzofuran-5-ylmethyl)phenyl]-2-methoxy-tetrahydropyran-3,4,5-triol 5f (7.96 g, 14.4 mmol) was dissolved in 80 mL DMF and cooled to 0° C., followed by addition of 60% NaH (2.89 g, 72.21 mmol). Then the reaction mixture was warmed to room temperature and stirred for 15 minutes. Thereafter, benzyl bromide (8.58 mL, 72.21 mmol) was added before the mixture was stirred for 16 hours. The reaction mixture was concentrated under reduced pressure after 10 mL methanol were added. Followed by addition of 200 mL ethyl acetate, the reaction mixture was washed with water (50 mL×2) and the organic extract was combined, dried over anhydrous magnesium sulfate, and filtered. The filtrate was concentrated under reduced pressure to obtain the title compound [[(2R,3R,4S,5R,6S)-3,4,5-tribenzyloxy-6-[4-chloro-3-(2,3-dihydrobenzofuran-5-ylmethyl)phenyl]-6-methoxy-tetrahydropyran-2-yl]tert-butyl-dimethyl-methoxy]silane 5g (11.86 g, black grease), which was used directly in the next step without purification.

Step 7

[(2R,3R,4S,5R,6S)-3,4,5-tribenzyloxy-6-[4-chloro-3-(2,3-dihydrobenzofuran-5-ylmethyl)phenyl]-6-methoxy-tetrahydropyran-2-yl]methanol

[[(2R,3R,4S,5R,6S)-3,4,5-tribenzyloxy-6-[4-chloro-3-(2,3-dihydrobenzofuran-5-ylmethyl)phenyl]-6-methoxy-tetrahydropyran-2-yl]tert-butyl-dimethyl-methoxy]silane 5g (11.86 g, 14.4 mmol) was dissolved in 100 mL methanol, followed by addition of acetyl chloride (152 μL, 2.17 mmol). The reaction mixture was stirred for 1 hour and concentrated under reduced pressure and the resulting residue was purified by silica gel chromatography with elution system D to obtain the title compound [(2R,3R,4S,5R,6S)-3,4,5-tribenzyloxy-6-[4-chloro-3-(2,3-dihydrobenzofuran-5-ylmethyl)phenyl]-6-methoxy-tetrahydropyran-2-yl]methanol 5h (9.0 g, yellow liquid), yield: 88.1%.

Step 8

(2S,3S,4S,5R,6S)-3,4,5-tribenzyloxy-6-[4-chloro-3-(2,3-dihydrobenzofuran-5-ylmethyl)phenyl]-6-methoxy-tetrahydropyran-2-carbaldehyde Oxalyl chloride (0.76 mL, 8.91 mmol) was dissolved in 10 mL methylene chloride and cooled to −78° C., followed by dropwise addition of 10 mL of mixed solution (methylene chloride and dimethyl sulfoxide, v:v=10:0.85). The reaction mixture was stirred for 15 minutes. Then 25 mL solution of [(2R,3R,4S,5R,6S)-3,4,5-tribenzyloxy-6-[4-chloro-3-(2,3-dihydrobenzofuran-5-ylmethyl)phenyl]-6-methoxy-tetrahydropyran-2-yl]methanol 5h (4.2 g, 5.94 mmol) in methylene chloride was dropwise added before the mixture was stirred for 40 minutes. The reaction mixture was warmed to room temperature and stirred for 2 hours after triethylamine (4.29 mL, 29.69 mmol) was dropwise added. Thereafter, the reaction mixture was partitioned after 35 mL 1 M hydrochloric acid were added, the organic extract was washed with saturated sodium chloride solution (35 mL×2), combined, dried over anhydrous magnesium sulfate, and filtered. The filtrate was concentrated under reduced pressure to obtain the title compound (2S,3S,4S,5R,6S)-3,4,5-tribenzyloxy-6-[4-chloro-3-(2,3-dihydrobenzofuran-5-ylmeth-yl)phenyl]-6-methoxy-tetrahydropyran-2-carbaldehyde 5I (4.19 g, pale yellow grease), which was used directly in the next step without purification.

Step 9

(2S,3S,4S,5R,6S)-3,4,5-tribenzyloxy-6-[4-chloro-3-(2,3-dihydrobenzofuran-5-ylmethyl)phenyl]-2-(hydroxymethyl)-6-methoxy-tetrahydropyran-2-carbaldehyde (2S,3S,4S,5R,6S)-3,4,5-tribenzyloxy-6-[4-chloro-3-(2,3-dihydrobenzofuran-5-ylmethyl)phenyl]-6-methoxy-tetrahydropyran-2-carbaldehyde 5I (4.19 g, 5.9 mmol) was dissolved in 45 mL 1,4-dioxane, followed by addition of 9.6 mL 37% formaldehyde solution and dropwise addition of 17.82 mL 1 M sodium hydroxide solution. The reaction mixture was stirred for 16 hours at 70° C. Thereafter, the reaction mixture was concentrated under reduced pressure and partitioned after 100 mL ethyl acetate and 50 mL saturated sodium chloride solution were added. The aqueous phase was extracted with ethyl acetate (100 mL×2) and the organic extract was combined, dried over anhydrous magnesium sulfate, and filtered. The filtrate was concentrated under reduced pressure to obtain the title compound (2S,3S,4S,5R,6S)-3,4,5-tribenzyloxy-6-[4-chloro-3-(2,3-dihydrobenzofuran-5-ylmethyl)phenyl]-2-(hydroxymethyl)-6-methoxy-tetrahydropyran-2-carbaldehyde 5j (4.36 g, pale yellow grease), which was used directly in the next step without purification.

Step 10

[(3S,4S,5R,6S)-3,4,5-tribenzyloxy-6-[4-chloro-3-(2,3-dihydrobenzofuran-5-ylmethyl)phenyl]-2-(hydroxymethyl)-6-methoxy-tetrahydropyran-2-yl]methanol (2S,3S,4S,5R,6S)-3,4,5-tribenzyloxy-6-[4-chloro-3-(2,3-dihydrobenzofuran-5-ylmethyl)phenyl]-2-(hydroxymethyl)-6-methoxy-tetrahydropyran-2-carbaldehyde 5j (4.36 g, 5.93 mmol) was dissolved in 50 mL of mixed solution (THF and MeOH, v:v=1:1), followed by addition of sodium borohydride (0.45 g, 11.9 mmol). The reaction mixture was stirred for 30 minutes. Thereafter, the reaction mixture was concentrated under reduced pressure and the resulting residue was purified by silica gel chromatography with elution system D to obtain the title compound [(3S,4S,5R,6S)-3,4,5-tribenzyloxy-6-[4-chloro-3-(2,3-dihydrobenzofuran-5-ylmethyl)phenyl]-2-(hydroxymethyl)-6-methoxy-tetrahydropyran-2-yl]methanol 5k (1.26 g, white solid), yield: 28.8%. 1H NMR (400 MHz, CD3OD): δ 7.53 (dd, 1H), 7.44 (d, 1H), 7.35 (d, 1H), 7.31-7.26 (m, 5H), 7.25-7.18 (m, 8H), 7.04-7.02 (m, 2H), 6.90 (s, 1H), 6.80 (d, 1H), 6.54 (d, 1H), 4.90-4.79 (m, 4H), 4.73 (d, 1H), 4.54 (d, 1H), 4.46-4.41 (m, 2H), 4.20 (t, 1H), 4.10-4.00 (m, 5H), 3.88 (dd, 2H), 3.74 (d, 1H), 3.15 (s, 3H), 3.06-3.00 (m, 2H).

Step 11

[(1S,2S,3S,4R,5S)-2,3,4-tribenzyloxy-5-[4-chloro-3-(2,3-dihydrobenzofuran-5-ylmethyl)phenyl]-6,8-dioxabicyclo[3.2.1]octan-1-yl]methanol

[(3S,4S,5R,6S)-3,4,5-tribenzyloxy-6-[4-chloro-3-(2,3-dihydrobenzofuran-5-ylmethyl)phenyl]-2-(hydroxymethyl)-6-methoxy-tetrahydropyran-2-yl]methanol 5k (1.2 g, 1.63 mmol) was dissolved in 25 mL dichloromethane, followed by dropwise addition of trifluoroacetic acid (0.5 mL, 6.52 mmol). The reaction mixture was stirred for 1.5 hours. Thereafter, the reaction mixture was concentrated under reduced pressure and the resulting residue was purified by silica gel chromatography with elution system D to obtain the title compound [(1S,2S,3S,4R,5S)-2,3,4-tribenzyloxy-5-[4-chloro-3-(2,3-dihydrobenzofuran-5-ylmethyl)phenyl]-6,8-dioxabicyclo[3.2.1]octan-1-yl]methanol 5m (580 mg, white solid), yield: 50.4%. MS m/z (ESI): 722.3 [M+18]; 1H NMR (400 MHz, CD3OD): δ 7.48-7.39 (m, 3H), 7.35-7.23 (m, 10H), 7.21-7.11 (m, 3H), 6.97 (s, 1H), 6.90 (d, 1H), 6.84 (d, 2H), 6.57 (d, 1H), 4.83 (d, 4H), 4.44 (t, 2H), 4.23 (m, 2H), 4.07-4.00 (m, 3H), 3.95 (dd, 1H), 3.87 (d, 1H), 3.79 (d, 1H), 3.73-3.69 (m, 2H), 3.56 (d, 1H), 3.01 (t, 2H).

Step 12

(1S,2S,3S,4R,5S)-5-[4-chloro-3-(2,3-dihydrobenzo-furan-5-ylmethyl)phenyl]-1-(hydroxymethyl)-6,8-dioxabicyclo[3.2.1]octane-2,3,4-triol

[(1S,2S,3S,4R,5S)-2,3,4-tribenzyloxy-5-[4-chloro-3-(2, 3-dihydrobenzofuran-5-ylmethyl)phenyl]-6,8-dioxabicyclo [3.2.1]octan-1-yl]methanol 5m (100 mg, 0.14 mmol) was dissolved in 5 mL of mixed solution (THF and MeOH, v:v=1: 1), followed by addition of o-dichlorobenzene (208 mg, 1.42 mmol) and Palladium/carbon (10 mg, 10%). The mixture was exchanged with H2 three times and stirred for 1.5 hours, filtered and the filtrate was concentrated under reduced pressure. The resulting residue was purified by thin layer chromatography with developing solvent system A to obtain the title compound (1S,2S,3S,4R,5S)-5-[4-chloro-3-(2,3-dihydrobenzofuran-5-ylmethyl)phenyl]-1-(hydroxymethyl)-6,8-dioxabicyclo[3.2.1]octane-2,3,4-triol 5 (58 mg, white solid), yield: 93.5%. MS m/z (ESI): 435.1 [M+1]; 1H NMR (400 MHz, CD3OD): δ 7.47 (d, 1H), 7.39-7.35 (m, 2H), 7.04 (s, 1H), 6.93 (d, 1H), 6.62 (d, 1H), 4.50 (t, 2H), 4.17 (d, 1H), 4.03 (s, 2H), 3.88-3.79 (m, 2H), 3.71-3.65 (m, 2H), 3.62-3.56 (m, 2H), 3.15 (t, 2H).

Example 6

(1S,2S,3S,4R,5S)-5-[4-chloro-3-[[4-(trifluoromethoxy)phenyl]methyl]phenyl]-1-(hydroxymethyl)-6,8-dioxabicyclo[3.2.1]octane-2,3,4-triol

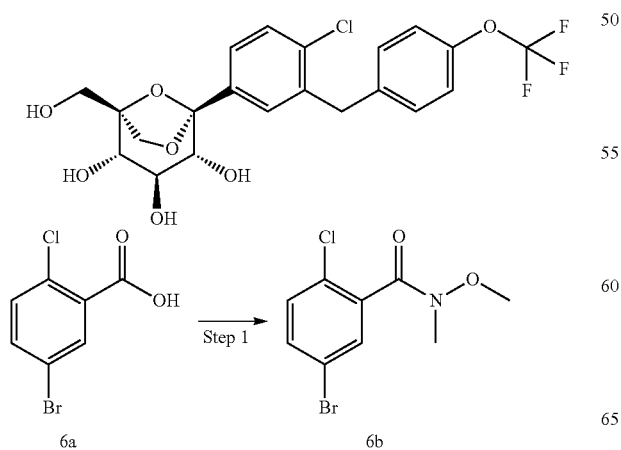

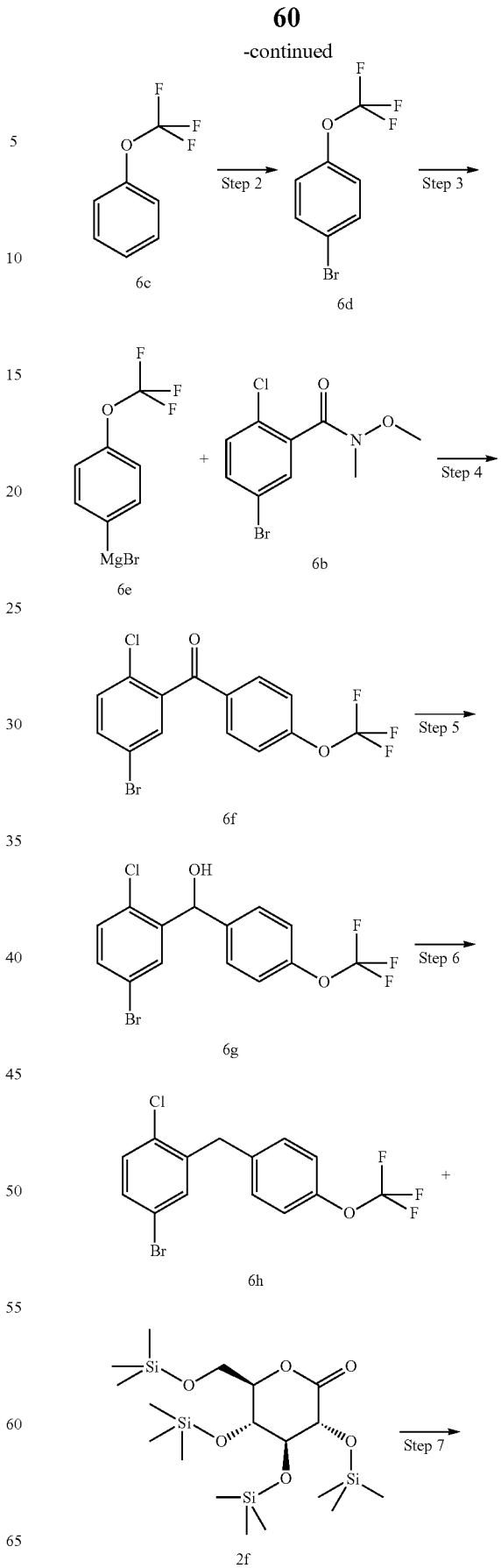

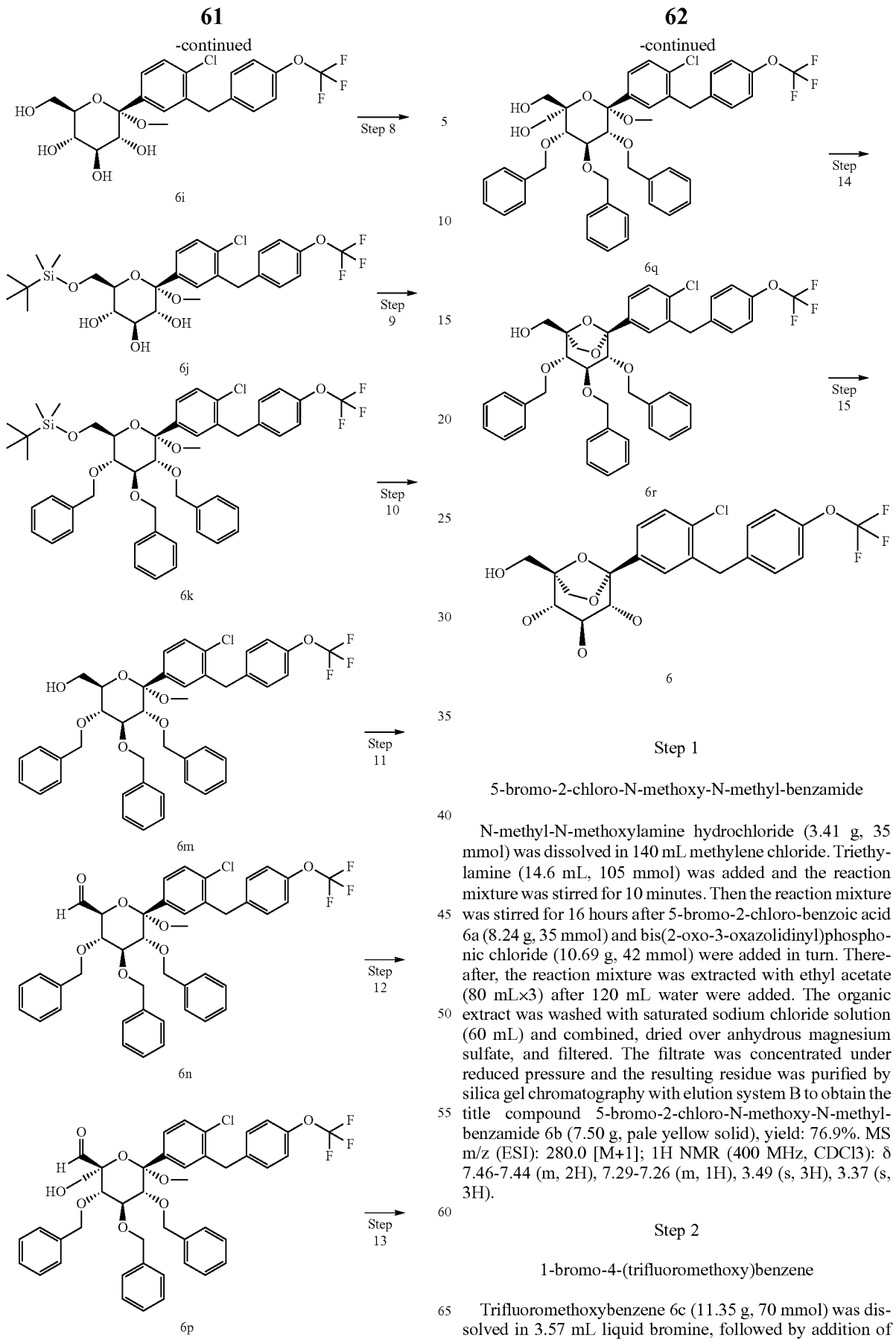

Step 1

5-bromo-2-chloro-N-methoxy-N-methyl-benzamide

N-methyl-N-methoxylamine hydrochloride (3.41 g, 35 mmol) was dissolved in 140 mL methylene chloride. Triethylamine (14.6 mL, 105 mmol) was added and the reaction mixture was stirred for 10 minutes. Then the reaction mixture was stirred for 16 hours after 5-bromo-2-chloro-benzoic acid 6a (8.24 g, 35 mmol) and bis(2-oxo-3-oxazolidinyl)phosphonic chloride (10.69 g, 42 mmol) were added in turn. Thereafter, the reaction mixture was extracted with ethyl acetate (80 mL×3) after 120 mL water were added. The organic extract was washed with saturated sodium chloride solution (60 mL) and combined, dried over anhydrous magnesium sulfate, and filtered. The filtrate was concentrated under reduced pressure and the resulting residue was purified by silica gel chromatography with elution system B to obtain the title compound 5-bromo-2-chloro-N-methoxy-N-methyl-benzamide 6b (7.50 g, pale yellow solid), yield: 76.9%. MS m/z (ESI): 280.0 [M+1]; 1H NMR (400 MHz, CDCl3): δ 7.46-7.44 (m, 2H), 7.29-7.26 (m, 1H), 3.49 (s, 3H), 3.37 (s, 3H).

Step 2

1-bromo-4-(trifluoromethoxy)benzene

Trifluoromethoxybenzene 6c (11.35 g, 70 mmol) was dissolved in 3.57 mL liquid bromine, followed by addition of iron (0.24 g). The reaction mixture was stirred for 16 hours at 100° C. 450 mL of dichloromethane were added and the organic extract was washed with 6 M hydrochloric acid (140 mL), 10% sodium hydrogen sulfite solution (140 mL) and saturated sodium chloride solution (140 mL), combined, dried over anhydrous magnesium sulfate, and filtered. The filtrate was concentrated under reduced pressure to obtain the title compound 1-bromo-4-(trifluoromethoxy)benzene 6d (14.1 g, yellow solid), yield: 83.8%. 1H NMR (400 MHz, CDCl3): δ 7.54-7.50 (m, 2H), 7.11-7.09 (m, 2H).

Step 3

1-bromo-magnesium-4-(trifluoromethoxy)benzene

Magnesium (0.12 g, 5 mmol) and iodine (I2, catalytic) were added into the reaction flask, followed by dropwise addition of a solution (5 mL) of 1-bromo-4-(trifluoromethoxy)benzene 6d (1.2 g, 5 mmol) in THF. The reaction mixture was refluxed for 1 hour to obtain the title compound 1-bromo-magnesium-4-(trifluoromethoxy)benzene 6e (1.32 g), which was used directly in the next step without purification.

Step 4

(5-bromo-2-chloro-phenyl)-[4-(trifluoromethoxy) phenyl]methanone 5-bromo-2-chloro-N-methoxy-N-methyl-benzamide 6b (5.16 g, 18.5 mmol) was dissolved in 50 mL THF, followed by dropwise addition of 1-bromo-magnesium-4-(trifluoromethoxy)benzene 6e (13.21 g, 49.8 mmol). The reaction mixture was stirred for 2 hours. Thereafter, the reaction mixture was partitioned after 200 mL saturated sodium chloride solution, 200 mL water and 150 mL ethyl acetate were added. The aqueous phase was extracted with ethyl acetate (150 mL) and the organic extract was washed with saturated sodium chloride solution (200 mL), combined, dried over anhydrous magnesium sulfate, and filtered. The filtrate was concentrated under reduced pressure. The resulting residue was purified by silica gel chromatography with elution system B to obtain the title compound (5-bromo-2-chloro-phenyl)-[4-(trifluoromethoxy)phenyl]methanone 6f (4.08 g, pale yellow solid), yield: 58.1%. MS m/z (ESI): 380.9 [M+1]; 1H NMR (400 MHz, CDCl3): δ 7.88-7.84 (m, 2H), 7.58 (dd, 1H), 7.51 (d, 1H), 7.35 (d, 1H), 7.32-7.30 (m, 2H).

Step 5

(5-bromo-2-chloro-phenyl)-[4-(trifluoromethoxy) phenyl]methanol (5-bromo-2-chloro-phenyl)-[4-(trifluoromethoxy)phenyl] methanone 6f (4.35 g, 11.5 mmol) was dissolved in 40 mL of mixed solution (THF and MeOH, v:v=1:1) and cooled to 0° C., followed by addition of sodium borohydride (0.87 g, 23.0 mmol) in batch. The reaction mixture was stirred for 30 minutes at 0° C. Thereafter, the reaction mixture was concentrated under reduced pressure after 10 mL acetone were added. The reaction mixture was partitioned after 100 mL ethyl acetate and 50 mL water were added and the organic extract was washed with saturated sodium chloride solution (50 mL×2), combined, dried over anhydrous magnesium sulfate, and filtered. The filtrate was concentrated under reduced pressure to obtain the title compound (5-bromo-2-chloro-phenyl)-[4-(trifluoromethoxy)phenyl]methanol 6g (4.4 g, pale yellow grease), which was used directly in the next step without purification. 1H NMR (400 MHz, CDCl3): δ 7.80 (d, 1H), 7.43-7.40 (m, 2H), 7.36 (dd, 1H), 7.20 (t, 3H), 6.16 (s, 1H).

Step 6

4-bromo-1-chloro-2-[[4-(trifluoromethoxy)phenyl] methyl]benzene (5-bromo-2-chloro-phenyl)-[4-(trifluoromethoxy)phenyl] methanol 6g (4.37 g, 11.5 mmol) was dissolved in 35 mL dichloromethane, followed by addition of triethyl silane (5.49 mL, 34.4 mmol) and dropwise addition of boron trifluoride etherate (2.9 mL, 22.9 mmol). The reaction mixture was stirred for 16 hours. Thereafter, the reaction mixture was concentrated under reduced pressure and partitioned after 20 mL saturated sodium bicarbonate solution were added. The aqueous phase was extracted with dichloromethane (25 mL×3) and the organic extract was combined, dried over anhydrous magnesium sulfate, and filtered. The filtrate was concentrated under reduced pressure. The resulting residue was purified by silica gel chromatography with elution system C to obtain the title compound 4-bromo-1-chloro-2-[[4-(trifluoro-methoxy)phenyl]methyl]benzene 6h (3.0 g, colourless grease), yield: 71.6%. 1H NMR (400 MHz, CDCl3): δ 7.33-7.29 (m, 2H), 7.26-7.24 (m, 1H), 7.21-7.18 (m, 2H), 7.15 (d, 2H), 4.06 (s, 2H).

Step 7

(2S,3R,4S,5S,6R)-2-[4-chloro-3-[[4-(trifluoromethoxy)phenyl]methyl]phenyl]-6-(hydroxymethyl)-2-methoxy-tetrahydropyran-3,4,5-triol 4-bromo-1-chloro-2-[[4-(trifluoromethoxy)phenyl]methyl]benzene 6h (2.33 g, 6.38 mmol) was dissolved in 40 mL of mixed solution (THF and n-hexane, v:v=1:3) and cooled to −78° C., followed by dropwise addition of a solution of nBuLi in n-hexane (3.83 mL, 9.57 mmol). After stirring for 1.5 hours at −78° C., a solution (30 mL) of (3R,4S,5R,6R)-3,4,5-tris (trimethylsilyloxy)-6-(trimethylsilyloxymethyl)tetrahydropyran-2-one 2f (4.47 g, 9.57 mmol) in mixed solution (THF and n-hexane, v:v=1:3) was dropwise added before the reaction mixture was stirred for 2 hours at −78° C. A solution (32 mL) of 0.6 M methanesulfonic acid in methanol was added before the reaction mixture was warmed and stirred for 16 hours at room temperature. Thereafter, the reaction mixture was partitioned after 150 mL of saturated sodium carbonate solution were added. The aqueous phase was extracted with ethyl acetate (100 mL×3) and the organic extracts were combined, dried over anhydrous magnesium sulfate, and filtered. The filtrate was concentrated under reduced pressure. The resulting residue was purified by silica gel chromatography with elution system A to obtain the title compound (2S,3R, 4S,5S,6R)-2-[4-chloro-3-[[4-(trifluoromethoxy)phenyl]methyl]phenyl]-6-(hydroxymethyl)-2-methoxy-tetrahydropyran-3,4,5-triol 61 (1.38 g, white solid), yield: 45.2%. 1H NMR (400 MHz, CD3OD): δ 7.61 (d, 1H), 7.51 (dd, 1H), 7.40 (d, 1H), 7.31-7.29 (m, 2H), 7.17 (d, 2H), 4.23-4.12 (m, 2H), 3.94 (d, 1H), 3.86-3.75 (m, 2H), 3.95-3.59 (m, 2H), 3.47-3.42 (m, 1H), 3.10 (s, 3H).

Step 8

(2S,3R,4S,5S,6R)-6-[(tert-butyl(dimethyl)silyl) oxymethyl]-2-[4-chloro-3-[[4-(trifluoromethoxy) phenyl]methyl]phenyl]-2-methoxy-tetrahydropyran-3,4,5-triol (2S,3R,4S,5S,6R)-2-[4-chloro-3-[[4-(trifluoromethoxy) phenyl]methyl]phenyl]-6-(hydroxymethyl)-2-methoxy-tetrahydropyran-3,4,5-triol 61 (1.33 g, 2.78 mmol) was dissolved in 12 mL pyridine, followed by addition of 4-dimethylamino pyridine (67.93 mg, 0.55 mmol) and TBSCl (0.50 g, 3.34 mmol) in turn. The reaction mixture was stirred for 16 hours. Thereafter, the reaction mixture was concentrated under reduced pressure and partitioned after 75 mL ethyl acetate and 75 mL water were added. The aqueous phase was extracted with ethyl acetate (50 mL×2) and the organic extracts were combined, dried over anhydrous magnesium sulfate, and filtered. The filtrate was concentrated under reduced pressure to obtain the title compound (2S,3R,4S,5S,6R)-6-[(tert-butyl(dimethyl)silyl)oxymethyl]-2-[4-chloro-3-[[4-(trifluoromethoxy)phenyl]methyl]phenyl]-2-methoxy-tetrahydropyran-3,4,5-triol 6j (1.60 g, white solid), yield: 97.6%. 1H NMR (400 MHz, CD3OD): δ 7.55 (d, 1H), 7.46 (d, 1H), 7.41 (d, 1H), 7.26 (d, 2H), 7.17 (d, 2H), 4.17 (s, 2H), 4.04 (d, 1H), 3.92-3.88 (m, 1H), 3.77 (t, 1H), 3.61-3.59 (m, 1H), 3.09 (s, 3H).

Step 9

[[(2R,3R,4S,5R,6S)-3,4,5-tribenzyloxy-6-[4-chloro-3-[[4-(trifluoromethoxy)phenyl]methyl]phenyl]-6-methoxy-tetrahydropyran-2-yl]methoxy]tert-butyl-dimethyl-silane (2S,3R,4S,5S,6R)-6-[(tert-butyl(dimethyl)silyl)oxymethyl]-2-[4-chloro-3-[[4-(trifluoromethoxy)phenyl]methyl]phenyl]-2-methoxy-tetrahydropyran-3,4,5-triol 6j (1.60 g, 2.69 mmol) was dissolved in 15 mL DMF and cooled to 0° C., followed by addition of 60% NaH (0.54 g, 13.5 mmol). Then the reaction mixture was warmed and stirred for 15 minutes at room temperature before benzyl bromide (1.6 mL, 13.5 mmol) was added. After stirring for 16 hours, the reaction mixture was concentrated under reduced pressure after 5 mL methanol were added. Then the resulting residue was dissolved in ethyl acetate (100 mL) and washed with water (50 mL×2). The organic extract was combined, dried over anhydrous magnesium sulfate, and filtered. The filtrate was concentrated under reduced pressure to obtain the title compound [[(2R,3R,4S,5R,6S)-3,4,5-tribenzyloxy-6-[4-chloro-3-[[4-(trifluoromethoxy)phenyl]methyl]phenyl]-6-methoxy-tetrahydropyran-2-yl]methoxy]tert-butyl-dimethyl-silane 6k (2.32 g, yellow grease), which was used directly in the next step without purification.

Step 10

[(2R,3R,4S,5R,6S)-3,4,5-tribenzyloxy-6-[4-chloro-3-[[4-(trifluoromethoxy)phenyl]methyl]phenyl]-6-methoxy-tetrahydropyran-2-yl]methanol

[[(2R,3R,4S,5R,6S)-3,4,5-tribenzyloxy-6-[4-chloro-3-[[4-(trifluoromethoxy)phenyl]methyl]phenyl]-6-methoxy-tetrahydropyran-2-yl]methoxy]tert-butyl-dimethyl-silane 6k (2.32 g, 2.69 mmol) was dissolved in 12 mL methanol, followed by addition of acetyl chloride (16 μL, 0.40 mmol). The reaction mixture was stirred for 1.5 hours. Thereafter, the reaction mixture was concentrated under reduced pressure and the resulting residue was purified by silica gel chromatography with elution system B to obtain the title compound [(2R,3R,4S,5R,6S)-3,4,5-tribenzyloxy-6-[4-chloro-3-[[4-(trifluoromethoxy)phenyl]methyl]phenyl]-6-methoxy-tetrahydropyran-2-yl]methanol 6m (1.22 g, pale yellow grease), yield: 60.7%. 1H NMR (400 MHz, CD3OD): δ 7.54-7.52 (m, 2H), 7.41 (d, 1H), 7.32-7.22 (m, 13H), 7.18 (d, 2H), 7.08-7.04 (m, 4H), 4.91-4.85 (m, 3H), 4.75 (d, 1H), 4.52 (d, 1H), 4.17-4.09 (m, 3H), 4.00 (d, 1H), 3.94-3.83 (m, 3H), 3.75-3.69 (m, 2H), 3.09 (s, 3H).

Step 11

(2S,3S,4S,5R,6S)-3,4,5-tribenzyloxy-6-[4-chloro-3-[[4-(trifluoromethoxy)phenyl]methyl]phenyl]-6-methoxy-tetrahydropyran-2-carbaldehyde Oxalyl chloride (0.21 mL, 2.45 mmol) was dissolved in 5 mL dichloromethane and cooled to −78° C. The mixture was stirred for 15 minutes after 5 mL solution of dimethyl sulfoxide (0.24 mL, 3.26 mmol) in dichloromethane were added. Then 10 mL solution of [(2R,3R,4S,5R,6S)-3,4,5-tribenzyloxy-6-[4-chloro-3-[[4-(trifluoromethoxy)phenyl]methyl]phenyl]-6-methoxy-tetrahydropyran-2-yl]methanol 6m (1.22 g, 1.63 mmol) in dichloromethane were added before the mixture was stirred for 40 minutes. Then the reaction mixture was warmed and stirred for 1.5 hours at room temperature after triethylamine (1.18 mL, 8.15 mmol) was added and partitioned after 10 mL 1 M hydrochloric acid were added. The organic extract was washed with saturated sodium chloride solution (10 mL×2) and combined, dried over anhydrous magnesium sulfate, and filtered. The filtrate was concentrated under reduced pressure to obtain the title compound (2S,3S,4S,5R,6S)-3,4,5-tribenzyloxy-6-[4-chloro-3-[[4-(trifluoromethoxy)phenyl]methyl]phenyl]-6-methoxy-tetrahydropyran-2-carbaldehyde 6n (1.21 g, yellow grease), which was used directly in the next step without purification.

Step 12

(2S,3S,4S,5R,6S)-3,4,5-tribenzyloxy-6-[4-chloro-3-[[4-(trifluoromethoxy)phenyl]methyl]phenyl]-2-(hydroxymethyl)-6-methoxy-tetrahydropyran-2-carbaldehyde (2S,3S,4S,5R,6S)-3,4,5-tribenzyloxy-6-[4-chloro-3-[[4-(trifluoromethoxy)phenyl]methyl]phenyl]-6-methoxy-tetrahydropyran-2-carbaldehyde 6n (1.21 g, 1.63 mmol) was dissolved in 12 mL 1,4-dioxane, followed by addition of 2.65 mL 37% formaldehyde solution and dropwise addition of 4.89 mL 1 M sodium hydroxide. The reaction mixture was stirred for 16 hours at 70° C. Thereafter, the reaction mixture was concentrated under reduced pressure and was partitioned after 30 mL of saturated sodium chloride solution were added. The aqueous phase was extracted with ethyl acetate (30 mL×3) and the organic extract was combined, dried over anhydrous magnesium sulfate, and filtered. The filtrate was concentrated under reduced pressure to obtain the title compound (2S,3S,4S,5R,6S)-3,4,5-tribenzyloxy-6-[4-chloro-3-[[4-(trifluoromethoxy)phenyl]methyl]phenyl]-2-(hydroxymethyl)-6-methoxy-tetrahydro-pyran-2-carbaldehyde 6p (1.27 g, pale yellow grease), which was used directly in the next step without purification.

Step 13

[(3S,4S,5R,6S)-3,4,5-tribenzyloxy-6-[4-chloro-3-[[4-(trifluoromethoxy)phenyl]methyl]phenyl]-2-(hydroxymethyl)-6-methoxy-tetrahydropyran-2-yl]methanol (2S,3S,4S,5R,6S)-3,4,5-tribenzyloxy-6-[4-chloro-3-[[4-(trifluoromethoxy)phenyl]methyl]phenyl]-2-(hydroxymethyl)-6-methoxy-tetrahydropyran-2-carbaldehyde 6p (1.27 g, 1.63 mmol) was dissolved in 10 mL of mixed solution (THF and MeOH, v:v=1:1) and followed by addition of sodium borohydride (0.12 g, 3.26 mmol) in batch. The reaction mixture was stirred for 1.5 hours. Thereafter, the reaction mixture was concentrated under reduced pressure and was partitioned after 30 mL of ethyl acetate were added. The organic extract was washed with saturated sodium chloride solution (15 mL×2), combined, dried over anhydrous magnesium sulfate, and filtered. The filtrate was concentrated under reduced pressure and the resulting residue was purified by silica gel chromatography with elution system E to obtain the title compound [(3S,4S,5R,6S)-3,4,5-tribenzyloxy-6-[4-chloro-3-[[4-(trifluoromethoxy)phenyl]methyl]phenyl]-2-(hydroxymethyl)-6-methoxy-tetrahydropyran-2-yl]methanol 6q (400 mg, white solid), yield: 31.5%. 1H NMR (400 MHz, CD3OD): δ 7.58 (dd, 1H), 7.54 (d, 1H), 7.39 (d, 1H), 7.31-7.24 (m, 13H), 7.16 (d, 2H), 7.11-7.06 (m, 4H), 4.92 (d, 1H), 4.76 (d, 1H), 4.66-4.59 (m, 1H), 4.27-4.22 (m, 2H), 4.17-4.10 (m, 2H), 4.07-4.04 (m, 3H), 3.99-3.95 (m, 2H), 3.77 (d, 1H), 3.65-3.60 (m, 2H), 3.35 (s, 2H), 3.18 (s, 3H).

Step 14

[(1S,2S,3S,4R,5S)-2,3,4-tribenzyloxy-5-[4-chloro-3-[[4-(trifluoromethoxy)phenyl]methyl]phenyl]-6,8-dioxabicyclo[3.2.1]octan-1-yl]methanol

[(3S,4S,5R,6S)-3,4,5-tribenzyloxy-6-[4-chloro-3-[[4-(trifluoromethoxy)phenyl]methyl-]phenyl]-2-(hydroxymethyl)-6-methoxy-tetrahydropyran-2-yl]methanol 6q (400 mg, 0.51 mmol) was dissolved in 10 mL dichloromethane, followed by addition of trifluoroacetic acid (0.15 mL, 2.05 mmol). The reaction mixture was stirred for 1.5 hours. Thereafter, the reaction mixture was concentrated under reduced pressure and the resulting residue was purified by silica gel chromatography with elution system B to obtain the title compound [(1S,2S,3S,4R,5S)-2,3,4-tribenzyloxy-5-[4-chloro-3-[[4-(trifluoromethoxy)phenyl]methyl]phenyl]-6,8-dioxabicyclo[3.2.1]octan-1-yl]methanol 6r (290 mg, white solid), yield: 76.1%. 1H NMR (400 MHz, DMSO-d6): δ 7.59 (dd, 1H), 7.50-7.44 (m, 2H), 7.34-7.15 (m, 17H), 6.83 (d, 2H), 5.22 (t, 1H), 4.81-4.74 (m, 4H), 4.32 (d, 1H), 4.11-4.08 (m, 3H), 4.07-4.04 (m, 1H), 3.93 (d, 1H), 3.87 (t, 1H), 3.79-3.71 (m, 3H), 3.59 (dd, 1H), 3.52 (d, 1H).

Step 15

(1S,2S,3S,4R,5S)-5-[4-chloro-3-[[4-(trifluoromethoxy)phenyl]methyl]phenyl]-1-(hydroxymethyl)-6,8-dioxabicyclo[3.2.1]octane-2,3,4-triol

[(1S,2S,3S,4R,5S)-2,3,4-tribenzyloxy-5-[4-chloro-3-[[4-(trifluoromethoxy)phenyl]methyl]phenyl]-6,8-dioxabicyclo[3.2.1]octan-1-yl]methanol 6r (150 mg, 0.20 mmol) was dissolved in 10 mL of mixed solution (THF and MeOH, v:v=1:1), followed by addition of o-dichlorobenzene (0.23 mL, 2 mmol) and Palladium/carbon (60 mg, 10%). The mixture was exchanged with H2 three times and stirred for 1 hour. Thereafter, the reaction mixture was filtered. The filtrate was concentrated under reduced pressure and the resulting residue was purified by silica gel chromatography with elution system E to obtain the title compound (1S,2S,3S,4R,5S)-5-[4-chloro-3-[[4-(trifluoromethoxy)phenyl]methyl]phenyl]-1-(hydroxymethyl)-6,8-dioxabicyclo-[3.2.1]octane-2,3,4-triol 6 (82 mg, white solid), yield: 86.0%. MS m/z (ESI): 477.1 [M+1]; 1H NMR (400 MHz, CD3OD): δ 7.54 (d, 1H), 7.46-7.39 (m, 2H), 7.30 (d, 2H), 7.17 (d, 2H), 4.17 (d, 3H), 3.86 (d, 1H), 3.80 (d, 1H), 3.72-3.68 (m, 2H), 3.62 (dd, 1H), 3.58 (d, 1H).

Example 7

(1S,2S,3S,4R,5S)-5-[4-chloro-3-[[4-(2,2,2-trifluoroethoxy)phenyl]methyl]phenyl]-1-(hydroxymethyl)-6,8-dioxabicyclo[3.2.1]octane-2,3,4-triol

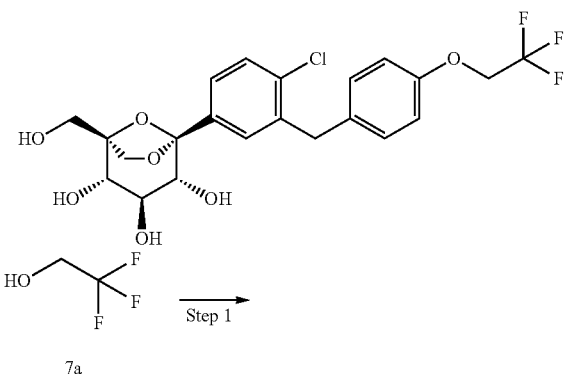

7a

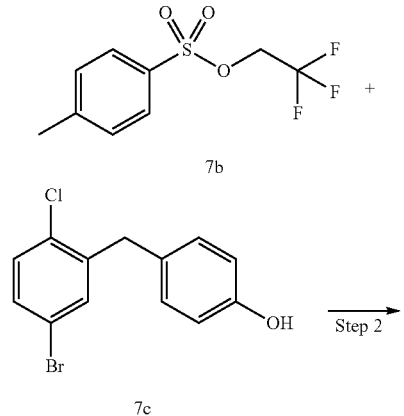

7b

7c

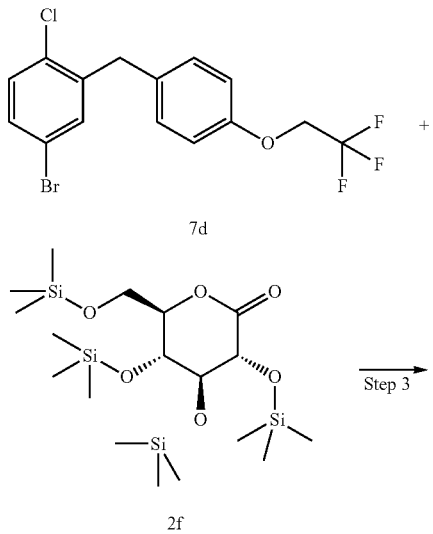

7d

2f

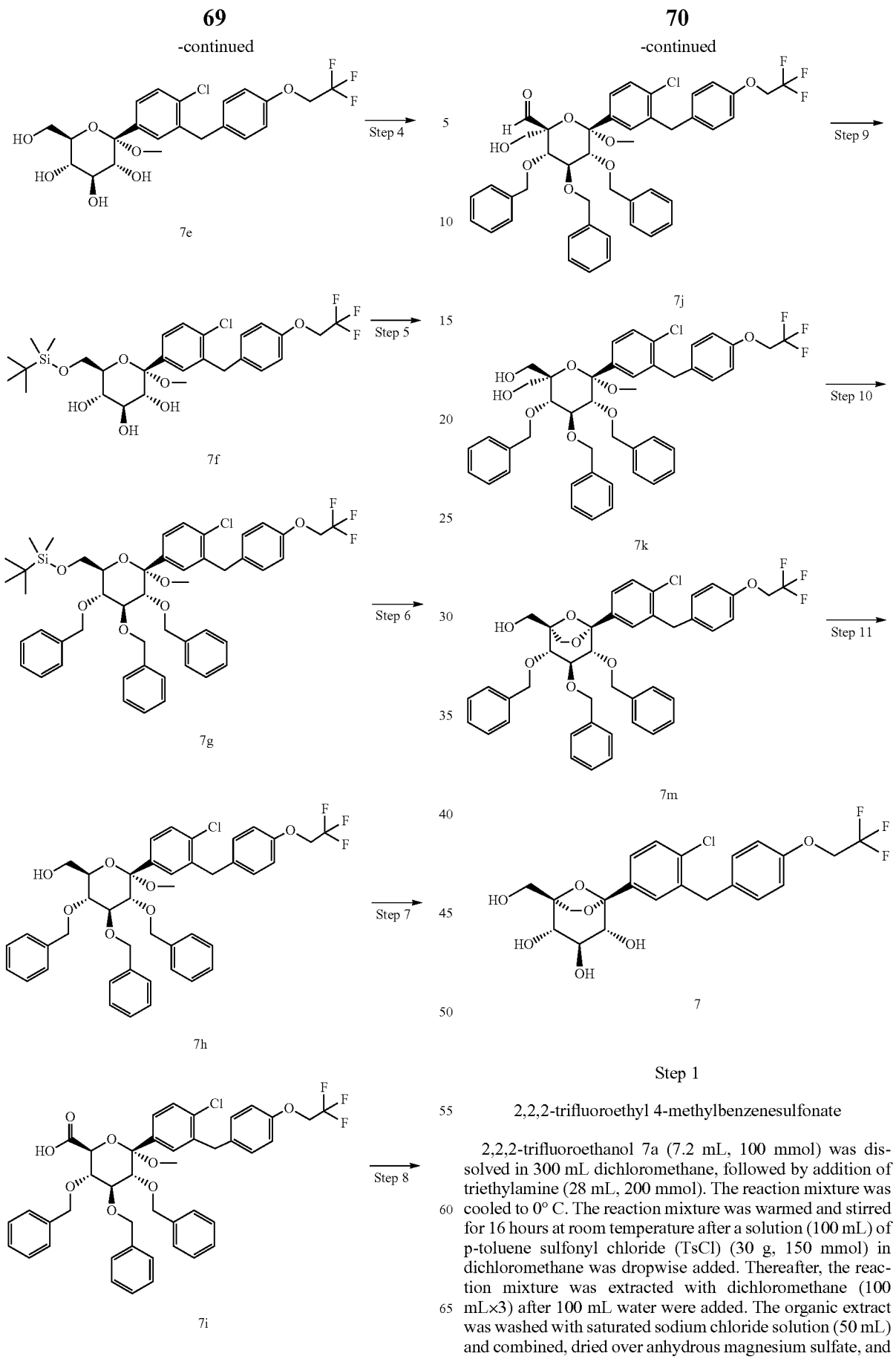

Step 1

2,2,2-trifluoroethyl 4-methylbenzenesulfonate 2,2,2-trifluoroethanol 7a (7.2 mL, 100 mmol) was dissolved in 300 mL dichloromethane, followed by addition of triethylamine (28 mL, 200 mmol). The reaction mixture was cooled to 0° C. The reaction mixture was warmed and stirred for 16 hours at room temperature after a solution (100 mL) of p-toluene sulfonyl chloride (TsCl) (30 g, 150 mmol) in dichloromethane was dropwise added. Thereafter, the reaction mixture was extracted with dichloromethane (100 mL×3) after 100 mL water were added. The organic extract was washed with saturated sodium chloride solution (50 mL) and combined, dried over anhydrous magnesium sulfate, and filtered. The filtrate was concentrated under reduced pressure and the resulting residue was purified by silica gel chromatography with elution system D to obtain the title compound 2,2,2-trifluoroethyl 4-methylbenzenesulfonate 7b (25 g, colourless liquid), yield: 98.4%. 1H NMR (400 MHz, CDCl3): δ 7.88-7.76 (m, 2H), 7.44-7.33 (m, 2H), 4.35 (d, 2H), 2.47 (s, 3H).

Step 2

4-bromo-1-chloro-2-[[4-(2,2,2-trifluoroethoxy)phenyl]methyl]benzene

4-[(5-bromo-2-chloro-phenyl)methyl]phenol 7c (14.5 g, 48.7 mmol, prepared according to the method in WO2009026537) was dissolved in 300 mL DMF, followed by addition of cesium carbonate (31.7 g, 97.5 mmol). The reaction mixture was stirred for 10 minutes. The reaction mixture was stirred for 8 hours at 80° C. after 2,2,2-trifluoroethyl-4-methylbenzenesulfonate 7b (12.4 g, 48.7 mmol) was added. Thereafter, the reaction mixture was filtered and washed with a small amount of ethyl acetate before the filtrate was concentrated under reduced pressure. The resulting residue was partitioned after 100 mL water and 50 mL saturated sodium chloride solution were added. The aqueous phase was extracted with ethyl acetate (100 mL×3) and the organic extract was washed with saturated sodium chloride solution (100 mL), combined and concentrated. The resulting residue was purified by silica gel chromatography with elution system B to obtain the title compound 4-bromo-1-chloro-2-[[4-(2,2,2-trifluoroethoxy)phenyl]methyl]benzene 7d (7.26 g, white solid), yield: 39.2%. 1H NMR (400 MHz, CDCl3): δ 7.32 (s, 1H), 7.30-7.24 (m, 2H), 7.21-7.14 (m, 2H), 6.98-6.87 (m, 2H), 4.38 (d, 2H), 4.06 (s, 2H).

Step 3

(2S,3R,4S,5S,6R)-2-[4-chloro-3-[[4-(2,2,2-trifluoroethoxy)phenyl]methyl]phenyl]-6-(hydroxymethyl)-2-methoxy-tetrahydropyran-3,4,5-triol 4-bromo-1-chloro-2-[[4-(2,2,2-trifluoroethoxy)phenyl]methyl]benzene 7d (6.15 g, 16.2 mmol) was dissolved in 150 mL of mixed solution (THF and n-hexane, v:v=2:3) and cooled to −78° C., followed by dropwise addition of a solution of nBuLi in n-hexane (10 mL, 24.3 mmol). The reaction was stirred for 1 hour at −78° C. before a solution (35 mL) of (3R,4S,5R,6R)-3,4,5-tris(trimethylsilyloxy)-6-(trimethylsilyl-oxymethyl)tetrahydropyran-2-one 2f (8.32 g, 17.8 mmol) in n-hexane was dropwise added. Then, the reaction mixture was stirred for 2 hours at −78° C. before 50 mL methanol and 3.2 mL methylsulfonic acid were added. The reaction mixture was warmed and stirred for 16 hours at room temperature. Thereafter, the reaction mixture was concentrated under reduced pressure and was partitioned after 30 mL saturated sodium bicarbonate solution and 10 mL water were added. The aqueous phase was extracted with ethyl acetate (100 mL×3) and the organic extract was washed with saturated sodium chloride solution (20 mL) and combined, dried over anhydrous magnesium sulfate, and filtered. The filtrate was concentrated under reduced pressure and the resulting residue was purified by silica gel chromatography with elution system D to obtain the title compound (2S,3R,4S,5S,6R)-2-[4-chloro-3-[[4-(2,2,2-trifluoroethoxy)phenyl]methyl]phenyl]-6-(hydroxymethyl)-2-methoxy-tetrahydropyran-3,4,5-triol 7e (3.93 g, white solid), yield: 49.2%. 1H NMR (400 MHz, CD3OD): δ 7.57 (d, 1H), 7.49 (dd, 1H), 7.38 (d, 1H), 7.18 (d, 2H), 6.99-6.88 (m, 2H), 4.49 (q, 2H), 4.19-4.01 (m, 3H), 3.99-3.91 (m, 1H), 3.89-3.71 (m, 2H), 3.66-3.55 (m, 1H), 3.49-3.39 (m, 1H), 3.14-3.04 (s, 3H).

Step 4

(2S,3R,4S,5S,6R)-6-[(tert-butyl(dimethyl)silyl) oxymethyl]-2-[4-chloro-3-[[4-(2,2,2-trifluoroethoxy) phenyl]methyl]phenyl]-2-methoxy-tetrahydropyran-3,4,5-triol (2S,3R,4S,5S,6R)-2-[4-chloro-3-[[4-(2,2,2-trifluoroethoxy)phenyl]methyl]phenyl]-6-(hydroxymethyl)-2-methoxy-tetrahydropyran-3,4,5-triol 7e (3.8 g, 7.71 mmol) was dissolved in 100 mL DMF, followed by addition of DMAP (188 mg, 1.54 mmol), TBSCl (1.39 g, 9.25 mmol) and pyridine (50 mL) in turn, and the reaction mixture was stirred for 36 hours. Thereafter, the reaction mixture was concentrated under reduced pressure and partitioned after 150 mL water were added. The aqueous phase was extracted with ethyl acetate (100 mL×3) and the organic extract was washed with saturated sodium chloride solution (30 mL) and combined, dried over anhydrous magnesium sulfate, and filtered. The filtrate was concentrated under reduced pressure and the resulting residue was purified by silica gel chromatography with elution system D to obtain the title compound (2S,3R, 4S,5S,6R)-6-[(tert-butyl(dimethyl)silyl)oxy-methyl]-2-[4-chloro-3-[[4-(2,2,2-trifluoroethoxy)phenyl]methyl]phenyl]-2-methoxy-tetrahydropyran-3,4,5-triol 7f (2.94 g, yellow grease), yield: 62.8%. 1H NMR (400 MHz, DMSO-d6): δ 7.94 (s, 2H), 7.45 (d, 1H), 7.40 (d, 1H), 7.35-7.28 (m, 1H), 7.17-7.05 (m, 2H), 7.01-6.90 (m, 2H), 5.00 (d, 1H), 4.84-4.74 (m, 2H), 4.68 (q, 2H), 4.11-3.87 (m, 3H), 3.73 (dd, 1H), 3.60-3.46 (m, 1H), 3.42 (ddd, 1H), 3.14 (td, 1H), 2.92 (s, 3H), 0.05-0.02 (m, 3H).

Step 5

[[(2R,3R,4S,5R,6S)-3,4,5-tribenzyloxy-6-[4-chloro-3-[[4-(2,2,2-trifluoroethoxy)phenyl]methyl]phenyl]-6-methoxy-tetrahydropyran-2-yl]methoxy]tert-butyl-dimethyl-silane (2S,3R,4S,5S,6R)-6-[(tert-butyl(dimethyl)silyl)oxymethyl]-2-[4-chloro-3-[[4-(2,2,2-trifluoroethoxy)phenyl]methyl]phenyl]-2-methoxy-tetrahydropyran-3,4,5-triol 7f (2.90 g, 4.78 mmol) was dissolved in 70 mL DMF and cooled to 0° C., followed by addition of 60% NaH (955 mg, 23.9 mmol). The reaction mixture was warmed and stirred for 1 hour at room temperature before benzyl bromide (3.0 mL, 23.9 mmol) was added. After stirring for 3 hours, 5 mL methanol and 10 mL water were added. The reaction mixture was partitioned after 100 mL water and 30 mL saturated sodium chloride solution were added. The aqueous phase was extracted with ethyl acetate (50 mL×3) and the organic extract was washed with saturated sodium chloride solution (30 mL) and combined, dried over anhydrous magnesium sulfate, and filtered. The filtrate was concentrated under reduced pressure to obtain the title compound [[(2R,3R,4S,5R,6S)-3,4,5-tribenzyloxy-6-[4-chloro-3-[[4-(2,2,2-trifluoroethoxy)phenyl]methyl]phenyl]-6-methoxy-tetrahydropyran-2-yl]methoxy]tert-butyl-dimethyl-silane 7g (4.60 g, pale yellow liquid), which was used directly in the next step without purification.

Step 6

[(2R,3R,4S,5R,6S)-3,4,5-tribenzyloxy-6-[4-chloro-3-[[4-(2,2,2-trifluoroethoxy)phenyl]methyl]phenyl]-6-methoxy-tetrahydropyran-2-yl]methanol

[[(2R,3R,4S,5R,6S)-3,4,5-tribenzyloxy-6-[4-chloro-3-[[4-(2,2,2-trifluoroethoxy)phenyl]methyl]phenyl]-6-methoxy-tetrahydropyran-2-yl]methoxy]tert-butyl-dimethyl-silane 7g (4.19 g, 4.78 mmol) was dissolved in 30 mL methanol, followed by addition of acetyl chloride (51 μL, 0.72 mmol). The reaction mixture was stirred for 1 hour. Thereafter, the reaction mixture was concentrated under reduced pressure and the resulting residue was purified by silica gel chromatography with elution system D to obtain the title compound [(2R,3R,4S,5R,6S)-3,4,5-tribenzyloxy-6-[4-chloro-3-[[4-(2,2,2-trifluoroethoxy)phenyl]methyl]phenyl]-6-methoxy-tetrahydropyran-2-yl]methanol 7h (1.1 g, white grease), yield: 30.1%. 1H NMR (400 MHz, DMSO-d6): δ 7.55-7.43 (m, 2H), 7.39-7.28 (m, 6H), 7.28-7.16 (m, 9H), 7.11-7.03 (m, 1H), 7.01 (dd, 2H), 6.90 (d, 2H), 4.91-4.73 (m, 4H), 4.73-4.58 (m, 3H), 4.42 (d, 1H), 4.17-3.87 (m, 4H), 3.83-3.62 (m, 4H), 3.53 (dd, 1H), 3.24 (d, 1H), 3.08-2.86 (m, 3H).

Step 7

(2S,3S,4S,5R,6S)-3,4,5-tribenzyloxy-6-[4-chloro-3-[[4-(2,2,2-trifluoroethoxy)phenyl]methyl]phenyl]-6-methoxy-tetrahydropyran-2-carbaldehyde Oxalyl chloride (0.16 mL, 1.87 mmol) was dissolved in 5 mL dichloromethane and cooled to −78° C., followed by dropwise addition of dimethyl sulfoxide (0.2 mL, 2.88 mmol) in dichloromethane (3 mL). The reaction mixture was stirred for 15 minutes, before 10 mL solution of [(2R,3R,4S,5R,6S)-3,4,5-tribenzyloxy-6-[4-chloro-3-[[4-(2,2,2-trifluoroethoxy)phenyl]methyl]phenyl]-6-methoxy-tetrahydropyran-2-yl]methanol 7h (1.10 g, 1.44 mmol) in dichloromethane were added and stirred for 40 minutes. Then the reaction mixture was warmed and stirred for 3 hours at room temperature after triethylamine (1.0 mL, 7.21 mmol) was dropwise added. Thereafter, the reaction mixture was partitioned after 5 mL 1 M hydrochloric acid were added, the aqueous phase was extracted with ethyl acetate (10 mL×2) and the organic extracts were combined, dried over anhydrous magnesium sulfate, and filtered. The filtrate was concentrated under reduced pressure to obtain the title compound (2S,3S,4S,5R,6S)-3,4,5-tribenzyloxy-6-[4-chloro-3-[[4-(2,2,2-trifluoroethoxy)phenyl]methyl]phenyl]-6-methoxy-tetrahydropyran-2-carbaldehyde 7i (1.06 g, yellow grease), which was used directly in the next step without purification.

Step 8

(2S,3S,4S,5R,6S)-3,4,5-tribenzyloxy-6-[4-chloro-3-[[4-(2,2,2-trifluoroethoxy)phenyl]methyl]phenyl]-2-(hydroxymethyl)-6-methoxy-tetrahydropyran-2-carbaldehyde (2S,3S,4S,5R,6S)-3,4,5-tribenzyloxy-6-[4-chloro-3-[[4-(2,2,2-trifluoroethoxy)phenyl]methyl]phenyl]-6-methoxy-tetrahydropyran-2-carbaldehyde 7l (1.06 g, 1.39 mmol) was dissolved in 20 mL 1,4-dioxane, followed by addition of 2.3 mL 37% formaldehyde solution and 4 mL 2.9 M sodium hydroxide. The reaction mixture was stirred for 25 hours at 70° C. Thereafter, the reaction mixture was concentrated under reduced pressure before 20 mL water and 10 mL saturated sodium chloride solution were added. The reaction mixture was extracted with ethyl acetate (30 mL×3). The organic extract was combined, dried over anhydrous magnesium sulfate, and filtered. The filtrate was concentrated under reduced pressure to obtain the title compound (2S,3S,4S,5R,6S)-3,4,5-tribenzyloxy-6-[4-chloro-3-[[4-(2,2,2-trifluoroethoxy)phenyl]-methyl]phenyl]-2-(hydroxymethyl)-6-methoxy-tetrahydropyran-2-carbaldehyde 7j (1.1 g, yellow grease), which was used directly in the next step without purification.

Step 9

[(3S,4S,5R,6S)-3,4,5-tribenzyloxy-6-[4-chloro-3-[[4-(2,2,2-trifluoroethoxy)phenyl]methyl]phenyl]-2-(hydroxymethyl)-6-methoxy-tetrahydropyran-2-yl]methanol (2S,3S,4S,5R,6S)-3,4,5-tribenzyloxy-6-[4-chloro-3-[[4-(2,2,2-trifluoroethoxy)phenyl]methyl]phenyl]-2-(hydroxymethyl)-6-methoxy-tetrahydropyran-2-carbaldehyde 7j (1.1 g, 1.39 mmol) was dissolved in 30 mL of mixed solution (THF and MeOH, v:v=1:2), followed by addition of sodium borohydride (106 mg, 2.78 mmol) in batch. The reaction mixture was stirred for 30 minutes before 20 mL of water, then 30 mL of water were added. The reaction mixture was extracted with ethyl acetate (50 mL×3). The organic extract was washed with saturated sodium chloride solution (30 mL) and combined, dried over anhydrous magnesium sulfate, and filtered. The filtrate was concentrated under reduced pressure and the resulting residue was purified by silica gel chromatography with elution system D to obtain the title compound [(3S,4S,5R,6S)-3,4,5-tribenzyloxy-6-[4-chloro-3-[[4-(2,2,2-trifluoroethoxy)phenyl]methyl]phenyl]-2-(hydroxymethyl)-6-methoxy-tetrahydropyran-2-yl]methanol 7k (100 mg, yellow grease), yield: 9.1%.

Step 10

[(1S,2S,3S,4R,5S)-2,3,4-tribenzyloxy-5-[4-chloro-3-[[4-(2,2,2-trifluoroethoxy)phenyl]methyl]phenyl]-6,8-dioxabicyclo[3.2.1]octan-1-yl]methanol

[(3S,4S,5R,6S)-3,4,5-tribenzyloxy-6-[4-chloro-3-[[4-(2,2,2-trifluoroethoxy)phenyl]methyl]phenyl]-2-(hydroxymethyl)-6-methoxy-tetrahydropyran-2-yl]methanol 7k (100 mg, 0.13 mmol) was dissolved in 10 mL dichloromethane, followed by addition of 0.1 mL trifluoroacetic acid. The reaction mixture was stirred for 1 hour. Thereafter, the reaction mixture was concentrated under reduced pressure and the resulting residue was purified by silica gel chromatography with elution system D to obtain the title compound [(1S,2S,3S,4R,5S)-2,3,4-tribenzyloxy-5-[4-chloro-3-[[4-(2,2,2-trifluoroethoxy)phenyl]methyl]phenyl]-6,8-dioxabicyclo[3.2.1]octan-1-yl]methanol 7m (22 mg, white solid), yield: 22.9%. MS m/z (ESI): 778.3 [M+18].

Step 11

(1S,2S,3S,4R,5S)-5-[4-chloro-3-[[4-(2,2,2-trifluoroethoxy)phenyl]methyl]phenyl]-1-(hydroxymethyl)-6,8-dioxabicyclo[3.2.1]octane-2,3,4-triol

[(1S,2S,3S,4R,5S)-2,3,4-tribenzyloxy-5-[4-chloro-3-[[4-(2,2,2-trifluoroethoxy)phenyl]methyl]phenyl]-6,8-dioxabicyclo[3.2.1]octan-1-yl]methanol 7m (20 mg, 0.03 mmol) was dissolved in 10 mL of mixed solution (THF and MeOH, v:v=1:1), followed by addition of o-dichlorobenzene (31 μL, 0.27 mmol) and Palladium/carbon (20 mg, 10%) in turn. The mixture was exchanged with H2 three times and was stirred for 2 hours. Thereafter, the reaction mixture was filtered. The filtrate was concentrated under reduced pressure and the resulting residue was purified by thin layer chromatography with developing solvent system A to obtain the title compound (1S,2S,3S,4R,5S)-5-[4-chloro-3-[[4-(2,2,2-trifluoroethoxy)phenyl]methyl]phenyl]-1-(hydroxymethyl)-6,8-dioxabicyclo[3.2.1]octane-2,3,4-triol 7 (9 mg, white solid), yield: 69.2%. MS m/z (ESI): 491.1 [M+1]; 1H NMR (400 MHz, CD3OD): δ 7.48 (m, 1H), 7.40-7.38 (m, 2H), 7.18-7.16 (d, 2H), 6.93-6.91 (d, 2H), 4.51-4.45 (q, 2H), 4.17-4.15 (d, 1H), 4.08 (s, 2H), 3.81-3.78 (d, 1H), 3.78-3.71 (d, 1H), 3.69-3.67 (m, 2H), 3.62-3.57 (m, 2H).
Example 8
(1S,2S,3S,4R,5S)-5-[4-chloro-3-[[3-fluoro-4-(trideuteriomethoxy)phenyl]methyl]phenyl]-1-(hydroxymethyl)-6,8-dioxabicyclo[3.2.1]octane-2,3,4-triol
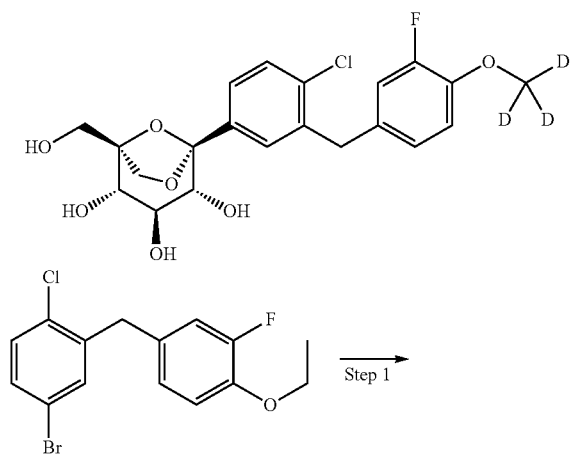
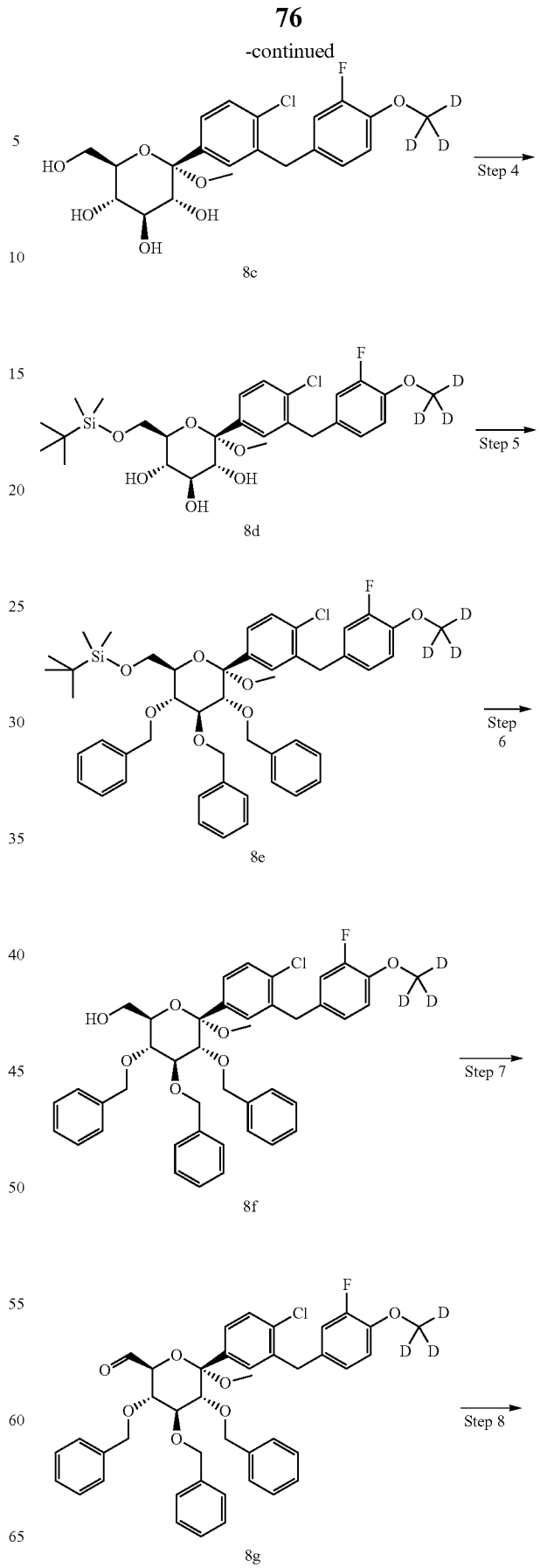

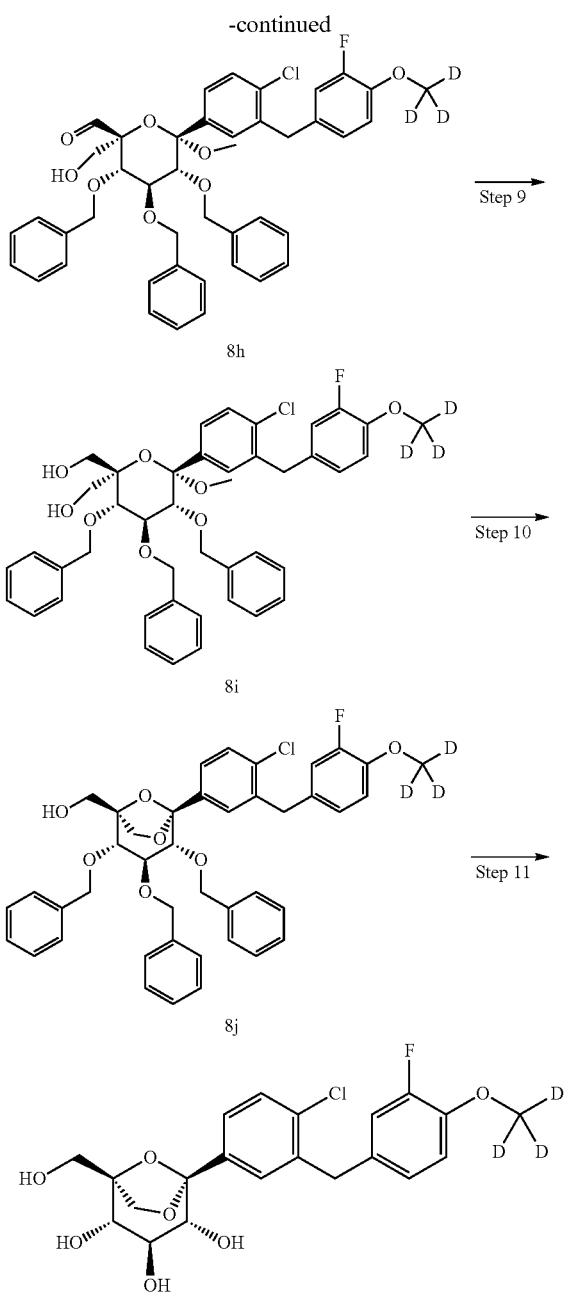

anhydrous magnesium sulfate, and filtered. The filtrate was concentrated under reduced pressure. The resulting residue was purified by silica gel chromatography with elution system D to obtain the title compound 4-[(5-bromo-2-chloro-phenyl)methyl]-2-fluorophenol 8a (28.1 g, white solid), yield: 96.7%. 1H NMR (400 MHz, CDCl$_3$): δ 7.36-7.18 (m, 3H), 7.01-6.80 (m, 3H), 5.08 (br, 1H), 3.99 (s, 2H).

Step 2

4-[(5-bromo-2-chloro-phenyl)methyl]-2-fluoro-1-(trideuteriomethoxy)benzene

4-[(5-bromo-2-chloro-phenyl)methyl]-2-fluoro-phenol 8a (10.0 g, 31.75 mmol) was dissolved in 150 mL THF, followed by addition of triphenylphosphine (16.6 g, 63.5 mmol) and azodicarboxylic acid diisopropyl ester (12.6 mL, 63.5 mmol). The reaction mixture was stirred for 30 minutes. The reaction mixture was stirred for 18 hours after 3 mL CD3OD were added. Thereafter, the reaction mixture was concentrated under reduced pressure and the resulting residue was recrystallized with petroleum ether, filtered, and collected as a product. The product was re-dissolved in 50 mL methanol before 2 mL hydrogen peroxide were added. Followed by stirring for 1 minute, the reaction mixture were partitioned after 5 g sodium thiosulfate, 40 mL water and 50 mL ethyl acetate were added. The aqueous phase was extracted with ethyl acetate (30 mL×3) and the organic extract was washed with saturated sodium chloride solution (30 mL), combined, dried over anhydrous magnesium sulfate, and filtered. The filtrate was concentrated under reduced pressure and the residue was purified by silica gel chromatography with elution system D to obtain the title compound 4-[(5-bromo-2-chloro-phenyl) methyl]-2-fluoro-1-(trideuteriomethoxy)benzene 8b (8.2 g, white solid), yield: 77.4%. 1H NMR (400 MHz, CDCl3): δ 7.37-7.32 (m, 1 H), 7.32-7.28 (m, 2 H), 6.99-6.89 (m, 3 H), 4.02 (s, 2 H).

Step 3

(2S,3R,4S,5S,6R)-2-[4-chloro-3-[[3-fluoro-4-(trideuteriomethoxy)phenyl]methyl]phenyl]-6-(hydroxymethyl)-2-methoxy-tetrahydropyran-3,4,5-triol 4-[(5-bromo-2-chloro-phenyl)methyl]-2-fluoro-1-(trideuteriomethoxy)benzene 8b (8.2 g, 24.6 mmol) was dissolved in 150 mL of mixed solution (THF and n-hexane, v:v=2:3) and cooled to −78° C., followed by dropwise addition of a solution of nBuLi (14.8 mL, 36.9 mmol) in n-hexane. After stirring for 2 hours at −78° C., a solution (40 mL) of (3R,4S,5R,6R)-3,4,5-tris(trimethylsilyloxy)-6-(trimethylsilyloxymethyl)tetra-hydropyran-2-one 2f (12.6 g, 27.1 mmol) in n-hexane was dropwise added. Then, the reaction mixture was stirred for 3 hours at −78° C. 40 mL methanol and 4.79 mL methanesulfonic acid were added before the reaction mixture was warmed and stirred for 16 hours at room temperature. Thereafter, the reaction mixture was concentrated under reduced pressure and was partitioned after 40 mL saturated sodium bicarbonate solution, 100 mL ethyl acetate and 100 mL water were added. The aqueous phase was extracted with ethyl acetate (50 mL×4) and the organic extracts were combined, dried over anhydrous magnesium sulfate, and filtered. The filtrate was concentrated under reduced pressure and the resulting residue was purified by silica gel chromatography with elution system D to obtain the title compound (2S,3R,4S,5S,6R)-2-[4-chloro-3-[[3-fluoro-4-(trideuteriomethoxy)phenyl]methyl]phenyl]-6-(hy- Step 1

4-[(5-bromo-2-chloro-phenyl)methyl]-2-fluoro-phenol

4-[(5-bromo-2-chloro-phenyl)methyl]-1-ethoxy-2-fluorobenzene 4e (31.7 g, 92.3 mmol) was dissolved in 300 mL dichloromethane, followed by addition of boron tribromide (11.4 mL, 120 mmol) in an ice bath, then the reaction mixture was warmed and stirred for 4 hours. Thereafter, the reaction mixture was extracted with ethyl acetate (100 mL×4) after 300 mL saturated sodium carbonate solution was dropwise added slowly. The organic extract was washed with saturated sodium chloride solution (30 mL) and combined, dried over droxymethyl)-2-methoxytetrahydropyran-3,4,5-triol 8c (8.2 g, white solid), yield: 83.6%. 1H NMR (400 MHz, CDCl3): δ 7.47-7.29 (m, 3 H), 6.93-6.78 (m, 3 H), 4.08-3.98 (m, 2 H), 3.98-3.78 (m, 5 H), 3.73 (d, 1 H), 3.47 (s, 6 H).

Step 4

(2S,3R,4S,5S,6R)-6-[(tert-butyl(dimethyl)silyl)
oxymethyl]-2-[4-chloro-3-[[3-fluoro-4-(trideuteriomethoxy)phenyl]methyl]phenyl]-2-methoxy-tetrahydropyran-3,4,5-triol (2S,3R,4S,5S,6R)-2-[4-chloro-3-[[3-fluoro-4-(trideuteriomethoxy)phenyl]methyl]phenyl]-6-(hydroxymethyl)-2-methoxy-tetrahydropyran-3,4,5-triol 8c (9.2 g, 20.6 mmol) was dissolved in 80 mL pyridine, followed by addition of 4-dimethylamino pyridine (502 mg, 4.11 mmol) and tert-butyl-dimethyl-chloro-silane (3.72 g, 24.7 mmol). The reaction mixture was stirred for 24 hours and concentrated under reduced pressure, and was partitioned after 80 mL ethyl acetate and 80 mL water were added. The aqueous phase was extracted with ethyl acetate (30 mL×3) and the organic extract was combined, dried over anhydrous magnesium sulfate, and filtered. The filtrate was concentrated under reduced pressure and the resulting residue was purified by silica gel chromatography with elution system D to obtain the title compound (2S,3R,4S,5S,6R)-6-[(tert-butyl(dimethyl)silyl)oxymethyl]-2-[4-chloro-3-[[3-fluoro-4-(trideuteriomethoxy)phenyl]methyl]phenyl]-2-methoxy-tetrahydropyran-3,4,5-triol 8d (2.4 g, yellow grease), yield: 20.9%.

Step 5

[[(2R,3R,4S,5R,6S)-3,4,5-tribenzyloxy-6-[4-chloro-3-[[3-fluoro-4-(trideuteriomethoxy)phenyl]methyl]
phenyl]-6-methoxy-tetrahydropyran-2-yl]methoxy]
tert-butyl-dimethyl-silane (2S,3R,4S,5S,6R)-6-[(tert-butyl(dimethyl)silyl)oxymethyl]-2-[4-chloro-3-[[3-fluoro-4-(trideuteriomethoxy)phenyl]methyl]phenyl]-2-methoxy-tetrahydropyran-3,4,5-triol 8d (2.4 g, 4.29 mmol) was dissolved in 70 mL DMF and cooled to 0° C., followed by addition of 60% NaH (857 mg, 21.4 mmol). Then the reaction mixture was warmed to room temperature and stirred for 1 hour. Thereafter, benzyl bromide (2.56 mL, 21.4 mmol) was added before the mixture was stirred for 3 hours. 5 mL methanol and 100 mL water were added before the reaction mixture was extracted with ethyl acetate (50 mL×3). The organic extract was washed with saturated sodium chloride solution (30 mL) and combined, dried over anhydrous magnesium sulfate, and filtered. The filtrate was concentrated under reduced pressure to obtain the title compound [[(2R,3R,4S,5R,6S)-3,4,5-tribenzyloxy-6-[4-chloro-3-[[3-fluoro-4-(trideuteriomethoxy)phenyl]methyl]phenyl]-6-methoxy-tetrahydropyran-2-yl]methoxy] tert-butyl-dimethyl-1-silane 8e (3.56 g, yellow solid), which was used directly in the next step without purification.

Step 6

[(2R,3R,4S,5R,6S)-3,4,5-tribenzyloxy-6-[4-chloro-3-[[3-fluoro-4-(trideuteriomethoxy)phenyl]methyl]
phenyl]-6-methoxy-tetrahydropyran-2-yl]methanol

[[(2R,3R,4S,5R,6S)-3,4,5-tribenzyloxy-6-[4-chloro-3-[[3-fluoro-4-(trideuteriomethoxy)phenyl]methyl]phenyl]-6-methoxy-tetrahydropyran-2-yl]methoxy]tert-butyl-dimethyl-silane 8e (3.56, 4.29 mmol) was dissolved in 30 mL methanol and stirred for 4 hours after addition of acetyl chloride (95.5 μL, 1.34 mmol). Thereafter, the reaction mixture was concentrated under reduced pressure. The reaction mixture was extracted with ethyl acetate (30 mL×3) after 30 mL water were added. The organic extract was combined, dried over anhydrous magnesium sulfate, and filtered. The filtrate was concentrated under reduced pressure and the resulting residue was purified by silica gel chromatography with elution system D to obtain the title compound [(2R,3R,4S,5R,6S)-3,4,5-tribenzyloxy-6-[4-chloro-3-[[3-fluoro-4-(trideuteriomethoxy)phenyl]methyl]phenyl]-6-methoxy-tetrahydropyran-2-yl]methanol 8f (2.2 g, yellow solid), yield: 73.3%. 1H NMR (400 MHz, CDCl3): δ 7.42-7.27 (m, 13 H), 7.24-7.14 (m, 3 H), 6.98 (d, 2 H), 6.89-6.72 (m, 3 H), 4.96-4.87 (m, 3 H), 4.71-4.67 (m, 1 H), 4.51 (d, 1 H), 4.18 (t, 1 H), 4.07 (d, 1 H), 3.95-3.84 (m, 3 H), 3.83-3.77 (m, 1 H), 3.76-3.64 (m, 2 H), 3.30 (d, 1 H), 3.07 (s, 3 H).

Step 7

(2S,3S,4S,5R,6S)-3,4,5-tribenzyloxy-6-[4-chloro-3-[[3-fluoro-4-(trideuteriomethoxy)phenyl]methyl]
phenyl]-6-methoxy-tetrahydropyran-2-carbaldehyde Oxalyl chloride (0.34 mL, 3.93 mmol) was dissolved in 5 mL dichloromethane and cooled to −78° C. A solution (10 mL) of dimethyl sulfoxide (0.43 mL, 6.04 mmol) in dichloromethane was added before the mixture was stirred for 15 minutes. Then 15 mL solution of [(2R,3R,4S,5R,6S)-3,4,5-tribenzyloxy-6-[4-chloro-3-[[3-fluoro-4-(trideuteriomethoxy)phenyl]methyl]phenyl]-6-methoxy-tetrahydropyran-2-yl]methanol 8f (2.2 g, 3.02 mmol) in methylene chloride were added before the mixture was stirred for 45 minutes. Thereafter, triethylamine (2.1 mL, 15.1 mmol) was added before the mixture was warmed to room temperature and stirred for 2.5 hours. 5 mL 1 M hydrochloric acid solution were added before the mixture was extracted with dichloromethane (15 mL×2). The organic extracts were combined, dried over anhydrous magnesium sulfate, and filtered. The filtrate was concentrated under reduced pressure to obtain the title compound (2S,3S,4S,5R,6S)-3,4,5-tribenzyloxy-6-[4-chloro-3-[[3-fluoro-4-(trideuteriomethoxy)phenyl]methyl]phenyl]-6-methoxy-tetrahydropyran-2-carbaldehyde 8g (2.1 g, yellow liquid), which was used directly in the next step without purification.

Step 8

(2S,3S,4S,5R,6S)-3,4,5-tribenzyloxy-6-[4-chloro-3-[[3-fluoro-4-(trideuteriomethoxy)phenyl]methyl]
phenyl]-2-(hydroxymethyl)-6-methoxy-tetrahydropyran-2-carbaldehyde (2S,3S,4S,5R,6S)-3,4,5-tribenzyloxy-6-[4-chloro-3-[[3-fluoro-4-(trideuteriomethoxy)-phenyl]methyl]phenyl]-6-methoxy-tetrahydropyran-2-carbaldehyde 8g (2.1 g, 2.94 mmol) was dissolved in 50 mL 1,4-dioxane, followed by addition of formaldehyde solution (5.4 mL, 72.2 mmol) and 3.94 mL 3 M sodium hydroxide. The reaction mixture was stirred for 6 hours at 50° C. Thereafter, the reaction mixture was extracted with ethyl acetate (20 mL×3) after 20 mL of water were added. The organic extracts were combined, dried over anhydrous magnesium sulfate, and filtered. The filtrate was concentrated under reduced pressure to obtain the title compound (2S,3S,4S,5R,6S)-3,4,5-tribenzyloxy-6-[4-chloro-3-[[3-fluoro-4-(trideuteriomethoxy)phenyl]methyl]

phenyl]-2-(hydroxymethyl)-6-methoxy-tetrahydropyran-2-carbaldehyde 8h (2.5 g, yellow liquid), which was used directly in the next step without purification.

Step 9

[(3S,4S,5R,6S)-3,4,5-tribenzyloxy-6-[4-chloro-3-[[3-fluoro-4-(trideuteriomethoxy)phenyl]methyl]phenyl]-2-(hydroxymethyl)-6-methoxy-tetrahydropyran-2-yl]methanol (2S,3S,4S,5R,6S)-3,4,5-tribenzyloxy-6-[4-chloro-3-[[3-fluoro-4-(trideuteriomethoxy)phenyl]methyl]phenyl]-2-(hydroxymethyl)-6-methoxy-tetrahydropyran-2-carbaldehyde 8h (2.5 g, 3.36 mmol) was dissolved in 30 mL of mixed solution (THF and MeOH, v:v=1:2), followed by addition of sodium borohydride (269 mg, 6.72 mmol) in batch. The reaction mixture was stirred for 2 hours, then quenched with 40 mL water. The reaction mixture was extracted with ethyl acetate (40 mL×3). The organic extract was washed with saturated sodium chloride solution (30 mL) and combined, dried over anhydrous magnesium sulfate and filtered. The filtrate was concentrated under reduced pressure to obtain the title compound [(3S,4S,5R,6S)-3,4,5-tribenzyloxy-6-[4-chloro-3-[[3-fluoro-4-(trideuteriomethoxy)phenyl]methyl]phenyl]-2-(hydroxymethyl)-6-methoxy-tetrahydropyran-2-yl]methanol 81 (350 mg, yellow liquid), yield: 15.9%. 1H NMR (400 MHz, CDCl3): δ 7.41-7.19 (m, 16 H), 7.04 (dd, 2 H), 6.86-6.76 (m, 3 H), 5.01-4.87 (m, 3 H), 4.71-4.59 (m, 2 H), 4.44-4.31 (m, 2 H), 4.06-3.92 (m, 3 H), 3.87-3.76 (m, 3 H), 3.68 (d, 1 H), 3.25 (d, 1 H), 3.07 (s, 3 H).

Step 10

[(1S,2S,3S,4R,5S)-2,3,4-tribenzyloxy-5-[4-chloro-3-[[3-fluoro-4-(trideuteriomethoxy)phenyl]methyl]phenyl]-6,8-dioxabicyclo[3.2.1]octan-1-yl]methanol

[(3S,4S,5R,6S)-3,4,5-tribenzyloxy-6-[4-chloro-3-[[3-fluoro-4-(trideuteriomethoxy)phenyl]methyl]phenyl]-2-(hydroxymethyl)-6-methoxy-tetrahydropyran-2-yl]methanol 8i (350 mg, 0.47 mmol) was dissolved in 20 mL dichloromethane, followed by 0.5 mL addition of trifluoroacetic acid. The reaction mixture was stirred for 2 hours. Thereafter, the reaction mixture was concentrated under reduced pressure and the resulting residue was purified by silica gel chromatography with elution system D to obtain the title compound [(1S,2S,3S,4R,5S)-2,3,4-tribenzyloxy-5-[4-chloro-3-[[3-fluoro-4-(trideuteriomethoxy)phenyl]methyl]phenyl]-6,8-dioxabicyclo[3.2.1]octan-1-yl]methanol 8j (200 mg, colourless liquid), yield: 59.7%. MS m/z (ESI): 731.3 [M+18].

Step 11

(1S,2S,3S,4R,5S)-5-[4-chloro-3-[[3-fluoro-4-(trideuteriomethoxy)phenyl]methyl]phenyl]-1-(hydroxymethyl)-6,8-dioxabicyclo[3.2.1]octane-2,3,4-triol

[(1S,2S,3S,4R,5S)-2,3,4-tribenzyloxy-5-[4-chloro-3-[[3-fluoro-4-(trideuteriomethoxy)phenyl]methyl]phenyl]-6,8-dioxabicyclo[3.2.1]octan-1-yl]methanol 8j (190 mg, 0.27 mmol) was dissolved in 30 mL of mixed solution (THF and MeOH, v:v=1:1), followed by addition of o-dichlorobenzene (391 mg, 2.66 mmol) and Palladium/carbon (20 mg, 10%) in turn. The mixture was exchanged with H2 three times and stirred for 3 hours. Thereafter, the reaction mixture was filtered. The filtrate was concentrated under reduced pressure and the resulting residue was purified by silica gel chromatography with elution system F to obtain the title compound (1S,2S,3S,4R,5S)-5-[4-chloro-3-[[3-fluoro-4-(trideuteriomethoxy)phenyl]methyl]phenyl]-1-(hydroxymethyl)-6,8-dioxabicyclo[3.2.1]octane-2,3,4-triol 8 (74 mg, white solid), yield: 62.7%. MS m/z (ESI): 461.1 [M+18]; 1H NMR (400 MHz, CD3OD): δ 7.59-7.45 (m, 1 H), 7.45-7.33 (m, 2 H), 7.06-6.84 (m, 3 H), 4.16 (d, 1 H), 4.05 (d, 2 H), 3.93-3.76 (m, 2 H), 3.75-3.52 (m, 4 H).

Example 9

(1S,2S,3S,4R,5S)-5-[3-[[5-(4-fluorophenyl)-2-thienyl]methyl]-4-methyl-phenyl]-1-(hydroxymethyl)-6,8-dioxabicyclo[3.2.1]octane-2,3,4-triol

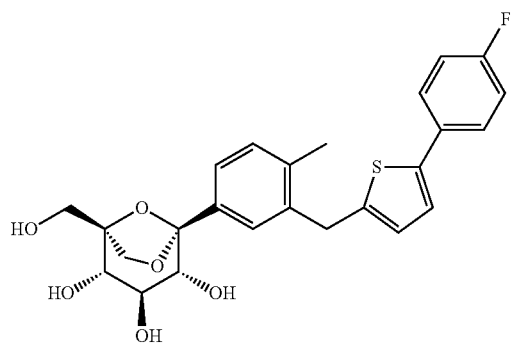

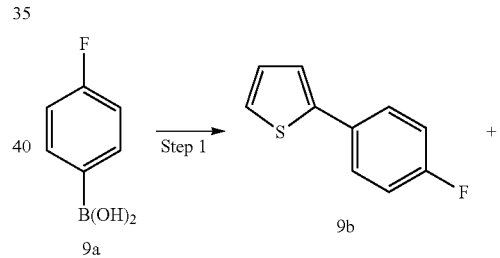

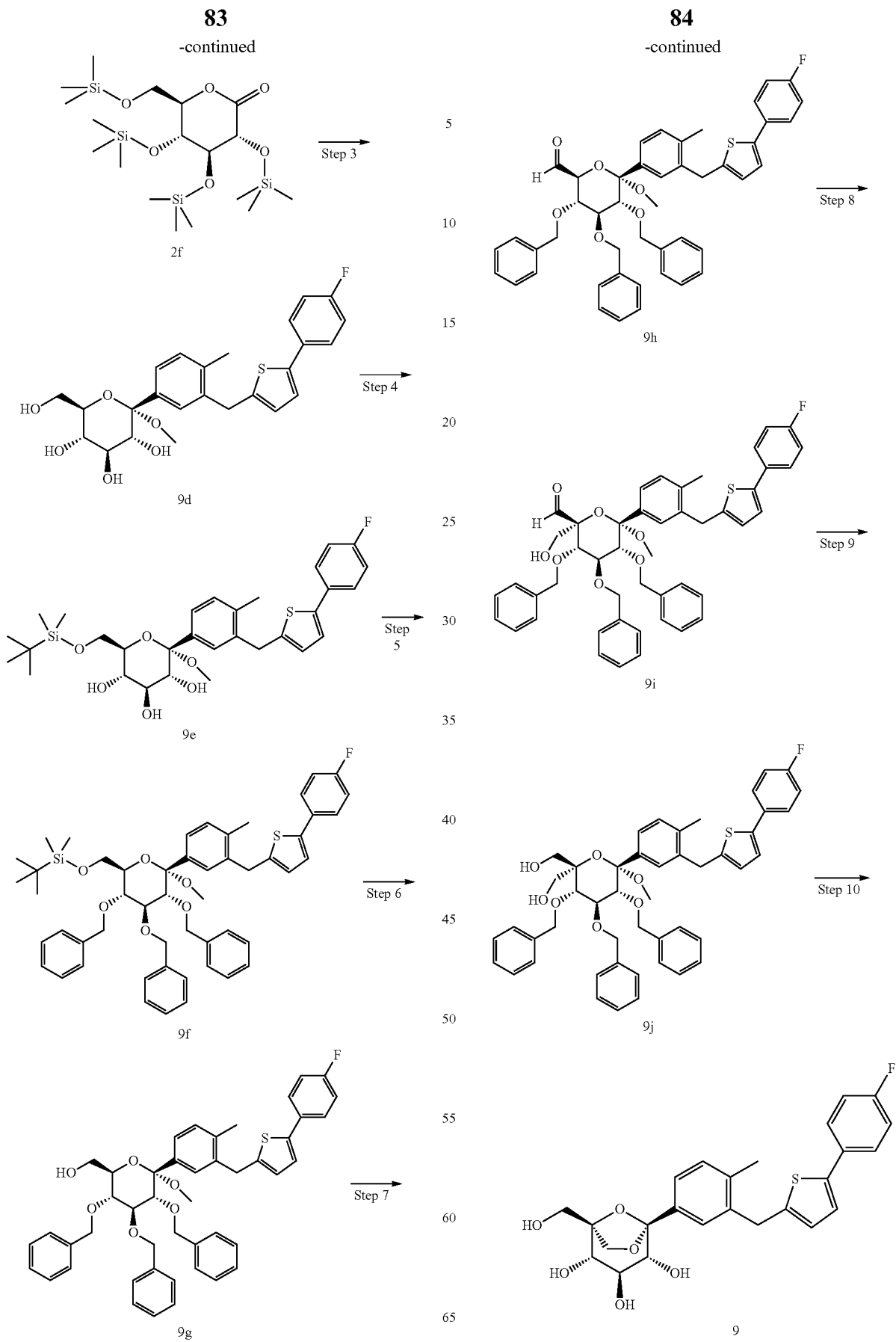

Step 1

2-(4-fluorophenyl)thiophene 2-iodothiophene (1.05 g, 5 mmol) was dissolved in 6 mL of mixed solution (dimethyl ether and water, v:v=2:1), followed by addition of 4-fluorophenylboronic acid 9a (700 mg, 5 mmol), potassium carbonate (1.38 g, 10 mmol) and tetrakis(triphenyl phosphine)palladium (173 mg, 0.15 mmol). The mixture was microwaved for 30 minutes at 100° C. Thereafter, the reaction mixture was extracted with ethyl acetate (20 mL×3) after 10 mL water were added. The organic extract was washed with saturated sodium chloride solution (20 mL) and combined, dried over anhydrous magnesium sulfate, and filtered. The filtrate was concentrated under reduced pressure and the resulting residue was purified by silica gel chromatography with elution system C to obtain the title compound 2-(4-fluorophenyl)thiophene 9b (767 mg, white solid), yield: 86.1%.

Step 2

(5-bromo-2-chloro-phenyl)-[5-(4-fluorophenyl)-2-thienyl]methanone

AlCl3 (1.5 g, 11 mmol) was dissolved in 10 mL methylene chloride and cooled to −10° C., followed by addition of 5-bromo-2-chloro-benzoyl chloride 2a (2.54 g, 10 mmol) and 2-(4-fluorophenyl)thiophene 9b (1.78 g, 10 mmol). The reaction mixture was stirred for 30 minutes and then warmed to room temperature and stirred for another 16 hours. Thereafter, the reaction mixture was cooled to −10° C. The reaction mixture was extracted with ethyl acetate (50 mL×2) after a small amount of water and 20 mL 1 M hydrochloric acid were added. The organic extracts were combined, dried over anhydrous magnesium sulfate, and filtered. The filtrate was concentrated under reduced pressure and the resulting residue was purified by silica gel chromatography with elution system B to obtain the title compound (5-bromo-2-chloro-phenyl)-[5-(4-fluorophenyl)-2-thienyl]methanone 9c (1.5 g, yellow solid), yield: 37.9%.

Step 3

(2S,3R,4S,5S,6R)-2-[3-[[5-(4-fluorophenyl)-2-thienyl]methyl]-4-methyl-phenyl]-6-(hydroxymethyl)-2-methoxy-tetrahydropyran-3,4,5-triol (5-bromo-2-chloro-phenyl)-[5-(4-fluorophenyl)-2-thienyl]methanone 9c (3.7 g, 10.4 mmol) was dissolved in 40 mL THF and cooled to −78° C., followed by dropwise addition of a solution of nBuLi in n-hexane (5 mL, 12.5 mmol). The reaction mixture was stirred for 1 hour at −78° C. 30 mL solution of (3R,4S,5R,6R)-3,4,5-tris(trimethylsilyloxy)-6-(trimethylsilyloxymethyl)tetrahydropyran-2-one 2f (4.85 g, 10.4 mmol) in THF were added before the reaction mixture was stirred for 2 hours at −78° C. A solution (60 mL) of 0.6 M methanesulfonic acid in methanol was added before the reaction mixture was warmed and stirred for 16 hours at room temperature. Thereafter, the reaction mixture was concentrated under reduced pressure and extracted with ethyl acetate (40 mL×3) after 30 mL saturated sodium carbonate solution were added. The organic extracts were combined, dried over anhydrous magnesium sulfate, and filtered. The filtrate was concentrated under reduced pressure and the resulting residue was purified by silica gel chromatography with elution system A to obtain the title compound (2S,3R,4S,5S,6R)-2-[3-[[5-(4-fluorophenyl)-2-thienyl]methyl]-4-methyl-phenyl]-6-(hydroxymethyl)-2-methoxy-tetrahydropyran-3,4,5-triol 9d (1.8 g, orange solid), yield: 36.7%.

Step 4

(2S,3R,4S,5S,6R)-6-[(tert-butyl(dimethyl)silyl)oxymethyl]-2-[3-[[5-(4-fluorophenyl)-2-thienyl]methyl]-4-methyl-phenyl]-2-methoxy-tetrahydropyran-3,4,5-triol (2S,3R,4S,5S,6R)-2-[3-[[5-(4-fluorophenyl)-2-thienyl]methyl]-4-methyl-phenyl]-6-(hydroxymethyl)-2-methoxy-tetrahydropyran-3,4,5-triol 9d (1.8 g, 3.8 mmol) was dissolved in 20 mL pyridine, followed by addition of 4-dimethylamino pyridine (93 mg, 0.76 mmol) and TBSCl (686 mg, 4.55 mmol) in turn. The reaction mixture was stirred for 16 hours. Thereafter, the reaction mixture was concentrated under reduced pressure, dissolved in 30 mL ethyl acetate and was partitioned after 30 mL water were added. The aqueous phase was extracted with ethyl acetate (30 mL×3) and the organic extracts were combined, dried over anhydrous magnesium sulfate, and filtered. The filtrate was concentrated under reduced pressure and the resulting residue was purified by silica gel chromatography with elution system A to obtain the title compound (2S,3R,4S,5S,6R)-6-[(tert-butyl(dimethyl)silyl)oxymethyl]-2-[3-[[5-(4-fluorophenyl)-2-thienyl]methyl]-4-methyl-phenyl]-2-methoxy-tetrahydropyran-3,4,5-triol 9e (2.0 g, orange solid), yield: 89.7%.

Step 5

[[(2R,3R,4S,5R,6S)-3,4,5-tribenzyloxy-6-[3-[[5-(4-fluorophenyl)-2-thienyl]methyl]-4-methyl-phenyl]-6-methoxy-tetrahydropyran-2-yl]methoxy]tert-butyl-dimethyl-silane (2S,3R,4S,5S,6R)-6-[(tert-butyl(dimethyl)silyl)oxymethyl]-2-[3-[[5-(4-fluorophenyl)-2-thienyl]methyl]-4-methyl-phenyl]-2-methoxy-tetrahydropyran-3,4,5-triol 9e (2.0 g, 3.4 mmol) was dissolved in 20 mL DMF and cooled to 0° C., followed by addition of 60% NaH (680 mg, 17 mmol). The reaction mixture was warmed to room temperature and stirred for 30 minutes. Thereafter, benzyl bromide (2.0 mL, 17 mmol) was added before the mixture was stirred for 16 hours. The reaction mixture was concentrated under reduced pressure after 10 mL methanol were added and was partitioned after 30 mL ethyl acetate and 30 mL water were added. The aqueous phase was extracted with ethyl acetate (20 mL×3) and the organic extracts were combined, dried over anhydrous magnesium sulfate, and filtered. The filtrate was concentrated under reduced pressure to obtain the title compound [[(2R,3R,4S,5R,6S)-3,4,5-tribenzyloxy-6-[3-[[5-(4-fluorophenyl)-2-thienyl]methyl]-4-methyl-phenyl]-6-methoxy-tetrahydropyran-2-yl]methoxy]tert-butyl-dimethyl-silane 9f (2.9 g, yellow grease), which was used directly in the next step without purification.

Step 6

[(2R,3R,4S,5R,6S)-3,4,5-tribenzyloxy-6-[3-[[5-(4-fluorophenyl)-2-thienyl]methyl]-4-methyl-phenyl]-6-methoxy-tetrahydropyran-2-yl]methanol

[[(2R,3R,4S,5R,6S)-3,4,5-tribenzyloxy-6-[3-[[5-(4-fluorophenyl)-2-thienyl]methyl]-4-methyl-phenyl]-6-methoxy-tetrahydropyran-2-yl]methoxy]tert-butyl-dimethyl-silane 9f (2.9 g, 3.37 mmol) was dissolved in 20 mL methanol, followed by addition of acetyl chloride (38 μL, 0.5 mmol). The reaction mixture was stirred for 2 hours and was partitioned after 30 mL ethyl acetate and 30 mL water were added. The aqueous phase was extracted with ethyl acetate (30 mL×2) and the organic extracts were combined, dried over anhydrous magnesium sulfate, and filtered. The filtrate was concentrated under reduced pressure and then the resulting residue was purified by silica gel chromatography with elution system B to obtain the title compound [(2R,3R,4S,5R,6S)-3,4,5-tribenzyloxy-6-[3-[[5-(4-fluorophenyl)-2-thienyl]methyl]-4-methyl-phenyl]-6-methoxy-tetrahydropyran-2-yl]methanol 9g (1.9 g, yellow solid), yield: 76.0%.

Step 7

(2S,3S,4S,5R,6S)-3,4,5-tribenzyloxy-6-[3-[[5-(4-fluorophenyl)-2-thienyl]methyl]-4-methyl-phenyl]-6-methoxy-tetrahydropyran-2-carbaldehyde Oxalyl chloride (0.27 mL, 3.12 mmol) was dissolved in 8 mL dichloromethane and cooled to −78° C. The reaction mixture was stirred for 15 minutes before 4 mL solution of dimethyl sulfoxide (0.36 mL, 5.04 mmol) in dichloromethane were added. Then 8 mL solution of [(2R,3R,4S,5R,6S)-3,4,5-tribenzyloxy-6-[3-[[5-(4-fluorophenyl)-2-thienyl]methyl]-4-methyl-phenyl]-6-methoxy-tetrahydropyran-2-yl]methanol 9g (1.8 g, 2.4 mmol) in dichloromethane were dropwise added. The reaction mixture was stirred for 30 minutes. Then triethylamine (1.66 mL, 12 mmol) was added before the reaction mixture was warmed to room temperature and stirred for 1 hour. Thereafter, the reaction mixture was partitioned after 12 mL 1 M hydrochloric acid were added, the organic extract was combined, dried over anhydrous magnesium sulfate, and filtered. The filtrate was concentrated under reduced pressure to obtain the title compound (2S,3S,4S,5R,6S)-3,4,5-tribenzyloxy-6-[3-[[5-(4-fluorophenyl)-2-thienyl]methyl]-4-methyl-phenyl]-6-methoxy-tetrahydropyran-2-carbaldehyde 9h (1.8 g, yellow grease), which was used directly in the next step without purification.

Step 8

(2S,3S,4S,5R,6S)-3,4,5-tribenzyloxy-6-[3-[[5-(4-fluorophenyl)-2-thienyl]methyl]-4-methyl-phenyl]-2-(hydroxymethyl)-6-methoxy-tetrahydropyran-2-carbaldehyde (2S,3S,4S,5R,6S)-3,4,5-tribenzyloxy-6-[3-[[5-(4-fluorophenyl)-2-thienyl]methyl]-4-methyl-phenyl]-6-methoxy-tetrahydropyran-2-carbaldehyde 9h (1.53 g, 2.1 mmol) was dissolved in 15 mL 1,4-dioxane, followed by addition of 3.4 mL 37% formaldehyde solution and 6.3 mL 1 M sodium hydroxide. The reaction mixture was stirred for 16 hour at 70° C., and was partitioned after 50 mL saturated sodium chloride solution were added. The aqueous phase was extracted with ethyl acetate (50 mL×3) and the organic extracts were combined, dried over anhydrous magnesium sulfate, and filtered. The filtrate was concentrated under reduced pressure to obtain the title compound (2S,3S,4S,5R,6S)-3,4,5-tribenzyloxy-6-[3-[[5-(4-fluorophenyl)-2-thienyl]methyl]-4-methyl-phenyl]-2-(hydroxymethyl)-6-methoxy-tetrahydropyran-2-carbaldehyde 9i (2.0 g, pale yellow grease), which was used directly in the next step without purification.

Step 9

[(3S,4S,5R,6S)-3,4,5-tribenzyloxy-6-[3-[[5-(4-fluorophenyl)-2-thienyl]methyl]-4-methyl-phenyl]-2-(hydroxymethyl)-6-methoxy-tetrahydropyran-2-yl]methanol (2S,3S,4S,5R,6S)-3,4,5-tribenzyloxy-6-[3-[[5-(4-fluorophenyl)-2-thienyl]methyl]-4-methyl-phenyl]-2-(hydroxymethyl)-6-methoxy-tetrahydropyran-2-carbaldehyde 9i (2.0 g, 2.1 mmol) was dissolved in 30 mL of mixed solution (THF and MeOH, v:v=1:20), followed by addition of sodium borohydride (238 mg, 6.3 mmol) in batch. The reaction mixture was stirred for 1 hour. Thereafter, the reaction mixture was concentrated under reduced pressure and the resulting residue was purified by silica gel chromatography with elution systems B and E to obtain the title compound [(3S,4S,5R,6S)-3,4,5-tribenzyloxy-6-[3-[[5-(4-fluorophenyl)-2-thienyl]methyl]-4-methyl-phenyl]-2-(hydroxymethyl)-6-methoxy-tetrahydropyran-2-yl]methanol 9j (420 mg, pale yellow solid), yield: 25.8%. 1H NMR (400 MHz, CD3OD): δ 7.55 (d, 2H), 7.48-7.45 (m, 3H), 7.32-7.28 (m, 5H), 7.25-7.21 (m, 9H), 7.16 (d, 2H), 7.07-7.03 (m, 3H), 6.63 (d, 1H), 4.91 (d, 1H), 4.83 (d, 1H), 4.75 (d, 1H), 4.54 (d, 1H), 4.26-4.17 (m, 2H), 4.10-4.04 (m, 5H), 3.94 (d, 1H), 3.78 (d, 1H), 3.36 (d, 1H), 3.26 (s, 3H), 2.34 (s, 3H).

Step 10

(1S,2S,3S,4R,5S)-5-[3-[[5-(4-fluorophenyl)-2-thienyl]methyl]-4-methyl-phenyl]-1-(hydroxymethyl)-6,8-dioxabicyclo[3.2.1]octane-2,3,4-triol

[(3S,4S,5R,6S)-3,4,5-tribenzyloxy-6-[3-[[5-(4-fluorophenyl)-2-thienyl]methyl]-4-methyl-phenyl]-2-(hydroxymethyl)-6-methoxy-tetrahydropyran-2-yl]methanol 9j (130 mg, 0.17 mmol) was dissolved in 10 mL methanol, followed by addition of a solution (4 mL) of 2 M hydrochloric in ethyl acetate and Palladium/carbon (260 mg, 20%). The mixture was exchanged with H2 three times and stirred for 16 hours. Thereafter, the reaction mixture was filtered. The filtrate was concentrated under reduced pressure and the resulting residue was purified by HPLC to obtain the title compound (1S,2S,3S,4R,5S)-5-[3-[[5-(4-fluorophenyl)-2-thienyl]methyl]-4-methyl-phenyl]-1-(hydroxymethyl)-6,8-dioxabicyclo[3.2.1]octane-2,3,4-triol 9 (11 mg, white solid), yield: 13.8%. MS m/z (ESI): 473.2 [M+1]; 1H NMR (400 MHz, CD3OD): δ 7.57-7.56 (m, 2H), 7.48 (d, 1H), 7.39-7.37 (m, 1H), 7.19 (d, 1H), 7.15 (d, 1H), 7.10-7.06 (m, 2H), 6.67 (d, 1H), 4.18 (d, 3H), 3.88-3.81 (m, 2H), 3.73-3.68 (m, 2H), 3.65-3.62 (m, 2H), 2.33 (s, 3H).

Example 10

(1S,2S,3S,4R,5S)-5-[4-chloro-3-[[3-fluoro-4-(1,1,2,2,2-pentadeuterioethoxy)phenyl]methyl]phenyl]-1-(hydroxymethyl)-6,8-dioxabicyclo[3.2.1]octane-2,3,4-triol

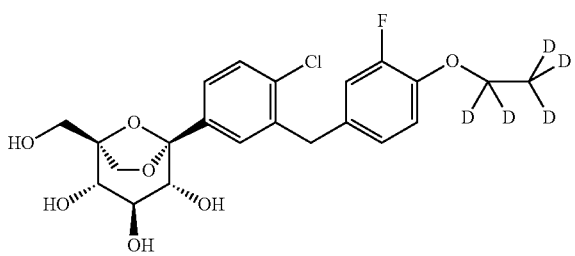

-continued
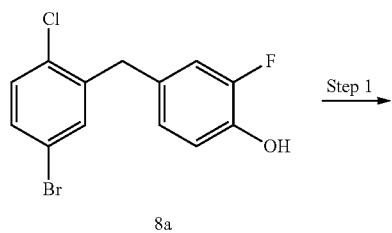
8a
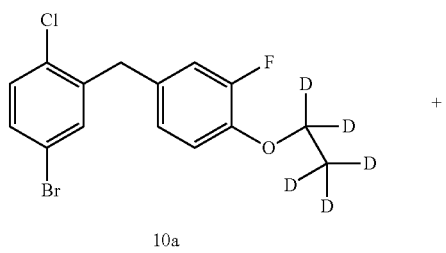
10a
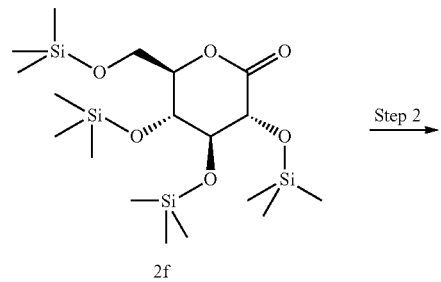
2f
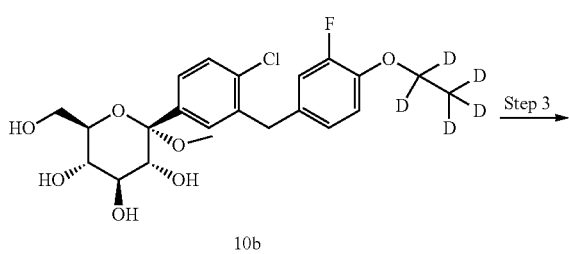
10b
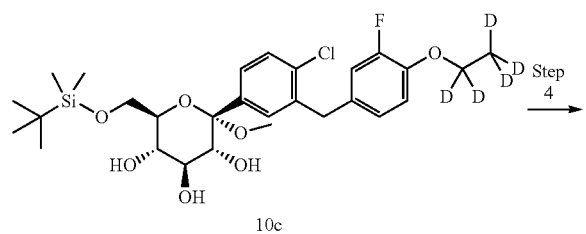
10c
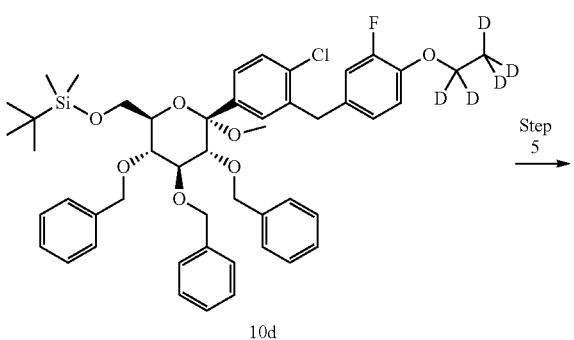
10d -continued
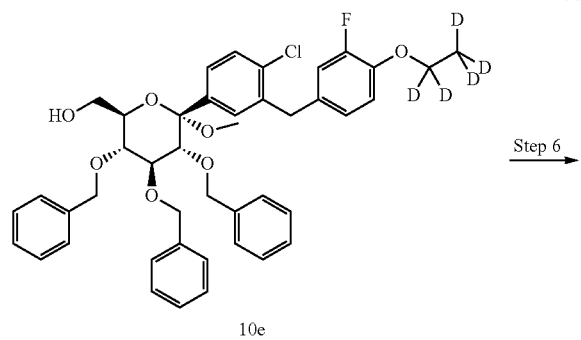
10e
Step 6 →
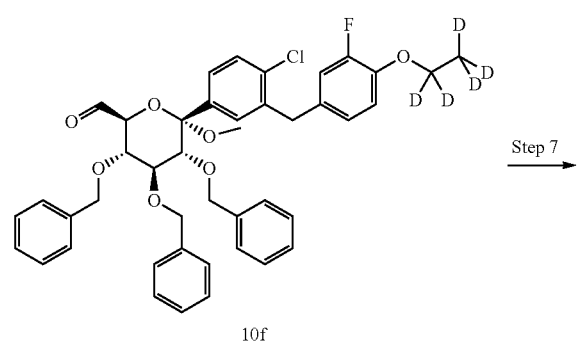
10f
Step 7 →
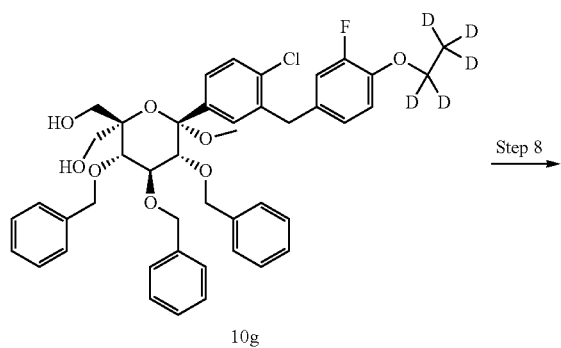
10g
Step 8 →
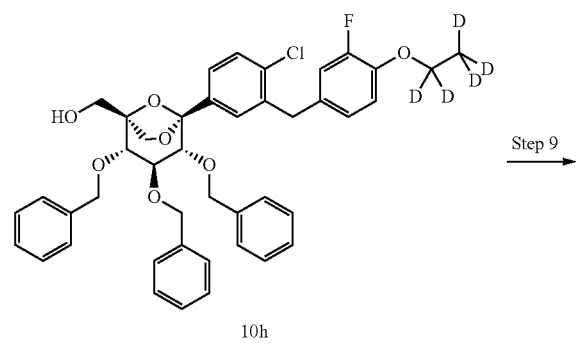
10h
Step 9 →

-continued

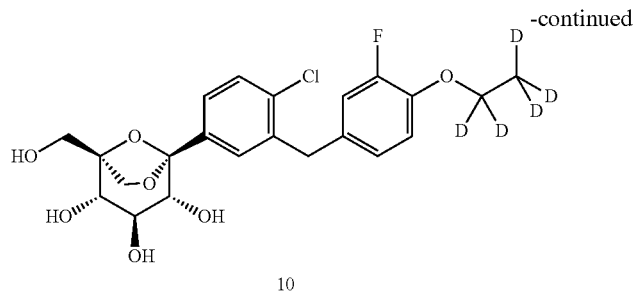
10

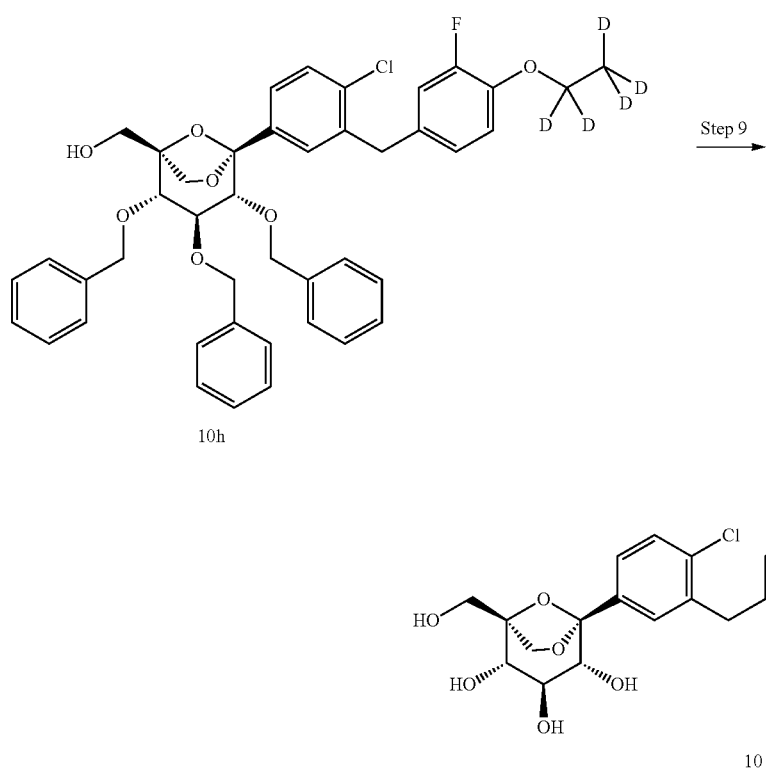

Step 1

4-[(5-bromo-2-chloro-phenyl)methyl]-2-fluoro-1-(1,1,2,2,2-pentadeuterioethoxy)benzene 4[(5-bromo-2-chloro-phenyl)methyl]-2-fluoro-phenol 8a (6.0 g, 19.05 mmol) was dissolved in 100 mL THF, followed by addition of triphenylphosphine (9.98 g, 38.1 mmol) and azodicarboxylic acid diisopropyl ester (7.7 mL, 38.1 mmol). The reaction mixture was stirred for 30 minutes. 2.5 mL ethanol-d6 were added before the reaction mixture was stirred for 18 hours. Thereafter, the reaction mixture was concentrated under reduced pressure and the resulting residue was recrystallized with petroleum ether, filtered and collected as a filter cake. The filter cake was dissolved in 50 mL methanol before 2 mL of hydrogen peroxide were added. After stirring for 1 minute, the mixture was partitioned after 5 g sodium thiosulfate, 40 mL water and 50 mL ethyl acetate were added. The aqueous phase was extracted with ethyl acetate (30 mL×3) and the organic extract was washed with saturated sodium chloride solution (30 mL), combined, dried over anhydrous magnesium sulfate and filtered. The filtrate was concentrated under reduced pressure and the resulting residue was purified by silica gel chromatography with elution system D to obtain the title compound 4-[(5-bromo-2-chloro-phenyl)methyl]-2-fluoro-1-(1,1,2,2,2-pentadeuterioethoxy)benzene 10a (5.78 g, colourless liquid), yield: 86%. 1H NMR (400 MHz, CDCl3): δ 7.38-7.24 (m, 3H), 6.99-6.83 (m, 3H), 4.02 (s, 2H).

Step 2

(2S,3R,4S,5S,6R)-2-[4-chloro-3-[[3-fluoro-4-(1,1,2,2,2-pentadeuterioethoxy)phenyl]methyl]phenyl]-6-(hydroxymethyl)-2-methoxy-tetrahydropyran-3,4,5-triol 4-[(5-bromo-2-chloro-phenyl)methyl]-2-fluoro-1-(1,1,2,2,2-pentadeuterioethoxy)benzene 10a (5.78 g, 16.6 mmol)

was dissolved in 125 mL of mixed solution (THF and n-hexane, v:v=2:3) and cooled to −78° C., followed by dropwise addition of a solution of nBuLi (8.53 g, 18.26 mmol) in n-hexane. After stirring for 2 hours at −78° C., a solution (40 mL) of (3R,4S,5R,6R)-3,4,5-tris(trimethylsilyloxy)-6-(trimethylsilyloxy-methyl)tetrahydropyran-2-one 2f (12.6 g, 27.1 mmol) in n-hexane was dropwise added. The reaction mixture was stirred for 3 hours at −78° C. 40 mL methanol and 4.79 mL methanesulfonic acid were added before the reaction mixture was warmed and stirred for 16 hours at room temperature. Thereafter, the reaction mixture was concentrated under reduced pressure and was partitioned after 40 mL saturated sodium bicarbonate solution, 100 mL ethyl acetate and 100 mL water were added. The aqueous phase was extracted with ethyl acetate (50 mL×4) and the organic extracts were combined, dried over anhydrous magnesium sulfate, and filtered. The filtrate was concentrated under reduced pressure and the resulting residue was purified by silica gel chromatography with elution system D to obtain the title compound (2S,3R,4S,5S,6R)-2-[4-chloro-3-[[3-fluoro-4-(1,1,2,2,2-pentadeuterioethoxy)phenyl]methyl]phenyl]-6-(hydroxymethyl)-2-methoxy-tetrahydropyran-3,4,5-triol 10b (1.6 g, yellow solid), yield: 20.9%.

Step 3

(2S,3R,4S,5S,6R)-6-[(tert-butyl(dimethyl)silyl)oxymethyl]-2-[4-chloro-3-[[3-fluoro-4-(1,1,2,2,2-pentadeuterioethoxy)phenyl]methyl]phenyl]-2-methoxy-tetrahydropyran-3,4,5-triol (2S,3R,4S,5S,6R)-2-[4-chloro-3-[[3-fluoro-4-(1,1,2,2,2-pentadeuterioethoxy)phenyl]methyl]phenyl]-6-(hydroxymethyl)-2-methoxy-tetrahydropyran-3,4,5-triol 10b (1.6 g, 3.47 mmol) was dissolved in 40 mL pyridine, followed by addition of 4-dimethylamino pyridine (64 mg, 0.52 mmol) and TBSCl (0.57 g, 3.8 mmol) in turn. The reaction mixture was stirred for 24 hours and concentrated under reduced pressure and was partitioned after 50 mL ethyl acetate and 50 mL water were added. The aqueous phase was extracted with ethyl acetate (30 mL×3) and the organic extract was combined, dried over anhydrous magnesium sulfate, and filtered. The filtrate was concentrated under reduced pressure and the resulting residue was purified by silica gel chromatography with elution system D to obtain the title compound (2S,3R,4S,5S,6R)-6-[(tert-butyl(dimethyl)silyl)oxymethyl]-2-[4-chloro-3-[[3-fluoro-4-(1,1,2,2,2-pentadeuterioethoxy)phenyl]methyl]phenyl]-2-methoxy-tetrahydropyran-3,4,5-triol 10c (1.7 g, yellow liquid), yield: 85%.

Step 4

[[(2R,3R,4S,5R,6S)-3,4,5-tribenzyloxy-6-[4-chloro-3-[[3-fluoro-4-(1,1,2,2,2-pentadeuterioethoxy)phenyl]methyl]phenyl]-6-methoxy-tetrahydropyran-2-yl]methoxy]tert-butyl-dimethyl-silane (2S,3R,4S,5S,6R)-6-[(tert-butyl(dimethyl)silyl)oxymethyl]-2-[4-chloro-3-[[3-fluoro-4-(1,1,2,2,2-pentadeuterioethoxy)phenyl]methyl]phenyl]-2-methoxy-tetrahydropyran-3,4,5-triol 10c (1.7 g, 2.90 mmol) was dissolved in 50 mL DMF and cooled to 0° C., followed by addition of 60% NaH (620 mg, 14.0 mmol). Then the reaction mixture was warmed to room temperature and stirred for 1 hour. Thereafter, benzyl bromide (1.90 mL, 14 mmol) was added before the mixture was stirred for 3 hours. The reaction mixture was extracted with ethyl acetate (50 mL×3) after 5 mL methanol and 100 mL water were added. The organic extract was washed with saturated sodium chloride solution (30 mL) and combined, dried over anhydrous magnesium sulfate, and filtered. The filtrate was concentrated under reduced pressure to obtain the title compound [[(2R,3R,4S,5R,6S)-3,4,5-tribenzyloxy-6-[4-chloro-3-[[3-fluoro-4-(1,1,2,2,2-pentadeuterioethoxy)phenyl]methyl]phenyl]-6-methoxy-tetrahydropyran-2-yl]methoxy]tert-butyl-dimethyl-silane 10d (2.45 g, yellow liquid), which was used directly in the next step without purification.

Step 5

[(2R,3R,4S,5R,6S)-3,4,5-tribenzyloxy-6-[4-chloro-3-[[3-fluoro-4-(1,1,2,2,2-pentadeuterioethoxy)phenyl]methyl]phenyl]-6-methoxy-tetrahydropyran-2-yl]methanol

[[(2R,3R,4S,5R,6S)-3,4,5-tribenzyloxy-6-[4-chloro-3-[[3-fluoro-4-(1,1,2,2,2-pentadeuterioethoxy)phenyl]methyl]phenyl]-6-methoxy-tetrahydropyran-2-yl]methoxy]tert-butyl-dimethyl-silane 10d (2.45 g, 2.90 mmol) was dissolved in 30 mL methanol, followed by addition of acetyl chloride (50 µL, 0.4 mmol). The reaction mixture was stirred for 4 hours. Thereafter, the reaction mixture was concentrated under reduced pressure before 30 mL water were added. Then the resulting residue was extracted with ethyl acetate (30 mL×3) and the organic extracts were combined, dried over anhydrous magnesium sulfate, and filtered. The filtrate was concentrated under reduced pressure and then the resulting residue was purified by silica gel chromatography with elution system D to obtain the title compound [(2R,3R,4S,5R,6S)-3,4,5-tribenzyloxy-6-[4-chloro-3-[[3-fluoro-4-(1,1,2,2,2-pentadeuterioethoxy)phenyl]methyl]phenyl]-6-methoxy-tetrahydropyran-2-yl]methanol 10e (1.2 g, yellow liquid), yield: 56.8%.

Step 6

(2S,3S,4S,5R,6S)-3,4,5-tribenzyloxy-6-[4-chloro-3-[[3-fluoro-4-(1,1,2,2,2-pentadeuterioethoxy)phenyl]methyl]phenyl]-6-methoxy-tetrahydropyran-2-carbaldehyde Oxalyl chloride (0.36 mL, 3.93 mmol) was dissolved in 5 mL dichloromethane and cooled to −78° C. 10 mL solution of dimethyl sulfoxide (0.35 mL, 4.92 mmol) in dichloromethane were added and stirred for 15 minutes, then 15 mL solution of [(2R,3R,4S,5R,6S)-3,4,5-tribenzyloxy-6-[4-chloro-3-[[3-fluoro-4-(1,1,2,2,2-pentadeuterioethoxy)phenyl]methyl]phenyl]-6-methoxy-tetrahydropyran-2-yl]methanol 10e (1.2 g, 1.64 mmol) in dichloromethane were added and stirred for 45 minutes. Then triethylamine (1.2 mL, 8.2 mmol) was added before the reaction mixture was warmed and stirred for 2.5 hours at room temperature. Thereafter, the reaction mixture was extracted with dichloromethane (15 mL×2) after 5 mL 1 M hydrochloric acid were added. The organic extracts were combined, dried over anhydrous magnesium sulfate, and filtered. The filtrate was concentrated under reduced pressure to obtain the title compound (2S,3S,4S,5R,6S)-3,4,5-tribenzyloxy-6-[4-chloro-3-[[3-fluoro-4-(1,1,2,2,2-pentadeuterioethoxy)phenyl]methyl]phenyl]-6-methoxytetrahydropyran-2-carbaldehyde 10f (1.2 g, yellow liquid), which was used directly in the next step without purification.

Step 7

[(3S,4S,5R,6S)-3,4,5-tribenzyloxy-6-[4-chloro-3-[[3-fluoro-4-(1,1,2,2,2-pentadeuterioethoxy)phenyl] methyl]phenyl]-2-(hydroxymethyl)-6-methoxy-tetrahydropyran-2-yl]methanol (2S,3S,4S,5R,6S)-3,4,5-tribenzyloxy-6-[4-chloro-3-[[3-fluoro-4-(1,1,2,2,2-pentadeuterioethoxy)phenyl]methyl] phenyl]-6-methoxy-tetrahydropyran-2-carbaldehyde 10f (1.2 g, 1.64 mmol) was dissolved in 40 mL 1,4-dioxane, followed by addition of formaldehyde solution (2.2 mL, 7.54 mmol), potassium hydroxide (0.27 g, 4.92 mmol) and benzyl alcohol (177 mg, 1.64 mmol). The reaction mixture was stirred for 6 hours at 50° C. Thereafter, the reaction mixture was extracted with ethyl acetate (20 mL×3) after 20 mL water were added. The organic extracts were combined, dried over anhydrous magnesium sulfate, and filtered. The filtrate was concentrated under reduced pressure to obtain the title compound [(3S,4S,5R,6S)-3,4,5-tribenzyloxy-6-[4-chloro-3-[[3-fluoro-4-(1,1,2,2,2-pentadeuterioethoxy)phenyl]methyl] phenyl]-2-(hydro-oxymethyl)-6-methoxy-tetrahydropyran-2-yl]methanol 10g (0.64 g, yellow liquid), which was used directly in the next step without purification.

Step 8

[(1S,2S,3S,4R,5S)-2,3,4-tribenzyloxy-5-[4-chloro-3-[[3-fluoro-4-(1,1,2,2,2-pentadeuterioethoxy)phenyl] methyl]phenyl]-6,8-dioxabicyclo[3.2.1]octan-1-yl] methanol

[(3S,4S,5R,6S)-3,4,5-tribenzyloxy-6-[4-chloro-3-[[3-fluoro-4-(1,1,2,2,2-pentadeuterioethoxy)phenyl]methyl] phenyl]-2-(hydroxymethyl)-6-methoxy-tetrahydropyran-2-yl]methanol 10g (640 mg, 0.83 mmol) was dissolved in 20 mL methylene chloride, followed by dropwise addition of trifluoroacetic acid (0.5 mL). The mixture was stirred for 2 hours. Thereafter, the reaction mixture was concentrated under reduced pressure and the resulting residue was purified by silica gel chromatography with elution system D to obtain the title compound [(1S,2S,3S,4R,5S)-2,3,4-tribenzyloxy-5-[4-chloro-3-[[3-fluoro-4-(1,1,2,2,2-pentadeuterioethoxy) phenyl]methyl]phenyl]-6,8-dioxabicyclo[3.2.1]octan-1-yl] methanol 10h (300 mg, pale yellow solid), yield: 41.0%. MS m/z (ESI): 747.3 [M+18].

Step 9

(1S,2S,3S,4R,5S)-5-[4-chloro-3-[[3-fluoro-4-(1,1,2,2,2-pentadeuterioethoxy)phenyl]methyl]phenyl]-1-(hydroxymethyl)-6,8-dioxabicyclo[3.2.1]octane-2,3,4-triol

[(1S,2S,3S,4R,5S)-2,3,4-tribenzyloxy-5-[4-chloro-3-[[3-fluoro-4-(1,1,2,2,2-pentadeuterioethoxy)phenyl]methyl] phenyl]-6,8-dioxabicyclo[3.2.1]octan-1-yl]methanol 10h (300 mg, 0.41 mmol) was dissolved in 30 mL of mixed solution (THF and MeOH, v:v=1:1), followed by addition of 1,2-dichlorobenzene (600 mg, 4.10 mmol) and Palladium/carbon (30 mg, 10%) in turn. The mixture was exchanged with H2 three times and stirred for 3 hours. Thereafter, the reaction mixture was filtered. The filtrate was concentrated under reduced pressure and the resulting residue was purified by reversed-phase column chromatography with elution system F to obtain the title compound (1S,2S,3S,4R,5S)-5-[4-chloro-3-[[3-fluoro-4-(1,1,2,2,2-pentadeuterioethoxy)phenyl]methyl]phenyl]-1-(hydroxymethyl)-6,8-dioxabicyclo [3.2.1]octane-2,3,4-triol 10 (134 mg, white solid), yield: 70.0%. MS m/z (ESI): 477.1 [M+18]; 1H NMR (400 MHz, CD3OD): δ 7.49 (d, 1H), 7.46-7.30 (m, 2H), 7.05-6.81 (m, 3H), 4.17 (d, 1H), 4.06 (s, 2H), 3.86 (d, 1H), 3.79 (s, 1H), 3.75-3.51 (m, 4H).

Example 11

(1S,2S,3S,4R,5S)-5-[4-chloro-3-[dideuterio-(4-ethoxy-3-fluoro-phenyl)methyl]phenyl]-1-(hydroxymethyl)-6,8-dioxabicyclo[3.2.1]octane-2,3,4-triol

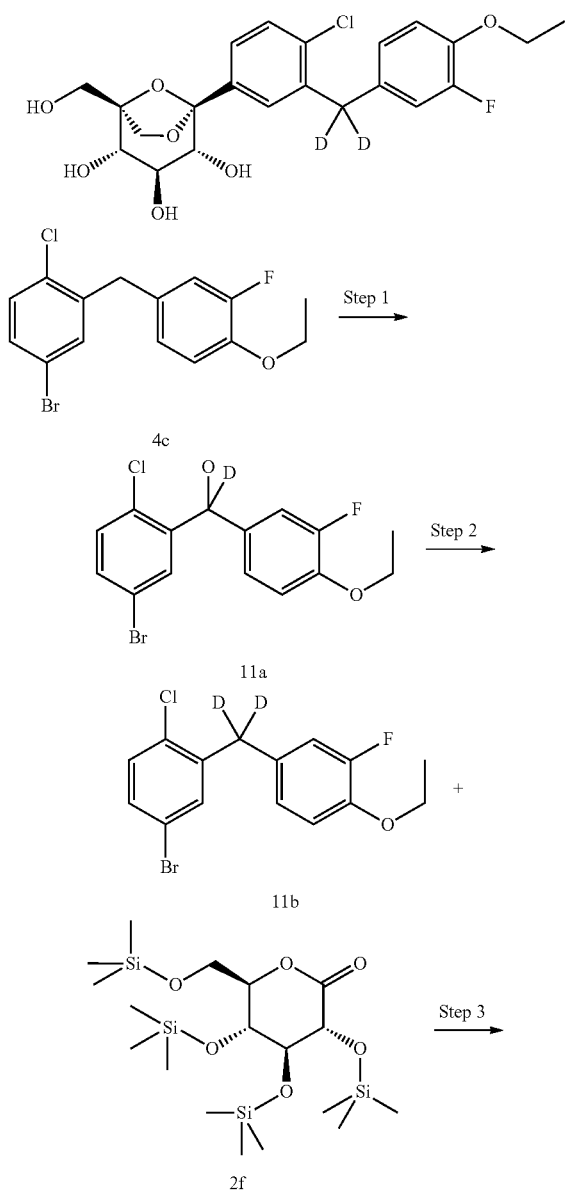

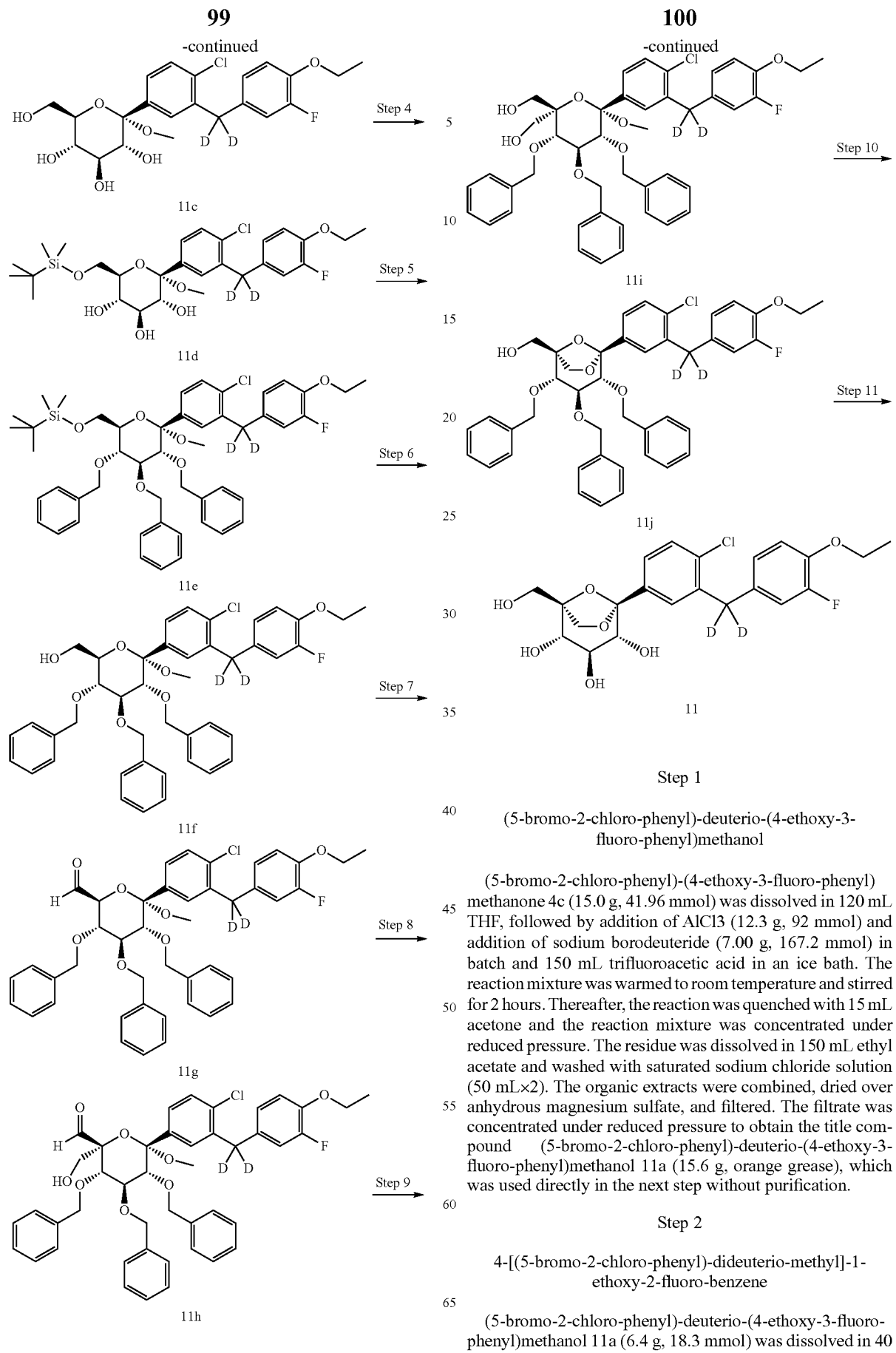

Step 1

(5-bromo-2-chloro-phenyl)-deuterio-(4-ethoxy-3-fluoro-phenyl)methanol (5-bromo-2-chloro-phenyl)-(4-ethoxy-3-fluoro-phenyl) methanone 4c (15.0 g, 41.96 mmol) was dissolved in 120 mL THF, followed by addition of AlCl3 (12.3 g, 92 mmol) and addition of sodium borodeuteride (7.00 g, 167.2 mmol) in batch and 150 mL trifluoroacetic acid in an ice bath. The reaction mixture was warmed to room temperature and stirred for 2 hours. Thereafter, the reaction was quenched with 15 mL acetone and the reaction mixture was concentrated under reduced pressure. The residue was dissolved in 150 mL ethyl acetate and washed with saturated sodium chloride solution (50 mL×2). The organic extracts were combined, dried over anhydrous magnesium sulfate, and filtered. The filtrate was concentrated under reduced pressure to obtain the title compound (5-bromo-2-chloro-phenyl)-deuterio-(4-ethoxy-3-fluoro-phenyl)methanol 11a (15.6 g, orange grease), which was used directly in the next step without purification.

Step 2

4-[(5-bromo-2-chloro-phenyl)-dideuterio-methyl]-1-ethoxy-2-fluoro-benzene (5-bromo-2-chloro-phenyl)-deuterio-(4-ethoxy-3-fluoro-phenyl)methanol 11a (6.4 g, 18.3 mmol) was dissolved in 40 mL trifluoroacetic acid, followed by addition of sodium borodeuteride (1.6 g, 38 mmol). The reaction mixture was stirred for 3 hours. Thereafter, the mixture was quenched with 50 mL saturated sodium bicarbonate solution and partitioned. The aqueous phase was extracted with ethyl acetate (100 mL×2) and the organic extract was combined, dried over anhydrous magnesium sulfate, and filtered. The filtrate was concentrated under reduced pressure and the resulting residue was purified by silica gel chromatography with elution system B to obtain the title compound 4-[(5-bromo-2-chloro-phenyl)-dideuterio-methyl]-1-ethoxy-2-fluoro-benzene 11b (4.3 g, colourless grease), yield: 67.8%. 1H NMR (400 MHz, CDCl$_3$): δ 7.43-7.23 (m, 3H), 7.03-6.85 (m, 3H), 4.21-4.08 (m, 2H), 1.54-1.44 (m, 3H).

Step 3

(2S,3R,4S,5S,6R)-2-[4-chloro-3-[dideuterio-(4-ethoxy-3-fluoro-phenyl)methyl]phenyl]-6-(hydroxymethyl)-2-methoxy-tetrahydropyran-3,4,5-triol 4-[(5-bromo-2-chloro-phenyl)-dideuterio-methyl]-1-ethoxy-2-fluoro-benzene 11b (5.00 g, 16.4 mmol) was dissolved in a mixed solution of 50 mL THF and 75 mL n-hexane and cooled to −78° C., followed by dropwise addition of nBuLi (9.00 mL, 21.6 mmol). After stirring for 2 hours at −78° C., a solution (30 mL) of (3R,4S,5R,6R)-3,4,5-tris(trimethylsilyloxy)-6-(trimethylsilyloxymethyl)tetrahydropyran-2-one 2f (7.4 g, 15.8 mmol) in n-hexane was added and the reaction mixture was stirred for 2 hours at −78° C. 3.5 mL methanesulfonic acid and 40 mL methanol were added before the reaction mixture was warmed and stirred for 16 hours at room temperature. Thereafter, the mixture was quenched with 100 mL saturated sodium carbonate solution and concentrated under reduced pressure. The residue was dissolved after 50 mL saturated sodium chloride solution were added and extracted with ethyl acetate (100 mL×3). The organic extracts were combined, dried over anhydrous magnesium sulfate, and filtered. The filtrate was concentrated under reduced pressure and the resulting residue was purified by silica gel chromatography with elution system A to obtain the title compound (2S,3R,4S,5S,6R)-2-[4-chloro-3-[dideuterio-(4-ethoxy-3-fluorophenyl)methyl]phenyl]-6-(hydroxymethyl)-2-methoxy-tetrahydropyran-3,4,5-triol 11c (2.4 g, colourless liquid), yield: 36.4%. 1H NMR (400 MHz, CDCl3): δ 7.57-7.34 (m, 3H), 7.04-6.81 (m, 3H), 4.20-3.80 (m, 8H), 3.52 (s, 3H), 2.54 (br. s., 4H), 1.41-1.24 (m, 3H).

Step 4

(2S,3R,4S,5S,6R)-6-[(tert-butyl(dimethyl)silyl)oxymethyl]-2-[4-chloro-3-[dideuterio-(4-ethoxy-3-fluoro-phenyl)methyl]phenyl]-2-methoxy-tetrahydropyran-3,4,5-triol (2S,3R,4S,5S,6R)-2-[4-chloro-3-[dideuterio-(4-ethoxy-3-fluoro-phenyl)methyl]phenyl]-6-(hydroxymethyl)-2-methoxy-tetrahydropyran-3,4,5-triol 11c (2.4 g, 5.24 mmol) was dissolved in 40 mL dichloromethane, followed by addition of DMAP (97 mg, 0.79 mmol), imidazole (1.07 mg, 15.7 mmol) and TBSCl (0.87 g, 5.76 mmol) in turn. The reaction mixture was stirred for 16 hours. Thereafter, the reaction mixture was concentrated under reduced pressure. The residue was washed with saturated copper sulfate solution (50 mL×3) after 200 mL ethyl acetate were added. The organic extracts were combined, dried over anhydrous magnesium sulfate, and filtered. The filtrate was concentrated under reduced pressure to obtain the title compound (2S,3R,4S,5S,6R)-6-[(tert-butyl(dimethyl)silyl)oxymethyl]-2-[4-chloro-3-[dideuterio-(4-ethoxy-3-fluoro-phenyl)methyl]phenyl]-2-methoxy-tetrahydropyran-3,4,5-triol 11d (2.87 g, pale yellow solid), which was used directly in the next step without purification.

Step 5

[[(2R,3R,4S,5R,6S)-3,4,5-tribenzyloxy-6-[4-chloro-3-[dideuterio-(4-ethoxy-3-fluorophenyl)methyl]phenyl]-6-methoxy-tetrahydropyran-2-yl]methoxy]tert-butyl-dimethyl-silane (2S,3R,4S,5S,6R)-6-[(tert-butyl(dimethyl)silyl)oxymethyl]-2-[4-chloro-3-[dideuterio-(4-ethoxy-3-fluoro-phenyl)methyl]phenyl]-2-methoxy-tetrahydropyran-3,4,5-triol 11d (2.87 g, 5.02 mmol) was dissolved in 60 mL DMF, followed by addition of 60% NaH (1.00 g, 25.1 mmol) in an ice bath. Then the reaction mixture was warmed to room temperature and stirred for 40 minutes, before benzyl bromide (3.00 mL, 25.1 mmol) was added and stirred for 3 hours. The reaction was quenched with 20 mL methanol and the reaction mixture was concentrated under reduced pressure. The resulting residue was dissolved in 200 mL ethyl acetate and 50 mL water and partitioned. The aqueous phase was extracted with 50 mL ethyl acetate. The organic extracts were washed with 50 mL water and 50 mL saturated sodium chloride solution in turn, and combined, dried over anhydrous magnesium sulfate, and filtered. The filtrate was concentrated under reduced pressure to obtain the title compound [[(2R,3R,4S,5R,6S)-3,4,5-tribenzyloxy-6-[4-chloro-3-[dideuterio-(4-ethoxy-3-fluorophenyl)methyl]phenyl]-6-methoxy-tetrahydropyran-2-yl]methoxy]tert-butyl-dimethyl-silane 11e (3.00 g, yellow grease), yield: 99.8%.

Step 6

[(2R,3R,4S,5R,6S)-3,4,5-tribenzyloxy-6-[4-chloro-3-[dideuterio-(4-ethoxy-3-fluorophenyl)methyl]phenyl]-6-methoxy-tetrahydropyran-2-yl]methanol

[[(2R,3R,4S,5R,6S)-3,4,5-tribenzyloxy-6-[4-chloro-3-[dideuterio-(4-ethoxy-3-fluorophenyl)methyl]phenyl]-6-methoxy-tetrahydropyran-2-yl]methoxy]tert-butyl-dimethyl-silane 11e (4.22 g, 5.02 mmol) was dissolved in 30 mL methanol and stirred for 1 hour after addition of acetyl chloride (0.05 mL, 0.75 mmol). Thereafter, the reaction mixture was concentrated under reduced pressure and the resulting residue was purified by silica gel chromatography with elution system B to obtain the title compound [(2R,3R,4S,5R,6S)-3,4,5-tribenzyloxy-6-[4-chloro-3-[dideuterio-(4-ethoxy-3-fluorophenyl)methyl]phenyl]-6-methoxy-tetrahydropyran-2-yl]methanol 11f (1.45 g, yellow grease), yield: 55.0%.

Step 7

(2S,3S,4S,5R,6S)-3,4,5-tribenzyloxy-6-[4-chloro-3-[dideuterio-(4-ethoxy-3-fluorophenyl)methyl]phenyl]-6-methoxy-tetrahydropyran-2-carbaldehyde Oxalyl chloride (0.3 mL, 3.57 mmol) was dissolved in 20 mL dichloromethane and cooled to −78° C. 10 mL solution of dimethyl sulfoxide (0.39 mL, 5.48 mmol) in dichloromethane were added before 15 mL solution of [(2R,3R,4S,5R,6S)-3,4,5-tribenzyloxy-6-[4-chloro-3-[dideuterio-(4-ethoxy-3- fluoro-phenyl)methyl]phenyl]-6-methoxy-tetrahydropyran-2-yl]methanol 11f (2 g, 2.74 mmol) in methylene chloride were added in turn and stirred for 30 minutes at −78° C. Thereafter, the mixture was warmed to room temperature and stirred for 2 hours after triethylamine (1.9 mL, 13.7 mmol) was added. The mixture was quenched with 5 mL 1 M hydrochloric acid and partitioned. The aqueous phase was extracted with dichloromethane (20 mL) and the organic extract was washed with saturated sodium chloride solution (20 mL×2), combined, dried over anhydrous magnesium sulfate, and filtered. The filtrate was concentrated under reduced pressure to obtain the title compound (2S,3S,4S,5R,6S)-3,4,5-tribenzyloxy-6-[4-chloro-3-[dideuterio-(4-ethoxy-3-fluoro-phenyl) methyl]phenyl]-6-methoxy-tetrahydropyran-2-carbaldehyde 11g (2.00 g, yellow grease), which was used directly in the next step without purification.

Step 8

(2S,3S,4S,5R,6S)-3,4,5-tribenzyloxy-6-[4-chloro-3-[dideuterio-(4-ethoxy-3-fluorophenyl)methyl]phenyl]-2-(hydroxymethyl)-6-methoxy-tetrahydropyran-2-carbaldehyde (2S,3S,4S,5R,6S)-3,4,5-tribenzyloxy-6-[4-chloro-3-[dideuterio-(4-ethoxy-3-fluorophenyl)methyl]phenyl]-6-methoxy-tetrahydropyran-2-carbaldehyde 11g (2.00 g, 2.74 mmol) was dissolved in 30 mL 1,4-dioxane, followed by addition of 4.1 mL 37% formaldehyde solution and sodium hydroxide solution (330 mg, 2.74 mmol) in turn. The reaction mixture was stirred for 6 hours at 70° C. Thereafter, the reaction mixture was extracted with ethyl acetate (20 mL×4) after 20 mL saturated sodium chloride solution were added. The organic extract was washed with saturated sodium bicarbonate (20 mL) and saturated sodium chloride solution (20 mL) and combined, dried over anhydrous magnesium sulfate and filtered. The filtrate was concentrated under reduced pressure to obtain the title compound (2S,3S,4S,5R,6S)-3,4,5-tribenzyloxy-6-[4-chloro-3-[dideuterio-(4-ethoxy-3-fluorophenyl)methyl]phenyl]-2-(hydroxymethyl)-6-methoxy-tetrahydropyran-2-carbaldehyde 11h (2.1 g, yellow grease), which was used directly in the next step without purification.

Step 9

[(3S,4S,5R,6S)-3,4,5-tribenzyloxy-6-[4-chloro-3-[dideuterio-(4-ethoxy-3-fluorophenyl)methyl]phenyl]-2-(hydroxymethyl)-6-methoxy-tetrahydropyran-2-yl]methanol (2S,3S,4S,5R,6S)-3,4,5-tribenzyloxy-6-[4-chloro-3-[dideuterio-(4-ethoxy-3-fluoro-phenyl)methyl]phenyl]-2-(hydroxymethyl)-6-methoxy-tetrahydropyran-2-carbaldehyde 11h (2.07 g, 2.74 mmol) was dissolved in 30 mL of mixed solution (THF and MeOH, v:v=2:3), followed by addition of sodium borohydride (200 mg, 5.48 mmol). The reaction mixture was stirred for 2 hours. Thereafter, the reaction was quenched with a small amount of acetone and the reaction mixture was concentrated under reduced pressure. The resulting residue was purified by silica gel chromatography with elution system A to obtain the title compound [(3S,4S,5R, 6S)-3,4,5-tribenzyloxy-6-[4-chloro-3-[dideuterio-(4-ethoxy-3-fluoro-phenyl)methyl]phenyl]-2-(hydroxymethyl)-6-methoxy-tetrahydropyran-2-yl]methanol 11i (0.20 g, colourless grease), yield: 10%.

1H NMR (400 MHz, CDCl3): δ 7.39-7.19 (m, 16H), 7.04 (dd, 2H), 6.89-6.74 (m, 3H), 5.03-4.86 (m, 3H), 4.72-4.59 (m, 2H), 4.45-4.30 (m, 2H), 4.05 (q, 2H), 3.98 (dd, 2H), 3.90-3.80 (m, 2H), 3.75-3.62 (m, 1H), 3.25 (d, 1H), 3.06 (s, 3H), 1.42 (t, 3H).

Step 10

[(1S,2S,3S,4R,5S)-2,3,4-tribenzyloxy-5-[4-chloro-3-[dideuterio-(4-ethoxy-3-fluorophenyl)methyl]phenyl]-6,8-dioxabicyclo[3.2.1]octan-1-yl]methanol

[(3S,4S,5R,6S)-3,4,5-tribenzyloxy-6-[4-chloro-3-[dideuterio-(4-ethoxy-3-fluoro-phenyl)methyl]phenyl]-2-(hydroxymethyl)-6-methoxy-tetrahydropyran-2-yl]methanol 11i (0.50 g, 6.60 mmol) was dissolved in 2 mL dichloromethane and cooled to −10° C., before 1 mL trifluoroacetic acid was added. The reaction mixture was warmed and stirred for 2 hours at room temperature. Thereafter, the reaction was quenched with 5 mL saturated sodium bicarbonate and partitioned. The reaction mixture was concentrated under reduced pressure and the resulting residue was purified by silica gel chromatography with elution system B to obtain the title compound [(1S,2S,3S,4R,5S)-2,3,4-tribenzyloxy-5-[4-chloro-3-[dideuterio-(4-ethoxy-3-fluoro-phenyl)methyl] phenyl]-6,8-dioxabicyclo[3.2.1]octan-1-yl]methanol 11j (300 mg, white solid), yield: 62.6%. MS m/z (ESI): 744.0 [M+18].

Step 11

(1S,2S,3S,4R,5S)-5-[4-chloro-3-[dideuterio-(4-ethoxy-3-fluoro-phenyl)methyl]phenyl]-1-(hydroxymethyl)-6,8-dioxabicyclo[3.2.1]octane-2,3,4-triol

[(1S,2S,3S,4R,5S)-2,3,4-tribenzyloxy-5-[4-chloro-3-[dideuterio-(4-ethoxy-3-fluorophenyl)methyl]phenyl]-6,8-dioxabicyclo[3.2.1]octan-1-yl]methanol 11j (300 mg, 0.41 mmol) was dissolved in 10 mL of mixed solution (THF and MeOH, v:v=1:1), followed by addition of o-dichlorobenzene (600 mg, 0.41 mmol) and Palladium/carbon (30 mg, 10%). The mixture was exchanged with H2 three times and stirred for 3 hours. Thereafter, the reaction mixture was filtered and eluted with a small amount of ethyl acetate. The filtrate was concentrated under reduced pressure. The resulting residue was purified by silica gel chromatography with elution system A to obtain the title compound (1S,2S,3S,4R,5S)-5-[4-chloro-3-[dideuterio-(4-ethoxy-3-fluoro-phenyl)methyl] phenyl]-1-(hydroxymethyl)-6,8-dioxabicyclo[3.2.1]octane-2,3,4-triol 11 (143 mg, white solid), yield: 76.0%. MS m/z (ESI): 474.1 [M+18]

1H NMR (400 MHz, CD3OD): δ 7.49 (d, 1H), 7.45-7.36 (m, 2H), 7.00-6.88 (m, 3H), 4.17 (d, 1H), 4.08 (q, 2H), 3.89-3.77 (m, 2H), 3.73-3.54 (m, 4H), 1.40 (t, 3H).

Example 12
(1S,2S,3S,4R,5S)-5-[4-chloro-3-[[4-(2,2-difluoroethoxy)phenyl]methyl]phenyl]-1-(hydroxymethyl)-6,8-dioxabicyclo[3.2.1]octane-2,3,4-triol
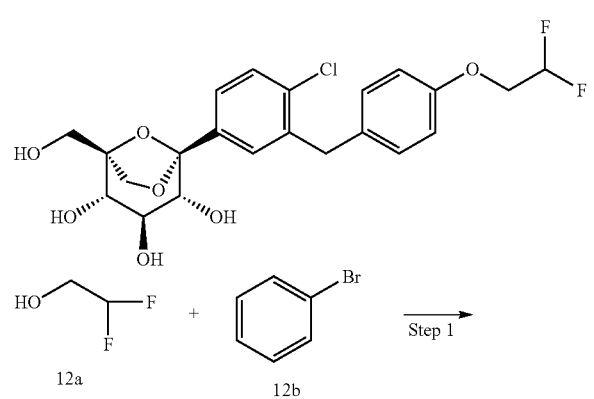
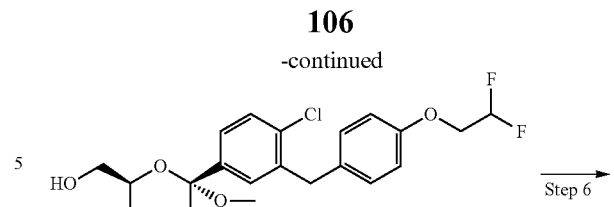
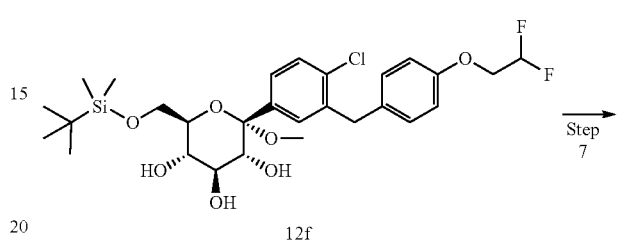
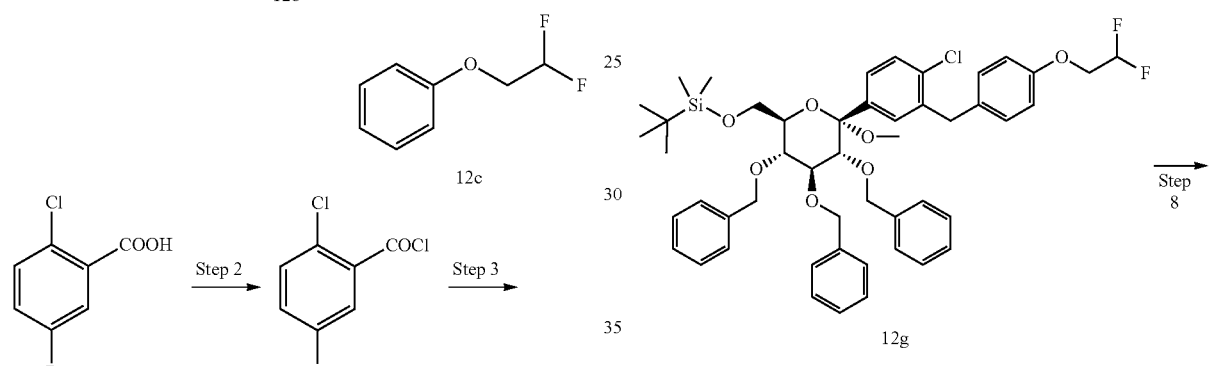
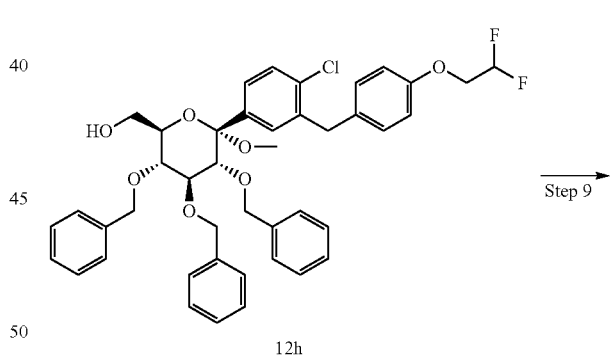
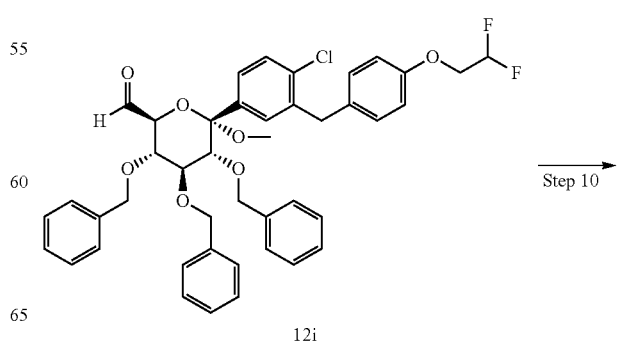

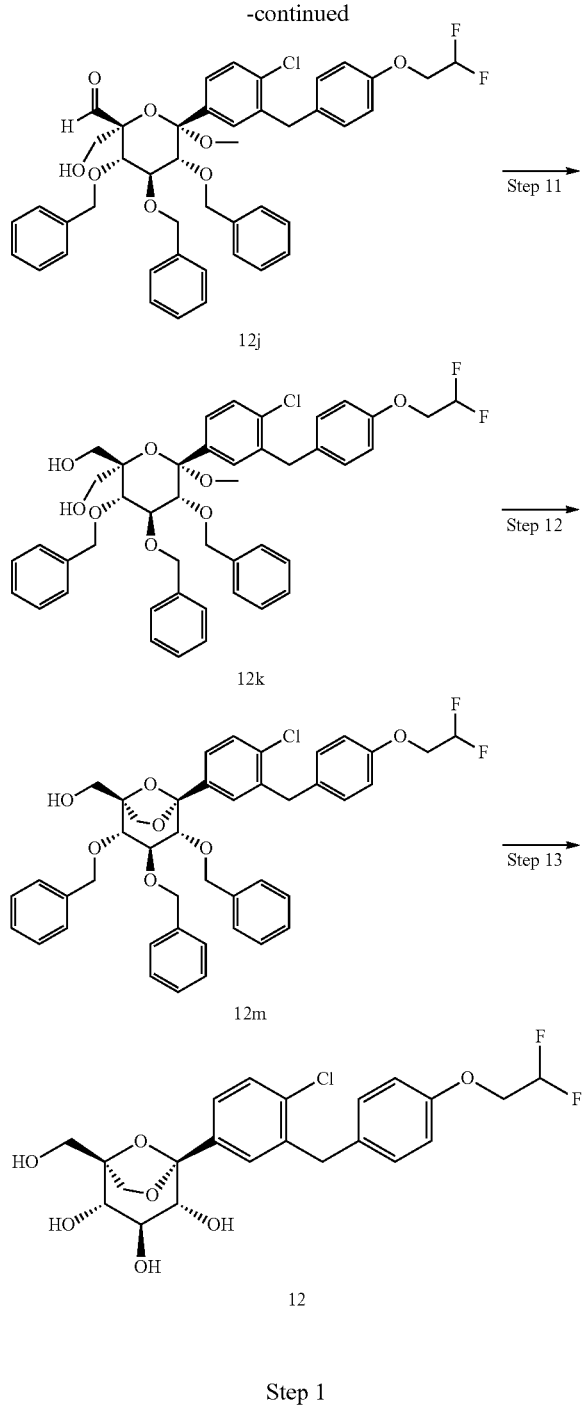

Step 1

2,2-difluoroethoxybenzene

Under N2, 60% NaH (10.2 g, 254.27 mmol) and 40 mL DMF were added into a 500 mL reaction flask and cooled to 0° C. 2,2-difluoroethanol 12a (23 g, 280.3 mmol) was dissolved in 40 mL DMF and then dropwise added into the mixture within 4 hours at 0° C. The reaction mixture was then warmed to room temperature. After 30 minutes, a solution of bromobenzene (39.92 g, 254.25 mmol) in DMF (40 mL) and CuBr (0.35 g, 2.43 mmol) were added in turn before the reaction mixture was warmed and stirred for 16 hours at 160° C. Thereafter, the reaction mixture was cooled to room temperature and filtered. The filtrate was washed with n-hexane.

5% hydrochloric acid (160 mL) was added to the filtrate before the resulting residue was extracted with n-hexane (160 mL×3). The organic extract was washed with saturated sodium chloride solution (50 mL) and combined, dried over anhydrous magnesium sulfate, and filtered. The filtrate was concentrated under reduced pressure to obtain the title compound 2,2-difluoroethoxybenzene 12c (32.97 g, yellow liquid), yield: 82.0%.

Step 2

2-chloro-5-bromo-benzoyl chloride

Under Ar protection, 5-bromo-2-chloro-benzoic acid (35 g, 148.6 mmol) was dissolved in toluene (230 ml), followed by addition of DMF (0.5 mL) at room temperature, then the reaction mixture was cooled to 0° C. The reaction mixture was heated to 100° C. after thionyl chloride (44 g, 372 mmol) was dropwise added. After 5 hours, the reaction mixture was concentrated under reduced pressure to obtain the title compound 5-bromo-2-chloro-benzoyl chloride 12n (35.5 g, pale yellow grease), yield: 94.0%.

Step 3

(5-bromo-2-chloro-phenyl)-[4-(2,2-difluoroethoxy)phenyl]methanone

Under Ar protection, 5-bromo-2-chloro-benzoyl chloride 12n (37.7 g, 148.6 mmol) was dissolved in 350 mL dichloromethane and 2,2-difluoroethoxybenzene 12c (25 g, 158.6 mmol) was added and stirred until dissolved, and cooled to 0° C., followed by addition of AlCl3 (19.1 g, 142.4 mmol) in batch. The reaction mixture was stirred for 2 hours at 0° C., then poured into 300 mL ice water and stirred for 30 minutes and partitioned. The aqueous layer was extracted with dichloromethane (100 mL). The organic layer was combined and partitioned after methanol (50 mL), dichloromethane (100 mL) and water (200 mL) were added. The organic layer was washed with saturated NaCl solution (200 mL) and combined, dried over anhydrous magnesium sulfate, and filtered. The filtrate was concentrated under reduced pressure to obtain the title compound (5-bromo-2-chloro-phenyl)-[4-(2,2-difluoroethoxy)phenyl]methanone 12o (56 g, yellow grease), yield: 99.0%.

Step 4

4-bromo-1-chloro-2-[[4-(2,2-difluoroethoxy)phenyl]methyl]benzene

Under Ar protection, (5-bromo-2-chloro-phenyl)-[4-(2,2-difluoroethoxy)phenyl]methanone 12o (55.7 g, 148.6 mmol) was dissolved in 400 mL acetonitrile, triethyl silane (46.54 g, 401.22 mmol) was added and cooled to 0° C., followed by the slow dropwise addition of boron trifluoride etherate (57 g, 401.22 mmol). Then the reaction mixture was heated to 50° C. and stirred for 16 hours. Thereafter, the reaction mixture was cooled to room temperature before MTBE (200 mL) was added and 300 mL saturated sodium bicarbonate solution were dropwise added, and partitioned. The organic extracts were washed with 200 mL saturated NaCl solution and combined, dried over anhydrous magnesium sulfate, and filtered. The filtrate was concentrated under reduced pressure and the resulting residue was purified by column chromatography to obtain the title compound 4-bromo-1-chloro-2-[[4-(2,2-difluoroethoxy)phenyl]methyl]benzene 12p (20 g, colourless grease), yield: 20.0%. MS m/z (ESI): 362.0 [M+1].

Step 5

(2S,3R,4S,5S,6R)-2-[4-chloro-3-[[4-(2,2-difluoroethoxy)phenyl]methyl]phenyl]-6-(hydroxymethyl)-2-methoxy-tetrahydropyran-3,4,5-triol Under Ar protection, 4-bromo-1-chloro-2-[[4-(2,2-difluoroethoxy)phenyl]methyl]benzene 12p (26.5 g, 73.3 mmol), MTBE (266 mL) and n-hexane (133 mL) were added into a 1 L reaction flask, stirred uniformly and cooled to −78° C., followed by dropwise addition of 2.4 M nBuLi (52 mL, 124.6 mmol) in 30 minutes. After stirring for 50 minutes at −78° C., a mixed solution of (3R,4S,5R,6R)-3,4,5-tris(trimethylsilyloxy)-6-(trimethylsilyloxymethyl)tetrahydropyran-2-one 2f (55 g, 117.3 mmol) in MTBE and n-hexane (60 mL:30 mL) was added within 20 minutes at −78° C. before the reaction mixture was stirred for 4 hours at −78° C. Thereafter, 130 mL methanol were added before stirring for 20 minutes. Then the reaction mixture was warmed to room temperature and stirred for 16 hours after methanesulfonic acid (25 g, 256.55 mmol) was added. 500 mL saturated sodium bicarbonate were added to the reaction mixture, stirred for 1 hour and partitioned. The aqueous phase was extracted with MTBE (100 mL×2) and the organic extract was combined, concentrated and purified by column chromatography (eluant: dichloromethane: methanol=100:1~10:1) to obtain the title compound (2S,3R,4S,5S,6R)-2-[4-chloro-3-[[4-(2,2-difluoroethoxy)phenyl]methyl]phenyl]-6-(hydroxymethyl)-2-methoxy-tetrahydropyran-3,4,5-triol 12e (5 g, pale yellow solid), yield: 10%. MS m/z (ESI): 492.46 [M+18].

Step 6

(2S,3R,4S,5S,6R)-6-[(tert-butyl(dimethyl)silyl)oxymethyl]-2-[4-chloro-3-[[4-(2,2-difluoroethoxy)phenyl]methyl]phenyl]-2-methoxy-tetrahydropyran-3,4,5-triol (2S,3R,4S,5S,6R)-2-[4-chloro-3-[[4-(2,2-difluoroethoxy)phenyl]methyl]phenyl]-6-(hydroxymethyl)-2-methoxy-tetrahydropyran-3,4,5-triol 12e (4 g, 8.43 mmol) was dissolved in 40 mL dichloromethane, followed by addition of DMAP (103 mg, 0.84 mmol), TBSCl (1.4 g, 9.27 mmol) and imidazole (1.72 g, 25.3 mmol) in turn. The reaction mixture was stirred for 16 hours. 40 mL saturated sodium bicarbonate were added before the reaction mixture was stirred and partitioned. Thereafter, the organic extract was washed with 0.1 N hydrochloric acid (20 mL) and saturated sodium chloride solution (40 mL), dried over anhydrous magnesium sulfate, and filtered. The filtrate was concentrated under reduced pressure to obtain the title compound (2S,3R,4S,5S,6R)-6-[(tert-butyl(dimethyl)silyl)oxymethyl]-2-[4-chloro-3-[[4-(2,2-difluoroethoxy)phenyl]methyl]phenyl]-2-methoxy-tetrahydropyran-3,4,5-triol 12f (4.96 g, pale yellow solid), yield: 100%.

Step 7

[[(2R,3R,4S,5R,6S)-3,4,5-tribenzyloxy-6-[4-chloro-3-[[4-(2,2-difluoroethoxy)phenyl]methyl]phenyl]-6-methoxy-tetrahydropyran-2-yl]methoxy]tert-butyl-dimethyl-silane 60% NaH (1.9 g, 47.21 mmol) and 15 mL THF were added into a 100 mL reaction flask and cooled to 0° C., followed by dropwise addition of (2S,3R,4S,5S,6R)-6-[(tert-butyl(dimethyl)silyl)oxymethyl]-2-[4-chloro-3-[[4-(2,2-difluoroethoxy)phenyl]methyl]phenyl]-2-methoxy-tetrahydropyran-3,4,5-triol 12f (4.96 g, 8.43 mmol) in THF (18 mL) within 10 minutes at 0° C. The reaction mixture was stirred for 30 minutes. Then a solution of benzyl bromide (7.21 g, 42.15 mmol) in N,N-dimethyl formamide (10 mL) was dropwise added before the reaction mixture was warmed and stirred for 16 hours at room temperature. Thereafter, the reaction mixture was partitioned after 200 mL ethyl acetate, saturated sodium bicarbonate (70 mL) and water (50 mL) were added. The organic extract was washed with 0.01 N hydrochloric acid (60 mL) and saturated sodium chloride solution, dried over anhydrous magnesium sulfate, and filtered. The filtrate was concentrated under reduced pressure to obtain the title compound [[(2R,3R,4S,5R,6S)-3,4,5-tribenzyloxy-6-[4-chloro-3-[[4-(2,2-difluoroethoxy)phenyl]methyl]phenyl]-6-methoxy-tetrahydropyran-2-yl]methoxy]tert-butyl-dimethyl-silane 12g (7.25 g, pale yellow liquid), which was used directly in the next step without purification.

Step 8

[(2R,3R,4S,5R,6S)-3,4,5-tribenzyloxy-6-[4-chloro-3-[[4-(2,2-difluoroethoxy)phenyl]methyl]phenyl]-6-methoxy-tetrahydropyran-2-yl]methanol

[[(2R,3R,4S,5R,6S)-3,4,5-tribenzyloxy-6-[4-chloro-3-[[4-(2,2-difluoroethoxy)phenyl]methyl]phenyl]-6-methoxy-tetrahydropyran-2-yl]methoxy]tert-butyl-dimethyl-silane 12g (4.10 g, 4.78 mmol) was dissolved in 30 mL methanol, followed by addition of acetyl chloride (51 μL, 0.72 mmol). The reaction mixture was stirred for 1 hour. Thereafter, the reaction mixture was concentrated under reduced pressure and the resulting residue was purified by column chromatography to obtain the title compound [(2R,3R,4S,5R,6S)-3,4,5-tribenzyloxy-6-[4-chloro-3-[[4-(2,2-difluoro-ethoxy)phenyl]methyl]phenyl]-6-methoxy-tetrahydropyran-2-yl]methanol 12h (1.23 g, white grease), yield: 34.6%.

Step 9

(2S,3S,4S,5R,6S)-3,4,5-tribenzyloxy-6-[4-chloro-3-[[4-(2,2-difluoroethoxy)phenyl]methyl]phenyl]-6-methoxy-tetrahydropyran-2-carbaldehyde Oxalyl chloride (0.18 mL, 2.16 mmol) was dissolved in 5 mL methylene chloride and cooled to −78° C., followed by dropwise addition of a solution (3 mL) of dimethyl sulfoxide (0.23 mL, 3.31 mmol) in methylene chloride, and the reaction mixture was stirred for 15 minutes. 10 mL solution of [(2R,3R,4S,5R,6S)-3,4,5-tribenzyloxy-6-[4-chloro-3-[[4-(2,2-difluoroethoxy)phenyl]methyl]phenyl]-6-methoxy-tetrahydropyran-2-yl]methanol 12h (1.23 g, 1.66 mmol) in methylene chloride were dropwise added before the mixture was stirred for 40 minutes. The reaction mixture was warmed to room temperature and stirred for 3 hours after triethylamine (1.2 mL, 8.31 mmol) was dropwise added. Thereafter, the reaction mixture was partitioned after 5 mL 1 M hydrochloric acid were added. The aqueous phase was extracted with ethyl acetate (20 mL×2) and the organic extract was combined, dried over anhydrous magnesium sulfate, and filtered. The filtrate was concentrated under reduced pressure to obtain the title compound (2S,3S,4S,5R,6S)-3,4,5-tribenzyloxy-6-[4-chloro-3-[[4-(2,2-difluoro-ethoxy)phenyl]methyl]

phenyl]-6-methoxy-tetrahydropyran-2-carbaldehyde 12i (1.10 g, yellow grease), which was used directly in the next step without purification.

Step 10

(2S,3S,4S,5R,6S)-3,4,5-tribenzyloxy-6-[4-chloro-3-[[4-(2,2-difluoroethoxy)phenyl]methyl]phenyl]-2-(hydroxymethyl)-6-methoxy-tetrahydropyran-2-carbaldehyde (2S,3S,4S,5R,6S)-3,4,5-tribenzyloxy-6-[4-chloro-3-[[4-(2,2-difluoroethoxy)phenyl]methyl]phenyl]-6-methoxy-tetrahydropyran-2-carbaldehyde 12i (1.10 g, 1.48 mmol) was dissolved in 20 mL 1,4-dioxane, followed by addition of 2.5 mL of 37% formaldehyde solution and dropwise addition of 4 mL of 2.9 M sodium hydroxide solution. The reaction mixture was stirred for 25 hours at 70° C. Thereafter, the reaction mixture was concentrated under reduced pressure before 20 mL water and 10 mL saturated sodium chloride solution were added. The aqueous phase was extracted with ethyl acetate (30 mL×3) and the organic extract was combined, dried over anhydrous magnesium sulfate, and filtered. The filtrate was concentrated under reduced pressure to obtain the title compound (2S,3S,4S,5R,6S)-3,4,5-tribenzyloxy-6-[4-chloro-3-[[4-(2,2-difluoroethoxy)phenyl]methyl]phenyl]-2-(hydroxymethyl)-6-methoxy-tetrahydropyran-2-carbaldehyde 12j (1.09 g, yellow grease), which was used directly in the next step without purification.

Step 11

[(3S,4S,5R,6S)-3,4,5-tribenzyloxy-6-[4-chloro-3-[[4-(2,2-difluoroethoxy)phenyl]methyl]phenyl]-2-(hydroxymethyl)-6-methoxy-tetrahydropyran-2-yl]methanol (2S,3S,4S,5R,6S)-3,4,5-tribenzyloxy-6-[4-chloro-3-[[4-(2,2-difluoroethoxy)phenyl]methyl]phenyl]-2-(hydroxymethyl)-6-methoxy-tetrahydropyran-2-carbaldehyde 12j (1.09 g, 1.42 mmol) was dissolved in 30 mL of mixed solution (THF and MeOH, v:v=1:2), followed by addition of sodium borohydride (108 mg, 2.83 mmol) in batch. The reaction mixture was stirred for 30 minutes before 20 mL water and 30 mL water were added. The aqueous phase was extracted with ethyl acetate (30 mL×3) and the organic extract was washed with saturated sodium chloride solution (30 mL) and combined, dried over anhydrous magnesium sulfate, and filtered. The filtrate was concentrated under reduced pressure and the resulting residue was purified by column chromatography to obtain the title compound [(3S,4S,5R,6S)-3,4,5-tribenzyloxy-6-[4-chloro-3-[[4-(2,2-difluoroethoxy)phenyl]methyl]phenyl]-2-(hydroxymethyl)-6-methoxy-tetrahydropyran-2-yl]methanol 12k (293 mg, yellow grease), yield: 27.0%.

Step 12

[(1S,2S,3S,4R,5S)-2,3,4-tribenzyloxy-5-[4-chloro-3-[[4-(2,2-difluoroethoxy)phenyl]methyl]phenyl]-6,8-dioxabicyclo[3.2.1]octan-1-yl]methanol

[(3S,4S,5R,6S)-3,4,5-tribenzyloxy-6-[4-chloro-3-[[4-(2,2-difluoroethoxy)phenyl]methyl]phenyl]-2-(hydroxymethyl)-6-methoxy-tetrahydropyran-2-yl]methanol 12k (293 mg, 0.38 mmol) was dissolved in 10 mL dichloromethane, followed by dropwise addition of trifluoroacetic acid (0.1 mL). The reaction mixture was stirred for 1 hour. Thereafter, the reaction mixture was concentrated under reduced pressure and the resulting residue was purified by column chromatography to obtain the title compound [(1S,2S,3S,4R,5S)-2,3,4-tribenzyloxy-5-[4-chloro-3-[[4-(2,2-difluoroethoxy)phenyl]methyl]phenyl]-6,8-dioxabicyclo[3.2.1]octan-1-yl]methanol 12m (76 mg, white solid), yield: 27.6%.

Step 13

(1S,2S,3S,4R,5S)-5-[4-chloro-3-[[4-(2,2-difluoroethoxy)phenyl]methyl]phenyl]-1-(hydroxymethyl)-6,8-dioxabicyclo[3.2.1]octane-2,3,4-triol

[(1S,2S,3S,4R,5S)-2,3,4-tribenzyloxy-5-[4-chloro-3-[[4-(2,2-difluoroethoxy)phenyl]methyl]phenyl]-6,8-dioxabicyclo[3.2.1]octan-1-yl]methanol 12m (76 mg, 0.10 mmol) was dissolved in 10 mL of mixed solution (THF and MeOH, v:v=1:1), followed by addition of o-dichlorobenzene (103 µL, 0.9 mmol) and Palladium/carbon (180 mg, 10%). The mixture was exchanged with H2 three times and stirred for 2 hours, then filtered. The filtrate was concentrated under reduced pressure and the resulting residue was purified by column chromatography to obtain the title compound (1S,2S,3S,4R,5S)-5-[4-chloro-3-[[4-(2,2-difluoroethoxy)phenyl]methyl]phenyl]-1-(hydroxymethyl)-6,8-dioxabicyclo[3.2.1]octane-2,3,4-triol 12 (17 mg, pale yellow solid), yield: 34.0%. MS m/z (ESI): 490.24 [M+18]; 1H NMR (400 MHz, CD3OD): δ 7.48-7.49 (m, 1H), 7.37-7.39 (m, 2H), 7.15-7.17 (d, 2H), 6.88-6.91 (d, 2H), 6.02-6.29 (ddt, 1H), 4.23-4.24 (d, 1H), 4.20-4.21 (d, 1H), 4.16-4.17 (d, 1H), 4.08 (s, 2H), 3.78-3.88 (m, 2H), 3.67-3.72 (m, 2H), 3.55-3.57 (m, 2H).

TEST EXAMPLES

SGLT1 and SGLT2 Activity Measurement

The following methods can be used to determine the inhibitory activity of the compounds according to the present invention for SGLT1 and SGLT2. Experimental methods are briefly described as follows.

SGLT1 or SGLT2 instantaneous transfer strain (cell density: 1–1.5×104) was seeded into each well of a 96-well plate (Prepared according to existing literature "Diabetes, 57, 1723-1729, 2008", wherein cDNA of SGLT1 and SGLT2 was purchased from Origene) and incubated in a humidified environment containing 5% CO2 at 37° C. for 48 hours. Then each well of the 96-well plate was washed with 200 µL sodium-free buffer twice and 90 µL sodium-containing buffer solution containing test compounds having different concentrations was added, each of the test compounds having its corresponding concentration repeated in three wells. The compounds were incubated at 37° C. for 15 minutes and then each well of the 96-well plate was incubated with [14C] Methyl α-D-glucopyranoside (10 µL, totally 0.1 µCi) for another 2 hours at 37° C. Thereafter, supernatant was removed; the cell pellet was washed twice with precooling no-sodium buffer and lysed in 200 mM NaOH (100 µL). 100 µL scintillation fluid was added and mixed and 14C was quantitatively detected using liquid scintillation.

The IC50 values of the compounds can be calculated using the aggregation rate at different concentrations.

| Example Number | IC$_{50}$ (SGLT2)/nM | IC$_{50}$ (SGLT1)/µM |
|---|---|---|
| 1 | 9.53 | >2 |
| 2 | 3.65 | >2 |
| 3 | 8.08 | >2 |
| 4 | 6.92 | 2.6 |
| 5 | 1.49 | 2.52 |
| 7 | 4.58 | 14.26 |
| 8 | 1.42 | 0.6 |
| 9 | 9.28 | 1.26 |

-continued

| Example Number | IC$_{50}$ (SGLT2)/nM | IC$_{50}$ (SGLT1)/μM |
|---|---|---|
| 10 | 3.31 | 1.22 |
| 11 | 6.35 | 3.55 |

Conclusion: The compounds of the present invention have high selectivity and significantly inhibit SGLT2.

Preliminary Evaluation of the Hypoglycemic Effect

The purpose was to observe the effect of the test compounds on blood glucose levels of glucose-load mice. Determination and analysis of sugar content in the blood collected from the mouse tail was determined at different times within 2 hours of administration to provide preliminary evaluation of the hypoglycemic activity in vivo.

The compounds tested were compounds of Example 1, Example 2 and Example 4. The experimental animals used were 24 healthy ICR mice (weighing 20-24 g), 12 female and 12 male, purchased from Shanghai Super—B&K laboratory animal Corp. Ltd., animal production license number: SCXK (Shanghai) 2008-0016.

To prepare the drug, a certain amount of compounds were weighed and dissolved in water (pure water OWN) and formulated into an aqueous solution of 0.1 mg/mL (5% DMSO for solubilization).

Test Methods
1. Dose Settings

The administered dose was 1 mg/kg, blank and water groups (containing 5% DMSO).

2. Administration Mode

20% glucose solution (4 g/kg, 0.8 mL each mouse) was given after 15 minutes of administration.

3. Determination of Blood Glucose

Administering in dose and measuring the blood glucose value (−15 minutes).

20% glucose solution (4 g/kg, 0.8 mL each mouse) was given 15 minutes after administering, then the blood glucose value of each mouse was measured at minute 0, 15, 30, 45, 60, 120 using Roche ACCU-CHEK, and the decline rate of the medicine-time area under the curve (AUC) was calculated.

Test results are shown in the following table:

| Example Number | AUC decline rate % |
|---|---|
| 1 | 10.04 |
| 2 | 12.95 |
| 4 | 15.88 |
| 5 | 14.13 |
| 6 | 10.15 |
| 7 | 10.75 |
| 8 | 20.49 |

Conclusion: concerning the compounds according to the present invention after 15 minutes of administering, the blood glucose was significantly decreased.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:
1. A compound of formula (I):

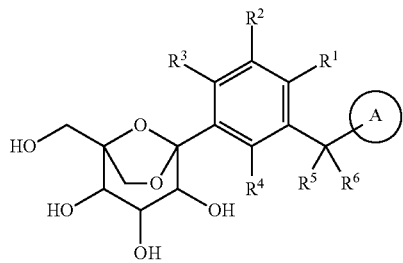

or a pharmaceutically acceptable salt or stereoisomer thereof, wherein ring A is aryl, wherein the aryl is optionally substituted by one or more groups selected from the group consisting of halogen, alkyl, alkenyl, alkynyl, cycloalkyl, heterocyclyl, aryl, heteroaryl, —OR$^7$, —S(O)$_m$R$^7$, —C(O)R$^7$, —C(O)OR$^7$, —NR$^8$R$^9$, and —C(O)NR$^8$R$^9$, wherein the alkyl, cycloalkyl, hetercyclyl, aryl, and heteroaryl are each independently and optionally substituted by one or more groups selected from the group consisting of deuterium, halogen, alkenyl, alkynyl, nitro, cyano, alkoxyl, cycloalkyl, —OR$^7$, —S(O)$_m$R$^7$, —C(O)R$^7$, —C(O)OR$^7$, —NR$^8$R$^9$, and —C(O)NR$^8$R$^9$;

R$^1$, R$^2$, R$^3$, and R$^4$ are each independently selected from the group consisting of hydrogen, halogen, cyano, hydroxyl, amino, alkyl, alkoxyl, cycloalkyl, aryl, and heteroaryl, wherein the alkyl, alkoxyl, cycloalkyl, aryl, and heteroaryl are each independently and optionally substituted by one or more groups selected from the group consisting of deuterium, halogen, hydroxyl, amino, alkyl, alkoxyl, carboxyl, and carboxylic ester; alternatively, R$^2$ and R$^3$ are connected together with phenyl and fuse into a ring which is optionally selected from the group consisting of cycloalkyl, heterocyclyl, aryl and heteroaryl, wherein the cycloalkyl, heterocyclyl, aryl and heteroaryl are each independently and optionally substituted by one or more groups selected from the group consisting of halogen, hydroxyl, amino, alkyl, alkoxyl, alkenyl, alkynyl, cycloalkyl, heterocyclyl, aryl, heteroaryl, carboxyl, and carboxylic ester;

provided that when ring A is phenyl, R$^2$, R$^3$ and R$^4$ are each hydrogen, and R$^1$ is selected from the group consisting of hydrogen, C$_{1-4}$ alkyl, F, Cl, cyano and —OR$^{10}$, then ring A is not substituted by a single group selected from the group consisting of C$_{1-4}$ alkyl, F, Cl, cyano, hydroxyl, —OR$^{11}$, C$_{1-2}$ alkyl substituted with F, —S(O)$_2$R$^{11}$, C$_{3-6}$ alkyl, and C$_{5-6}$ saturated heterocyclyl having 1-2 N, O, or S;

R$^5$ and R$^6$ are each independently selected from the group consisting of hydrogen and deuterium;

R$^7$ is selected from the group consisting of hydrogen, deuterium, alkyl, cycloalkyl, heterocyclyl, aryl, and heteroaryl, wherein the alkyl, cycloalkyl, heterocyclyl, aryl, and heteroaryl are each independently and optionally substituted by one or more groups selected from the group consisting of alkyl, halogen, hydroxyl, amino, alkoxyl, cycloalkyl, heterocyclyl, aryl, heteroaryl, carboxyl, and carboxylic ester;

R[8] and R[9] are each independently selected from the group consisting of hydrogen, alkyl, cycloalkyl, heterocyclyl, aryl and heteroaryl, wherein the alkyl, cycloalkyl, heterocyclyl, aryl, and heteroaryl are each independently and optionally substituted by one or more groups selected from the group consisting of alkyl, halogen, hydroxyl, amino, alkoxyl, cycloalkyl, heterocyclyl, aryl, heteroaryl, carboxyl, and carboxylic ester;

alternatively, R[8] and R[9] are connected together with the attached nitrogen to form a heterocyclyl, wherein the heterocyclyl contains one or more N, O, or S(O)$_m$ heteroatoms, and the heterocyclyl is optionally substituted by one or more groups selected from the group consisting of alkyl, halogen, hydroxyl, alkoxyl, cycloalkyl, heterocyclyl, aryl, heteroaryl, carboxyl, and carboxylic ester; R[10] is a C$_{1-4}$ alkyl;

R[11] is selected from the group consisting of a C$_{1-4}$ alkyl, a C$_{1-4}$ alkyl substituted by hydroxyl, alkoxyl or carboxylic ester,

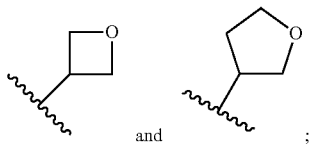 [SMILES: *C1COC1 ; *C1CCOC1]

and m is 0, 1, or 2.

2. The compound of formula (I) or a pharmaceutically acceptable salt or stereoisomer thereof according to claim 1, wherein the compound is of formula (II):

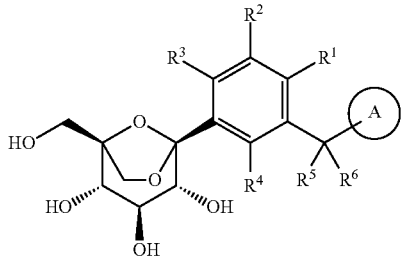

or a pharmaceutically acceptable salt or stereoisomer thereof.

3. The compound of formula (I) or a pharmaceutically acceptable salt or stereoisomer thereof according to claim 1, wherein R[2], R[3] and R[4] are each independently hydrogen; and R[1] is halogen.

4. The compound of formula (I) or a pharmaceutically acceptable salt or stereoisomer thereof according to claim 1, wherein ring A is phenyl, wherein the phenyl is optionally substituted by 1 to 5 groups independently selected from the group consisting of halogen and —OR[7]; R[7] is alkyl, wherein the alkyl is optionally substituted by 1 to 3 groups independently selected from the group consisting of deuterium, halogen, alkoxyl and cycloalkoxyl.

5. A compound of formula (I):

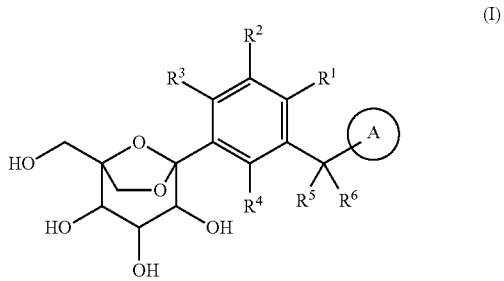

or a pharmaceutically acceptable salt or stereoisomer thereof, wherein ring A is heteroaryl, wherein the heteroaryl is optionally substituted by one or more groups selected from the group consisting of halogen, alkyl, alkenyl, alkynyl, cycloalkyl, heterocyclyl, aryl, heteroaryl, —OR[7], —S(O)$_m$, R[7], —C(O)R[7], —C(O)OR[7], —NR[8]R[9] and —C(O)NR[8]R[9], wherein the alkyl, cycloalkyl, hetercyclyl, aryl and heteroaryl are each independently and optionally substituted by one or more groups selected from the group consisting of deuterium, halogen, alkenyl, alkynyl, nitro, cyano, alkoxy, cycloalkyl, —OR[7], —S(O)$_m$, R[7], —C(O)R[7], —C(O)OR[7], —NR[8]R[9] and —C(O)NR[8]R[9]$_9$;

R[1], R[2], R[3] and R[4] are each independently selected from the group consisting of hydrogen, halogen, cyano, hydroxyl, amino, alkyl, alkoxyl, cycloalkyl, aryl, and heteroaryl, wherein the alkyl, alkoxyl, cycloalkyl, aryl, and heteroaryl are each independently and optionally substituted by one or more groups selected from the group consisting of deuterium, halogen, hydroxyl, amino, alkyl, alkoxyl, carboxyl, and carboxylic ester; alternatively, R[2] and R[3] are connected together with phenyl and fuse into a ring which is optionally selected from the group consisting of cycloalkyl, heterocyclyl, aryl and heteroaryl, wherein the cycloalkyl, heterocyclyl, aryl and heteroaryl are each independently and optionally substituted by one or more groups selected from the group consisting of halogen, hydroxyl, amino, alkyl, alkoxyl, alkenyl, alkynyl, cycloalkyl, heterocyclyl, aryl, heteroaryl, carboxyl, and carboxylic ester;

R[5] and R[6] are each independently selected from the group consisting of hydrogen and deuterium;

R[7] is selected from the group consisting of hydrogen, deuterium, alkyl, cycloalkyl, heterocyclyl, aryl, and heteroaryl, wherein the alkyl, cycloalkyl, heterocyclyl, aryl, and heteroaryl are each independently and optionally substituted by one or more groups selected from the group consisting of alkyl, halogen, hydroxyl, amino, alkoxyl, cycloalkyl, heterocyclyl, aryl, heteroaryl, carboxyl, and carboxylic ester;

R[8] and R[9] are each independently selected from the group consisting of hydrogen, alkyl, cycloalkyl, heterocyclyl, aryl and heteroaryl, wherein the alkyl, cycloalkyl, heterocyclyl, aryl, and heteroaryl are each independently and optionally substituted by one or more groups selected from the group consisting of alkyl, halogen, hydroxyl, amino, alkoxyl, cycloalkyl, heterocyclyl, aryl, heteroaryl, carboxyl, and carboxylic ester;

alternatively, R⁸ and R⁹ are connected together with the attached nitrogen to form a heterocyclyl, wherein the heterocyclyl contains one or more N, O, or S(O)$_m$ heteroatoms, and the heterocyclyl is optionally substituted by one or more groups selected from the group consisting of alkyl, halogen, hydroxyl, alkoxyl, cycloalkyl, heterocyclyl, aryl, heteroaryl, carboxyl, and carboxylic ester; R¹⁰ is a C$_{1-4}$ alkyl; and m is 0, 1 or 2.

6. The compound of formula (I) or a pharmaceutically acceptable salt or stereoisomer thereof according to claim 5, wherein R², R³ and R⁴ are each independently hydrogen; and R¹ is a halogen.

7. The compound of formula (I) or a pharmaceutically acceptable salt or stereoisomer thereof according to claim 5, wherein ring A is

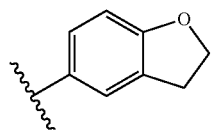

or thienyl.

8. The compound of formula (I) or a pharmaceutically acceptable salt or stereoisomer thereof according to claim 1, wherein ring A is optionally substituted by one or more groups selected from the group consisting of halogen and —OR⁷; provided that when ring A is substituted by —OR⁷, wherein R⁷ is a C$_{1-4}$ alkyl, then ring A is also substituted by one or more halogen atoms.

9. The compound of formula (I) or a pharmaceutically acceptable salt or stereoisomer thereof according claim 1, wherein R⁵ or R⁶ is a deuterium atom.

10. The compound of formula (I) or a pharmaceutically acceptable salt or stereoisomer thereof according to claim 1, wherein R⁷ is alkyl, and the alkyl is optionally substituted by one or more deuterium atoms.

11. A compound or a pharmaceutically acceptable salt or stereoisomer thereof selected from the group consisting of:

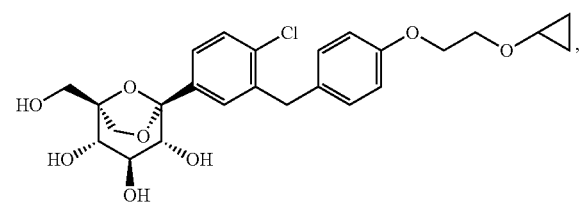

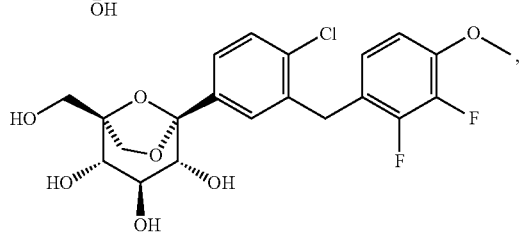

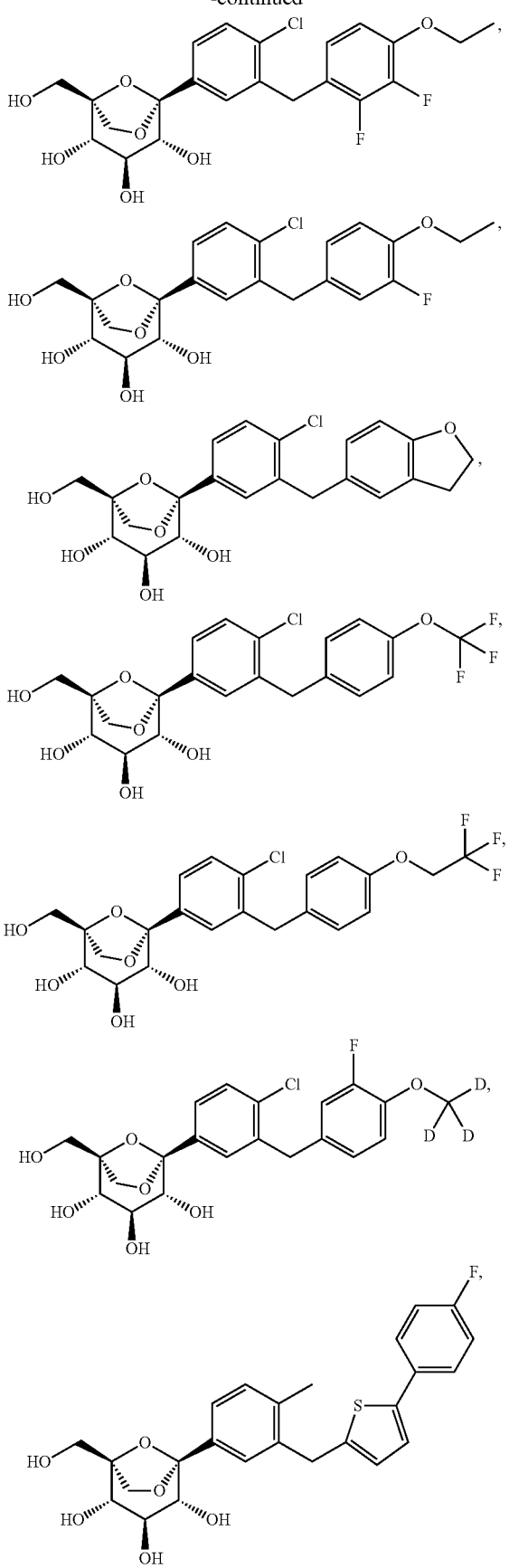

-continued

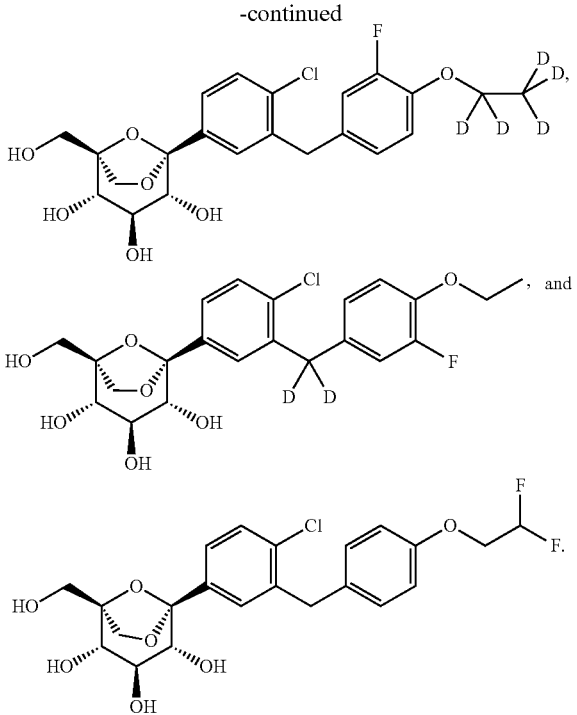

12. A process for preparing a compound of formula (I) according to claim 1, the process comprising:
(i) converting a compound of formula (IA):

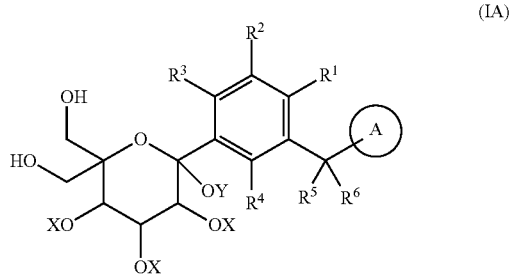

(IA)

to a compound of formula (IB):

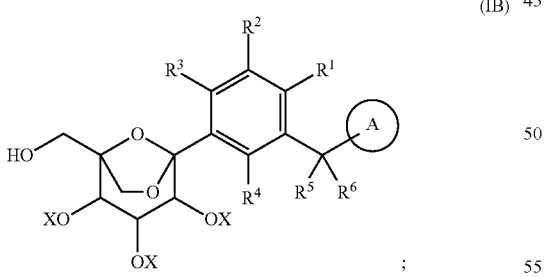

(IB)

and
(ii) deprotecting the compound of formula (IB) into the compound of formula (I), wherein X and Y are hydroxyl protecting groups.

13. A pharmaceutical composition comprising a therapeutically effective amount of a compound of formula (I) or a pharmaceutically acceptable salt or stereoisomer thereof according to claim 1, and a pharmaceutically acceptable carrier.

14. A method for treating a disease selected from the group consisting of diabetes, retinopathy, neuropathy, nephropathy, insulin resistance, hyperglycemia, hyperinsulinemia, elevated levels of fatty acids or glycerol, hyperlipidemia, obesity, hypertriglyceridemia, syndrome X, atherosclerosis and hypertension in a subject in need of treatment thereof, the method comprising administering to the subject a pharmaceutical composition according to claim 13.

15. The process according to claim 12, wherein X and Y are each independently alkyl or benzyl.

16. A method for inhibiting a sodium-dependent glucose transporter in a subject in need thereof, the method comprising administering to the subject a pharmaceutical composition according to claim 13.

17. A method for slowing development or onset of a disease selected from the group consisting of diabetes, retinopathy, neuropathy, nephropathy, insulin resistance, hyperglycemia, hyperinsulinemia, elevated levels of fatty acids or glycerol, hyperlipidemia, obesity, hypertriglyceridemia, syndrome X, atherosclerosis, and hypertension in a subject in need thereof, the method comprising administering to the subject the pharmaceutical composition according to claim 13.

18. The compound of formula (I) or a pharmaceutically acceptable salt or stereoisomer thereof according to claim 5, wherein ring A is optionally substituted by one or more groups selected from the group consisting of halogen and —$OR^7$; provided that when ring A is substituted by —$OR^7$, wherein $R^7$ is a $C_{1-4}$ alkyl, then ring A is also substituted by one or more halogen atoms.

19. The compound of formula (I) or a pharmaceutically acceptable salt or stereoisomer thereof according claim 5, wherein $R^5$ or $R^6$ is a deuterium atom.

20. The compound of formula (I) or a pharmaceutically acceptable salt or stereoisomer thereof according to claim 5, wherein $R^7$ is alkyl, and the alkyl is optionally substituted by one or more deuterium atoms.

21. A process for preparing a compound of formula (I) according to claim 5, the process comprising:
(i) converting a compound of formula (IA):

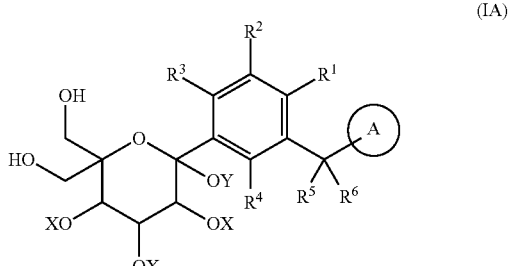

(IA)

to a compound of formula (IB):

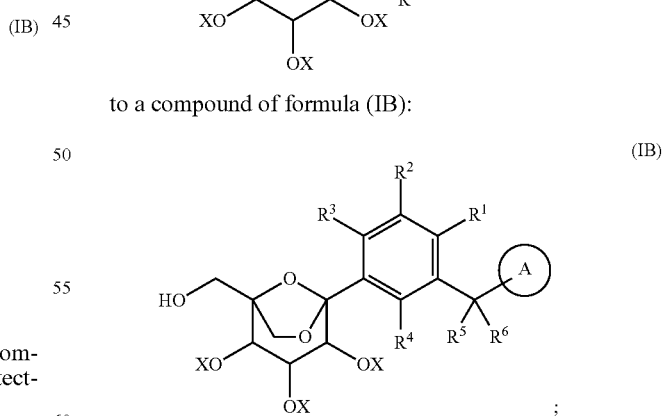

(IB)

and
(ii) deprotecting the compound of formula (IB) into the compound of formula (I), wherein X and Y are hydroxyl protecting groups.

22. A pharmaceutical composition comprising a therapeutically effective amount of a compound of formula (I) or a pharmaceutically acceptable salt or stereoisomer thereof according to claim 5, and a pharmaceutically acceptable carrier.

23. A method for treating a disease selected from the group consisting of diabetes, retinopathy, neuropathy, nephropathy, insulin resistance, hyperglycemia, hyperinsulinemia, elevated levels of fatty acids or glycerol, hyperlipidemia, obesity, hypertriglyceridemia, syndrome X, atherosclerosis and hypertension in a subject in need of treatment thereof, the method comprising administering to the subject the pharmaceutical composition according to claim 22.

24. The process according to claim 21, wherein X and Y are each independently alkyl or benzyl.

25. A method for inhibiting a sodium-dependent glucose transporter in a subject in need thereof, the method comprising administering to the subject the pharmaceutical composition according to claim 22.

26. A method for slowing development or onset of a disease selected from the group consisting of diabetes, retinopathy, neuropathy, nephropathy, insulin resistance, hyperglycemia, hyperinsulinemia, elevated levels of fatty acids or glycerol, hyperlipidemia, obesity, hypertriglyceridemia, syndrome X, atherosclerosis, and hypertension in a subject in need thereof, the method comprising administering to the subject the pharmaceutical composition according to claim 22.

* * * * *